(12) United States Patent
Knust et al.

(10) Patent No.: US 8,318,759 B2
(45) Date of Patent: Nov. 27, 2012

(54) PYRROLIDINE DERIVATIVES AS NK3 RECEPTOR ANTAGONISTS

(75) Inventors: Henner Knust, Rheinfelden (DE); Anja Limberg, Basel (CH); Matthias Nettekoven, Grenzach-Wyhlen (DE); Hasane Ratni, Habsheim (FR); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 150 days.

(21) Appl. No.: 12/703,804

(22) Filed: Feb. 11, 2010

(65) Prior Publication Data

US 2010/0210659 A1 Aug. 19, 2010

(30) Foreign Application Priority Data

Feb. 18, 2009 (EP) ..................... 09153097

(51) Int. Cl.
*A61K 31/496* (2006.01)
*C07D 241/04* (2006.01)
*C07D 401/14* (2006.01)

(52) U.S. Cl. ........ 514/275; 544/224; 544/242; 544/322; 514/256

(58) Field of Classification Search .............. 544/224, 544/242, 322; 514/256, 275
See application file for complete search history.

(56) References Cited

U.S. PATENT DOCUMENTS

| | | | | |
|---|---|---|---|---|
| 7,514,441 B2 * | 4/2009 | Yasuma et al. | ............. | 514/259.3 |
| 7,585,886 B2 * | 9/2009 | Hachiya et al. | ............... | 514/423 |
| 7,812,021 B2 * | 10/2010 | Jablonski et al. | ........... | 514/235.5 |
| 7,893,062 B2 * | 2/2011 | Bissantz et al. | ............... | 514/235.5 |
| 8,012,998 B2 * | 9/2011 | Jablonski et al. | ............. | 514/333 |
| 8,022,099 B2 * | 9/2011 | Bissantz et al. | ............... | 514/426 |
| 8,063,075 B2 * | 11/2011 | Jablonski et al. | ............. | 514/340 |

FOREIGN PATENT DOCUMENTS

| | | |
|---|---|---|
| WO | 2008/128891 | 10/2008 |
| WO | 2009/0191763 | 2/2009 |

OTHER PUBLICATIONS

Tooney et al , Neurosci. Letters, 2000, vol. 283 pp. 185-188.
Giardina et al,, Exp. Opin. Ther. Patents, 2000, vol. 10, pp. 939-960.
Jung et al., Neuroscience, 1996, vol. 74, pp. 403-414.
Marco et al., Neuropeptides, 1998, vol. 32, pp. 481-488.
Kamali, F., Current Opinion in Investigational Drugs, 2001 vol. 2(7) pp. 950-956 7.
Wermuth, C. G: "Molecular Variations Based on Isoteric Replacments" Practice of Medicinal Chemistry (1996) 203-237, XP002190259.

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to a compounds of formula I

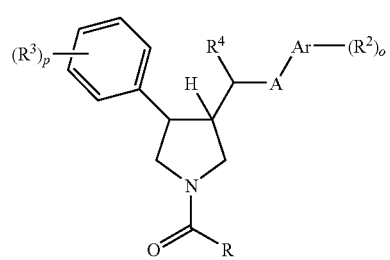

wherein A, Ar, R, R2, R3, R4, p, and o are as defined in the specification and claims or to a pharmaceutically active salt thereof. The present compounds are high potential NK-3 receptor antagonists for the treatment of depression, pain, psychosis, Parkinson's disease, schizophrenia, bipolar disorders, anxiety and attention deficit hyperactivity disorder (ADHD).

10 Claims, No Drawings

PYRROLIDINE DERIVATIVES AS NK3 RECEPTOR ANTAGONISTS

PRIORITY TO RELATED APPLICATION(S)

This application claims the benefit of European Patent Application No. 09153097.2, filed Feb. 18, 2009, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.).

SUMMARY OF THE INVENTION

The present invention provides compounds of formula I

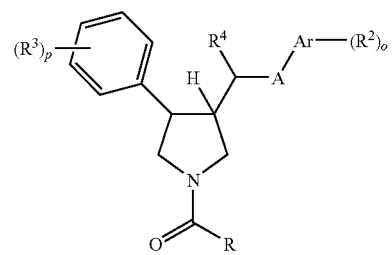

wherein
A is —$NR'$—, —S—, —S(O)— or —$S(O)_2$—;
R' is hydrogen or lower alkyl;
Ar is aryl or is a five or six membered heteroaryl group containing one or two N-atoms;
R is a five or six membered heterocyclic group

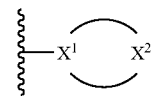

wherein
$X^1$ is N or CH; and
$X^2$ is —$N(R^1)$—, —$CH_2$—, —O—, —S—, —S(O)—, or —$S(O)_2$—,
$R^1$ is hydrogen, lower alkyl, $S(O)_2$-lower alkyl, C(O)-lower alkyl, C(O)-cycloalkyl optionally substituted by lower alkyl;
with the proviso that at least one of $X^1$ or $X^2$ contains a heteroatom,
or is a five or six membered heteroaryl group containing one or two N-atoms, which groups are unsubstituted or are substituted by one or two $R^{1'}$;
wherein
$R^{1'}$ is lower alkyl or cyano;
$R^2$ is lower alkyl substituted by halogen, cyano or nitro;
$R^3$ is halogen;

$R^4$ is hydrogen or lower alkyl;

o is 1 or 2; wherein when o is 2, each $R^2$ is the same or different; and p is 1 or 2; wherein when p is 2, each $R^3$ is the same or different;

or a pharmaceutically active salt thereof.

The invention includes all stereoisomeric forms, including individual diastereoisomers and enantiomers of the compound of formula (I) as well as racemic and non-racemic mixtures The present compounds are high potential NK-3 receptor antagonists for the treatment of depression, pain, psychosis, Parkinson's disease, schizophrenia, bipolar disorders, anxiety and attention deficit hyperactivity disorder (ADHD).

The present invention provides compounds of formula I per se. It also provides pharmaceutical compositions containing such compounds and methods for the manufacture of such compounds and compositions. The invention further provides methods for the control or prevention of illnesses such as depression, pain, bipolar disorders, psychosis, Parkinson's disease, schizophrenia, anxiety and attention deficit hyperactivity disorder (ADHD).

The preferred indications using the compounds of the present invention are depression, psychosis, Parkinson's disease, schizophrenia, bipolar disorders, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "halogen" denotes chlorine, iodine, fluorine and bromine.

The term "cycloalkyl" denotes a saturated carbon ring containing from 3-6 carbon atoms, for example, cyclopropyl, cyclobutyl, cyclopentyl or cyclohexyl and the like.

The term "aryl" denotes a cyclic aromatic hydrocarbon radical consisting of one or more fused rings containing 6-14 carbon atoms in which at least one ring is aromatic in nature, for example phenyl, naphthyl, 1,2,3,4-tetrahydronaphthalenyl or indanyl. Preferred is the phenyl group.

The term "five or six membered heteroaryl" denotes a cyclic aromatic radical consisting of one or more fused rings containing 5-14 ring atoms, preferably containing 5-10 ring atoms, in which at least one ring is aromatic in nature and which contains at least one heteroatom selected from N, for example quinoxalinyl, dihydroisoquinolinyl, pyrazin-2-yl, pyrazolyl, 2,4-dihydro-pyrazol-3-one, pyridinyl, isoxazolyl, pyridyl, pyrimidin-4-yl, pyrimidin-5-yl, [1,2,4]triazol-1-yl, [1,6]naphthyridin-2-yl, tetrazolyl, thiazolyl, imidazol-1-yl, Preferred heteroaryl group is pyridine-2, 3 or 4-yl or pyrimidinyl.

The term "five or six membered heterocyclyl" ring denotes a five or six membered non-aromatic ring containing one or two heteroatoms selected from N, S and O, for example the following groups: morpholinyl, [1,4]diazepam-1-yl, piperazinyl, pyrrolidinyl, piperidin-1-yl, tetrahydrofuranyl, tetrahydrothiophenyl, piperidin-4-yl or 1,1-dioxo-$\lambda^6$-thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

In one embodiment, compounds of formula I are those of formula I-A,

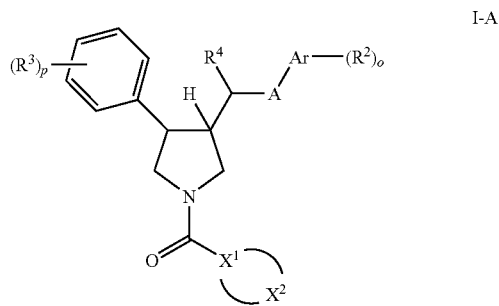

I-A wherein the definitions are as described above and $X^1$ is N or CH;

$X^2$ is —N($R^1$)—, —$CH_2$—, —O—, —S—, —S(O)—, —$S(O)_2$—, $R^1$ is hydrogen, lower alkyl, $S(O)_2$-lower alkyl, C(O)-lower alkyl, C(O)-cycloalkyl optionally substituted by lower alkyl;

with the proviso that at least one of $X^1$ or $X^2$ is a heteroatom.

In another embodiment, compounds of formula I are further those of formula I-B,

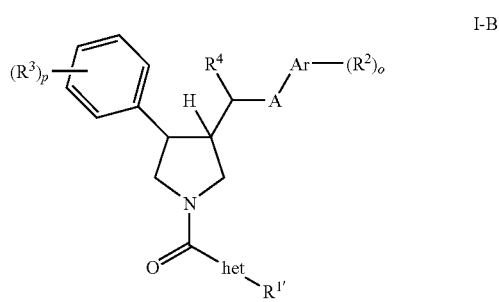

I-B wherein het is a five or six membered heteroaryl group containing one or two N-atoms, which groups are unsubstituted or are substituted by one or two $R^{1'}$ and wherein $R^{1'}$ is lower alkyl or cyano, and the other definitions are as described above.

In detail, preferred are compounds of formula I-A are those wherein

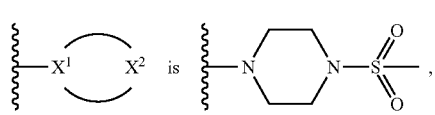

for example
(3SR,4RS)-[3-(3,4-dichloro-phenyl)-4-(4-trifluoromethyl-phenylsulfanylmethyl)-pyrrolidin-1-yl]-(4-methanesulfonyl-piperazin-1-yl)-methanone;
(3SR,4RS)-[3-(4-chloro-phenylsulfanylmethyl)-4-(3,4-dichloro-phenyl)-pyrrolidin-1-yl]-(4-methanesulfonyl-piperazin-1-yl)-methanone;
(3SR,4RS)-4-[4-(3,4-dichloro-phenyl)-1-(4-methanesulfonyl-piperazine-1-carbonyl)-pyrrolidin-3-ylmethylsulfanyl]-benzonitrile;
(3SR,4RS)-[3-(3,4-dichloro-phenyl)-4-(5-trifluoromethyl-pyridin-2-ylsulfanylmethyl)-pyrrolidin-1-yl]-(4-methanesulfonyl-piperazin-1-yl)-methanone;
(3SR,4RS)-[3-(5-chloro-pyridin-2-ylsulfanylmethyl)-4-(3,4-dichloro-phenyl)-pyrrolidin-1-yl]-(4-methanesulfonyl-piperazin-1-yl)-methanone;
(3SR,4RS)-[3-(3,4-dichloro-phenyl)-4-[(5-nitro-pyridin-2-ylamino)-methyl]-pyrrolidin-1-yl]-(4-methanesulfonyl-piperazin-1-yl)-methanone;
(3SR,4RS)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone;
(3S,4S)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone;
(3R,4R)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone;
(3SR,4RS)-3-(3,4-dichloro-phenyl)-4-{[methyl-(5-trifluoromethyl-pyridin-2-yl)-amino]-methyl}-pyrrolidin-1-yl)-(4-methanesulfonyl-piperazin-1-yl)-methanone;
(3SR,4RS)-{3-(3,4-dichloro-phenyl)-4-[(4-trifluoromethyl-phenylamino)-methyl]-pyrrolidin-1-yl}-(4-methanesulfonyl-piperazin-1-yl)-methanone;
(3SR,4RS)-[3-[(5-chloro-pyridin-2-ylamino)-methyl]-4-(3,4-dichloro-phenyl)-pyrrolidin-1-yl]-(4-methanesulfonyl-piperazin-1-yl)-methanone;
(3SR,4RS)-2-{[4-(3,4-dichloro-phenyl)-1-(4-methanesulfonyl-piperazine-1-carbonyl)-pyrrolidin-3-ylmethyl]-amino}-pyrimidine-5-carbonitrile;
(3SR,4RS) 6-{1-(RS)-[4-(3,4-dichloro-phenyl)-1-(4-methanesulfonyl-piperazine-1-carbonyl)-pyrrolidin-3-yl]-ethylamino}-nicotinonitrile;
(3SR,4RS) 6-{1-(SR)-[4-(3,4-Dichloro-phenyl)-1-(4-methanesulfonyl-piperazine-1-carbonyl)-pyrrolidin-3-yl]-ethylamino}-nicotinonitrile;
(3SR,4RS) {3-(3,4-dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone;
(3SR,4RS) {3-(3,4-dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone; and
(3SR,4RS) {3-(3,4-dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone.

Further preferred are compounds of formula I-A, wherein

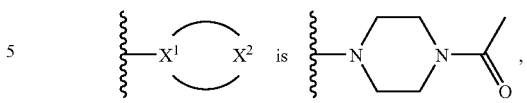

for example
(3SR,4RS)-1-(4-{-3-(3,4-dichloro-phenyl)-4-[(5-trifluoromethyl-pyridin-2-ylamino)-methyl]-pyrrolidine-1-carbonyl}-piperidin-1-yl)-ethanone;
(3SR,4RS)-{1-{4-[3-[(5-chloro-pyrimidin-2-ylamino)-methyl]-4-(3,4-dichloro-phenyl)-pyrrolidine-1-carbonyl]-piperidin-1-yl}-ethanone; and
(3SR,4RS) 1-(4-{3-(3,4-dichloro-phenyl)-4-[(5-trifluoromethyl-pyrimidin-2-ylamino)-methyl]-pyrrolidine-1-carbonyl}-piperidin-1-yl)-ethanone.

Further preferred are compounds of formula I-A, wherein

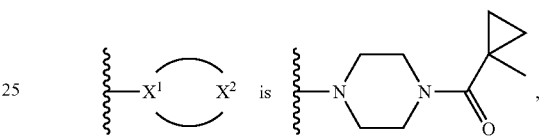

for example
(3SR,4RS)-(3-(3,4-dichloro-phenyl)-4-[(5-trifluoromethyl-pyridin-2-ylamino)-methyl]-pyrrolidine-1-carbonyl}-piperidin-1-yl)-(1-methyl-cyclopropyl)-methanone;
(3SR,4RS)-{3-[(5-chloro-pyrimidin-2-ylamino)-methyl]-4-(3,4-dichloro-phenyl)-pyrrolidin-1-yl]-[1-(1-methyl-cyclopropanecarbonyl)-piperidin-4-yl]-methanone;
(3SR,4RS) {3-(3,4-dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;
(3SR,4RS) {3-(4-chloro-phenyl)-4-[(5-chloro-pyridin-2-ylamino)-methyl]-pyrrolidin-1-yl}-[1-(1-methyl-cyclopropanecarbonyl)-piperidin-4-yl]-methanone;
(3SR,4RS) {3-(4-fluoro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;
(3SR,4RS) [4-(3-(4-fluoro-phenyl)-4-{[methyl-(5-trifluoromethyl-pyrimidin-2-yl)-amino]-methyl}-pyrrolidine-1-carbonyl)-piperidin-1-yl]-(1-methyl-cyclopropyl)-methanone;
6-({(3S,4S)-4-(4-chloro-phenyl)-1-[1-(1-methyl-cyclopropanecarbonyl)-piperidine-4-yl]-pyrrolidin-3-ylmethyl}-methyl-amino)-nicotinonitrile;
[4-((3S,4S)-3-(4-chloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone;
((3S,4S)-3-(4-chloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone;
{(3S,4S)-3-(3,4-dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;
((3S,4S)-3-(3,4-dichloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone;

[4-((3S,4S)-3-(3,4-dichloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone;

6-({(3S,4S)-4-(3,4-dichloro-phenyl)-1-[1-(1-methyl-cyclopropanecarbonyl)-piperidine-4-carbonyl]-pyrrolidin-3-ylmethyl}-methyl-amino)-nicotinonitrile; and {4-[(3S,4S)-3-{[(5-chloro-pyridin-2-yl)-methyl-amino]-methyl}-4-(3,4-dichloro-phenyl)-pyrrolidine-1-carbonyl]-piperidin-1-yl}-(1-methyl-cyclopropyl)-methanone.

Further preferred are compounds of formula I-B, wherein het-R$^{1'}$ is a six membered heteroaryl group, containing one or two N-atoms, for example (3SR,4RS)-5-{3-(3,4-dichloro-phenyl)-4-[(5-trifluoromethyl-pyridin-2-ylamino)-methyl]-pyrrolidine-1-carbonyl}-pyridine-2-carbonitrile;

(3SR,4RS)-{3-(3,4-dichloro-phenyl)-4-[(5-trifluoromethyl-pyridin-2-ylamino)-methyl]-pyrrolidin-1-yl}-(6-methyl-pyridazin-4-yl)-methanone;

(3SR,4RS)-{3-(3,4-dichloro-phenyl)-4-[(5-trifluoromethyl-pyridin-2-ylamino)-methyl]-pyrrolidin-1-yl}-pyridazin-4-yl-methanone;

(3SR,4RS)-{3-(3,4-dichloro-phenyl)-4-[(5-trifluoromethyl-pyridin-2-ylamino)-methyl]-pyrrolidin-1-yl}-(3,6-dimethyl-pyridazin-4-yl)-methanone;

(3SR,4RS)-{5-[3-[(5-chloro-pyrimidin-2-ylamino)-methyl]-4-(3,4-dichloro-phenyl)-pyrrolidine-1-carbonyl]-pyridine-2-carbonitrile;

(3SR,4RS)-[3-[(5-chloro-pyrimidin-2-ylamino)-methyl]-4-(3,4-dichloro-phenyl)-pyrrolidin-1-yl]-(6-methyl-pyridazin-4-yl)-methanone;

(3SR,4RS) {3-(3,4-dichloro-phenyl)-4-[(5-trifluoromethyl-pyrimidin-2-ylamino)-methyl]-pyrrolidin-1-yl}-(6-methyl-pyridazin-4-yl)-methanone;

{(3S,4S)-3-(3,4-dichloro-phenyl)-4-[(5-trifluoromethyl-pyrimidin-2-ylamino)-methyl]-pyrrolidin-1-yl}-(6-methyl-pyridazin-4-yl)-methanone; and ((3S,4S)-3-(3,4-dichloro-phenyl)-4-{[methyl-(5-trifluoromethyl-pyrimidin-2-yl)-amino]-methyl}-pyrrolidin-1-yl)-(6-methyl-pyridazin-4-yl)-methanone.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variant described below, which process comprises a) coupling a compound of formula

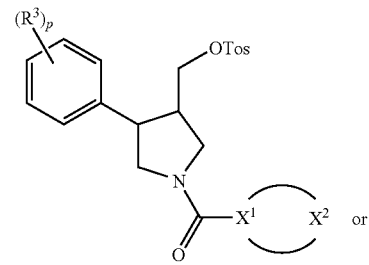

VIII

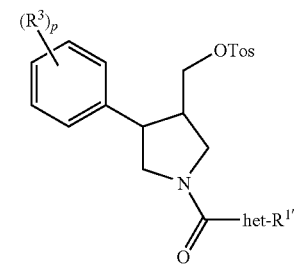

VIII-1 to produce a compound of formula

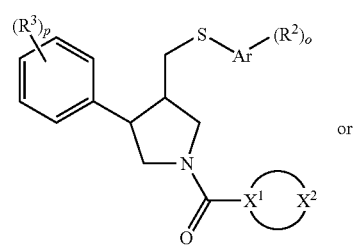

I-A1 or

I-B1

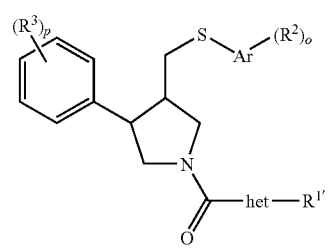

wherein the definitions are described above, or b) oxidizing a compound of formula

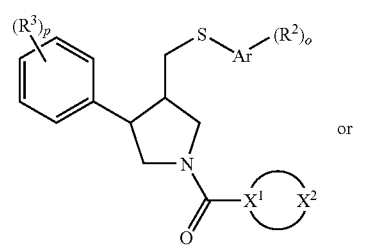

I-A1 or

-continued
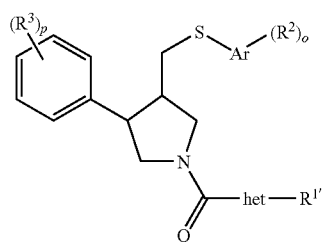
to produce a compound of formula
I-A2
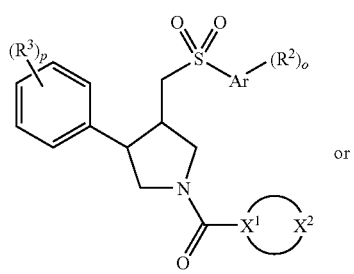
or
I-B2
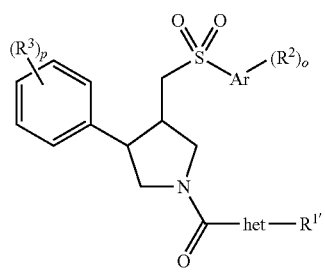
wherein the definitions are described above, or
c) coupling a compound of formula
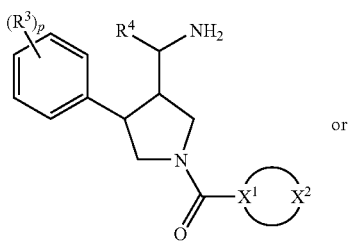
or
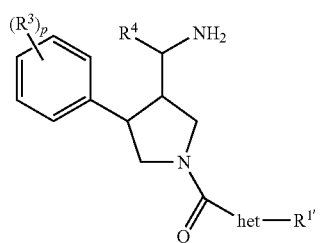
with hal-(R²)ₒ
to produce a compound of formula
I-B1
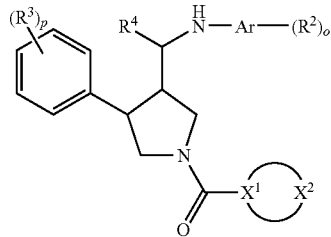
or
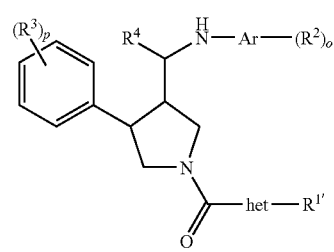
wherein the definitions are described above, or
d) coupling a compound of formula
XXXVIII
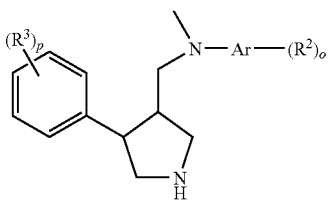
with a compound of formula
XXV
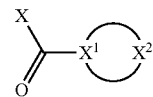
or X—C(O)-het-R¹'
to produce a compound of formula
XXV-1
I-A5
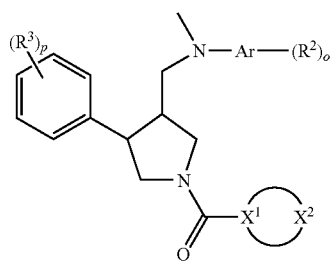
or

I-B5

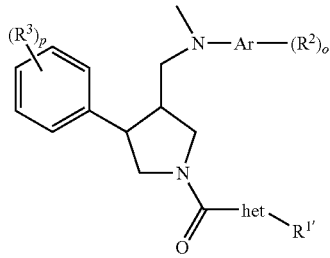

wherein the definitions are described above, and if desired, converting the compounds obtained into pharmaceutically acceptable acid addition salts.

The preparation of compounds of formula I is further described in more detail in general schemes I to IX and in examples 1-66.

General Procedure I

Amid Coupling (Pyrrolidine V, XI, XVI, XXII, XXX, XXXVI, XXXVIII, XLVII or LVI and Carboxylic Acid)

To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a corresponding pyrrolidine intermediate. The mixture was stirred at RT over night and then poured onto water and extracted with $CH_2Cl_2$. The combined organic phases were dried over $Na_2SO_4$ and concentrated under vacuo. Flash chromatography or preparative HPLC afforded the title compound.

General Procedure II

Coupling Between a Compound of Formula V, XI, XVI, XXII, XXX, XXXVI, XXXVIII, XLVII or LVI and an Acid Chloride or Carbamoyl Chloride A solution of the pyrrolidine (1 mmol) of formula (v.s.) in $CH_2Cl_2$ (10 mL) was treated with $Et_3N$ (1.2 mmol) and an acid chloride or carbamoyl chloride (1.2 mmol) and stirred at RT overnight. The reaction mixture was then poured onto water and extracted with $CH_2Cl_2$. The combined organic phases were dried over $Na_2SO_4$ and concentrated under vacuo. Purification by preparative HPLC yielded the title compound.

General Procedure III

Nucleophilic Substitution Reaction: Coupling Between a Compound of Formula VIII with Thiophenyl and Thiopyridone To a stirred solution of tosylate VIII (1 mmol) and potassium carbonate (3 mmol) in DMF (5 mL) at RT were added a thiophenol derivative (3 mmol). Stirring was continued for 1.5 h at 100° C. The reaction mixture was washed with $H_2O$ and the organic phase was dried over $Na_2SO_4$. Column chromatography yielded the title compound.

General procedure IV

Nucleophilic Aromatic Substitution Reaction: Coupling a Compound of Formula XIII with Heteroaromatic Chlorides and/or Methylsulfones A solution of amine XIII or XIV (1 mmol), triethylamine (0.4 mL, 2 mmol) and a heteroaromatic chloride (1 mmol) in DMSO (0.5 mL) in a high pressure glass vial is heated at 150-160° C. for several hours, depending on the nature of the compound. After the reaction ran to completion it was diluted with water, extracted with ethyl acetate and the combined organic phases were dried over sodium sulfate. Column chromatography yielded the title compound.

General Procedure V

Cleavage of the N-Benzyl Group with 1-chloroethylchloroformat and Methanol

N-Benzyl pyrrolidine derivatives (2 mmol) were dissolved in toluene (10 mL) and treated with $NEt(iProp)_2$ (6 mmol) and 1-chloroethylchloroformat (6 mmol) at 100° C. for 1.5 h. The solvent was evaporated, the residue taken up in MeOH (15 mL) and heated to reflux for 3 h. After evaporation of the solvent the residue was subjected to column chromatography to yield the de-benzylated product.

General Procedure VI

Nucleophilic Substitution Reaction: Coupling a Compound of Formula XIX with Anilines and Heteroaromatic Amines To a stirred solution of tosylate XIX (1 mmol) and potassium carbonate (3 mmol) in DMF (5 mL) at RT were added an anilin derivative of formula (3 mmol). Stirring was continued for several hours, depending on the nature of the aniline derivative, at 120° C. The solvent was evaporated and the residue taken up in ethyl acetate. After washing with $H_2O$ the organic phase was dried over $Na_2SO_4$, filtered and concentrated. Column chromatography of the residue yielded the title compound.

Scheme 1
Preparation of derivatives of formula I-A or I-B, wherein A is S, SO or $SO_2$

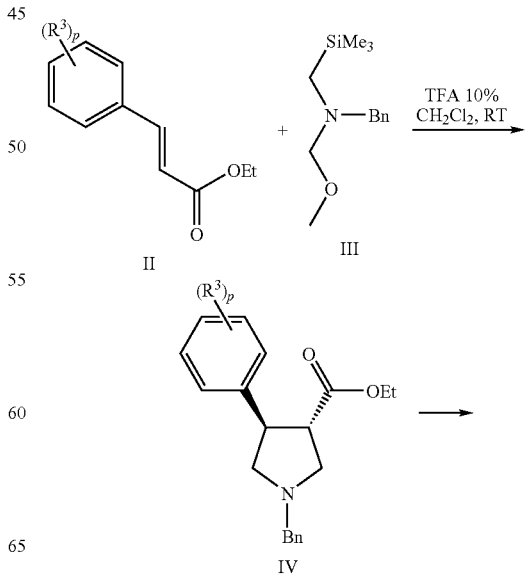

-continued

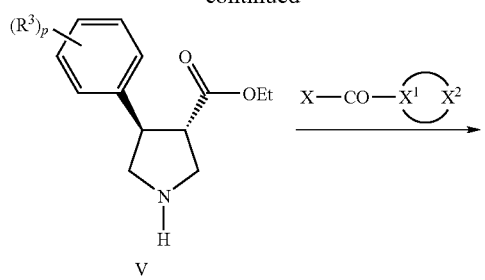

V

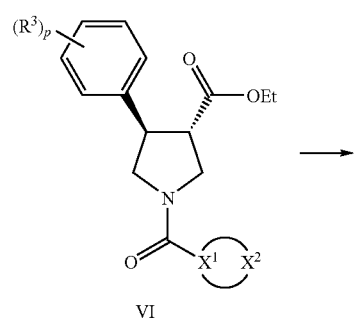

VI

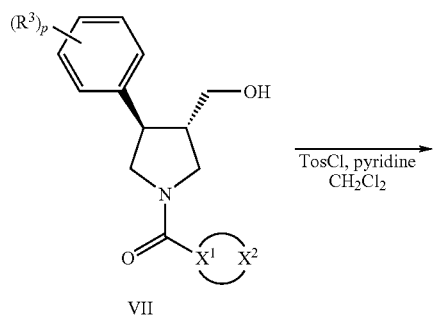

TosCl, pyridine
CH₂Cl₂

VII

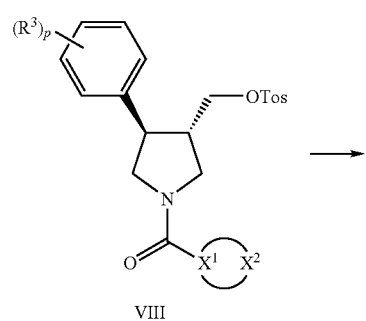

VIII

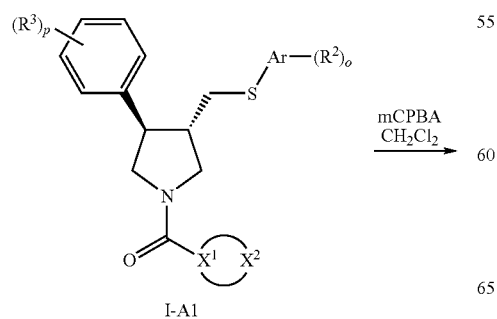

mCPBA
CH₂Cl₂

I-A1

-continued

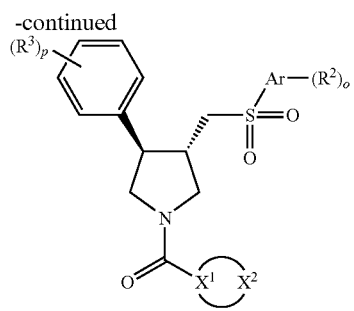

I-A2 ditto for:

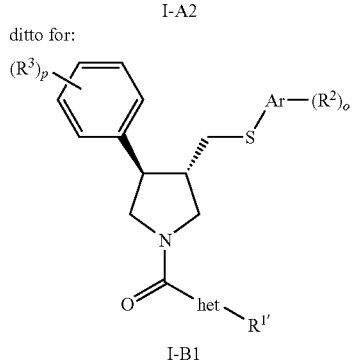

I-B1

X is halogen and the other definitions are as described above.

The 3,4-disubstituted pyrrolidines IV were prepared via a stereo specific 1,3-dipolar cycloaddition between the (E)-3-substituted phenyl-acrylic acid ethyl ester derivatives II and the azomethine glide generated in situ from the N-(methoxymethyl)-N-(phenylmethyl)-N-(trimethylsilyl)methylamine III in the presence of a catalytic amount of acid, such as TFA. Selective N-debenzylation was then carried out using several known procedures which are compatible with the substitution patterns of the aromatic ring to afford V. A coupling with a suitable acid chloride, carboxylic acid or carbamoyl chloride using known methods gave VI. Reduction of the ester moiety using standard conditions for example LiBH₄ yielded the alcohol VII. Reaction with p-toluolsulfonyl chloride gave the tosylat VIII which was then displaced by thiophenol derivatives and if desired oxidized with mCPBA to yield sulfones.

Pyrrolidine Intermediates of Formula VIII

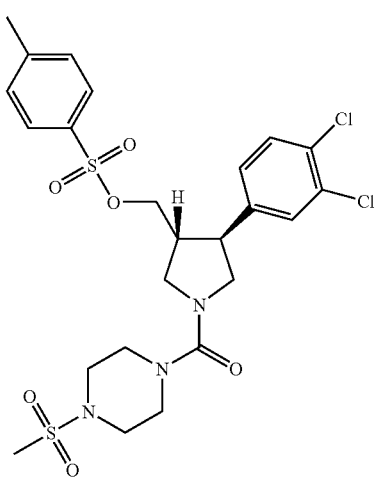

a) (3SR,4RS)-1-Benzyl-4-(3,4-dichloro-phenyl)-pyrrolidine-3-carboxylic acid ethyl ester A solution of N-(methoxymethyl)-N-(phenylmethyl)-N-(trimethylsilyl)methylamine (2.46 g, 10.4 mmol) in $CH_2Cl_2$ (15 mL) was added dropwise, over a 30 minutes period, to a stirred solution of (E)-3-(3,4-dichloro-phenyl)-acrylic acid ethyl ester (2.40 g, 10.4 mmol) and trifluoroacetic acid (0.08 mL, 1 mmol) in $CH_2Cl_2$ (10 mL) at 0° C. The ice bath was removed and the solution was stirred at 25° C. for an additional 48 h. It was then concentrated and purification by flash chromatography ($SiO_2$, EtOAc/heptane 1:4) afforded 2.48 g (66%) of the title compound as a yellow oil. ES-MS m/e: 379.3 (M+H$^+$).

b) (3SR,4RS)-4-(3,4-Dichloro-phenyl)-pyrrolidine-3-carboxylic acid ethyl ester To a solution of (3SR,4RS)-1-benzyl-4-(3,4-dichloro-phenyl)-pyrrolidine-3-carboxylic acid ethyl ester (2.50 g, 6.61 mmol) in $CH_3CN$ (55 mL) was added 2,2,2-trichloroethyl chloroformate (1.34 mL, 9.91 mmol) and stirring was continued for 4 hours at RT. Volatiles were removed under vacuo, and the residue was dissolved in AcOH (25 mL). Then Zn dust (1.20 g) was added portion wise. After three hours at RT the reaction mixture was filtered on celite, the solvent removed under vacuo followed by an extraction with EtOAc/aq. $NaHCO_3$ (basic pH). The organic phases were dried on $Na_2SO_4$ and column chromatography ($SiO_2$, $CH_2Cl_2$/MeOH 9:1) yielded 1.85 g (97%) of the title compound as a light yellow oil. ES-MS m/e: 288.1 (M+H$^+$).

c) (3SR,4RS)-4-(3,4-Dichloro-phenyl)-1-(4-methanesulfonyl-piperazine-1-carbonyl)-pyrrolidine-3-carboxylic acid ethyl ester Using the general procedure II, the coupling between (3SR,4RS)-4-(3,4-dichloro-phenyl)-pyrrolidine-3-carboxylic acid ethyl ester (1.89 g, 6.55 mmol) and 4-methanesulfonyl-piperazine-1-carbonyl chloride (1.63 g, 7.2 mmol) (CAS-RN: 65463-96-9) yielded the title product (2.40 g, 77%) as a colorless oil after purification by flash chromatography ($SiO_2$, EtOAc). ES-MS m/e: 478.1 (M+H$^+$).

d) [(3RS,4SR)-3-(3,4-Dichloro-phenyl)-4-hydroxymethyl-pyrrolidin-1-yl]-(4-methanesulfonyl-piperazin-1-yl)-methanone To a stirred solution of (3SR,4RS)-4-(3,4-dichloro-phenyl)-1-(4-methanesulfonyl-piperazine-1-carbonyl)-pyrrolidine-3-carboxylic acid ethyl ester (2.39 g, 5.00 mmol) in MeOH (80 mL) at RT was added $LiBH_4$ (434 mg, 19.9 mmol). After 2 hours a second portion of $LiBH_4$ (1.30 g, 59.7 mmol) was added and stirring was continued for 2 days. The reaction mixture was poured on $H_2O$, extracted with EtOAc and the combined organic phases were dried over $Na_2SO_4$. Flash chromatography ($SiO_2$, EtOAc, then EtOAc/MeOH 9:1) yielded the title product (1.76 g, 81%) as a white solid. ES-MS m/e: 436.1 (M+H$^+$).

e) Toluene-4-sulfonic acid (3SR,4RS)-4-(3,4-dichloro-phenyl)-1-(4-methanesulfonyl-piperazine-1-carbonyl)-pyrrolidin-3-ylmethyl ester To a solution of (3SR,4RS)-3-(3,4-dichloro-phenyl)-4-hydroxymethyl-pyrrolidin-1-yl]-(4-methanesulfonyl-piperazin-1-yl)-methanone (0.70 g, 2.0 mmol) in tetrahydrofuran (10 mL) was added p-tolylsulfonyl chloride (0.46 g, 2.0 mmol) and triethylamin (0.6 mL, 4.0 mmol). The reaction mixture was stirred over night at 60° C. Volatiles were removed under vacuo and the residue was subjected to column flash chromatography ($SiO_2$, EtOAc/heptane 1:1, then EtOAc) to yield the title product (0.37 g, 39%) as a white solid. ES-MS m/e: 591.1 (M+H$^+$).

EXAMPLE 1

(3SR,4RS)-[3-(3,4-Dichloro-phenyl)-4-(4-trifluoromethyl-phenylsulfanylmethyl)-pyrrolidin-1-yl]-(4-methanesulfonyl-piperazin-1-yl)-methanone

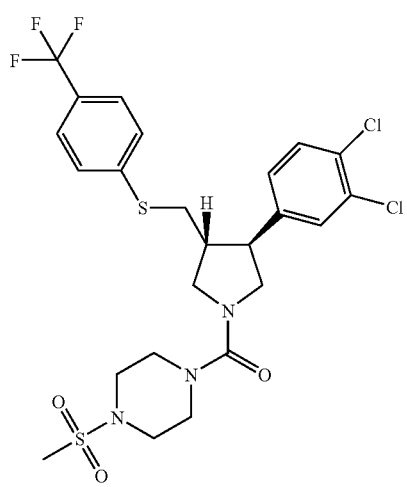

Nucleophilic substitution according to General Procedure III:
Tosylate: toluene-4-sulfonic acid (3SR,4RS)-4-(3,4-dichloro-phenyl)-1-(4-methanesulfonyl-piperazine-1-carbonyl)-pyrrolidin-3-ylmethyl ester
Thiophenol: 4-(trifluoromethyl)thiophenol
ES-MS m/e: 596.2 (M+H$^+$).

EXAMPLE 2

(3SR,4RS)-[3-(4-(4-Chloro-phenylsulfanylmethyl)-4-(3,4-dichloro-phenyl)-pyrrolidin-1-yl]-(4-methanesulfonyl-piperazin-1-yl)-methanone

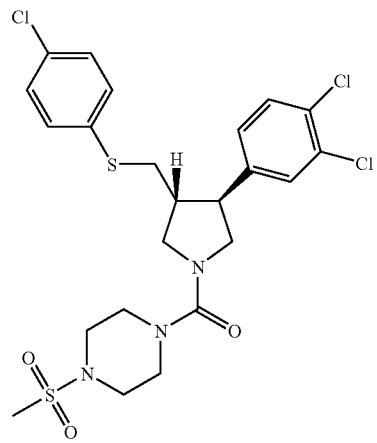

Nucleophilic substitution according to General Procedure III:
Tosylate: toluene-4-sulfonic acid (3SR,4RS)-4-(3,4-dichloro-phenyl)-1-(4-methanesulfonyl-piperazine-1-carbonyl)-pyrrolidin-3-ylmethyl ester
Thiophenol: 4-chlorothiophenol
ES-MS m/e: 564.1 (M+H⁺).

EXAMPLE 3

(3SR,4RS)-[3-(4-Chloro-phenylsulfanylmethyl)-4-(3,4-dichloro-phenyl)-pyrrolidin-1-yl]-(4-methanesulfonyl-piperazin-1-yl)-methanone

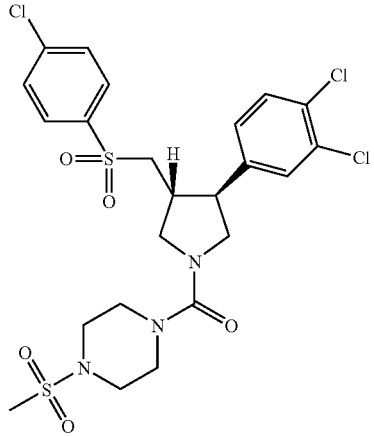

To a solution of toluene-4-sulfonic acid (3SR,4RS)-4-(3,4-dichloro-phenyl)-1-(4-methanesulfonyl-piperazine-1-carbonyl)-pyrrolidin-3-ylmethyl ester (0.05 g, 0.09 mmol) in $CH_2Cl_2$ (2 mL) was added m-CPBA (0.046 g, 0.19 mmol) at 0° C. The reaction mixture was stirred for 2 h at 0° C. Sodium carbonate (20% in $H_2O$) was added and it was extracted with $CH_2Cl_2$ (3×10 mL). The combined organic phases were dried on sodium sulfate, filtered and the volatiles were removed under vacuo. The residue was subjected to column flash chromatography ($SiO_2$, EtOAc) to yield the title product (0.035 g, 66%) as a colorless foam. ES-MS m/e: 595.9 (M+H⁺).

EXAMPLE 4

(3SR,4RS)-4-[4-(3,4-Dichloro-phenyl)-1-(4-methanesulfonyl-piperazine-1-carbonyl)-pyrrolidin-3-ylmethylsulfanyl]-benzonitrile

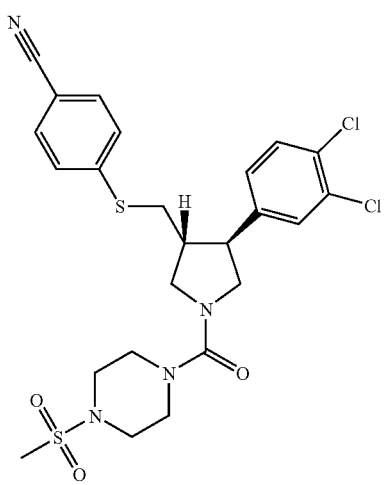

Nucleophilic substitution according to General Procedure III:
Tosylate: toluene-4-sulfonic acid (3SR,4RS)-4-(3,4-dichloro-phenyl)-1-(4-methanesulfonyl-piperazine-1-carbonyl)-pyrrolidin-3-ylmethyl ester
Thiophenol: 4-cyanothiophenol
ES-MS m/e: 553.2 (M+H⁺).

EXAMPLE 5

(3SR,4RS)-[3-(3,4-Dichloro-phenyl)-4-(5-trifluoromethyl-pyridin-2-ylsulfanylmethyl)-pyrrolidin-1-yl]-(4-methanesulfonyl-piperazin-1-yl)-methanone

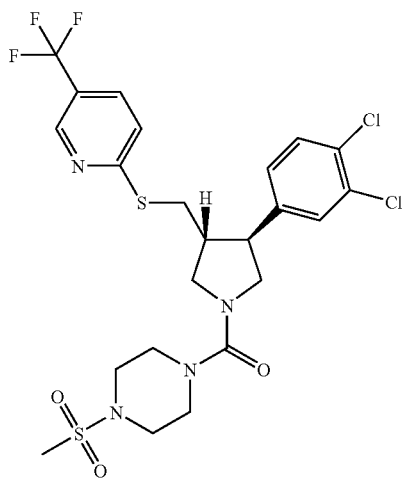

Nucleophilic substitution according to General Procedure III:
Tosylate: toluene-4-sulfonic acid (3SR,4RS)-4-(3,4-dichloro-phenyl)-1-(4-methanesulfonyl-piperazine-1-carbonyl)-pyrrolidin-3-ylmethyl ester
2-Mercapto-5-(trifluoromethyl)pyridine
ES-MS m/e: 597.2 (M+H⁺).

EXAMPLE 6

(3SR,4RS)-[3-(5-Chloro-pyridin-2-ylsulfanylmethyl)-4-(3,4-dichloro-phenyl)-pyrrolidin-1-yl]-(4-methanesulfonyl-piperazin-1-yl)-methanone

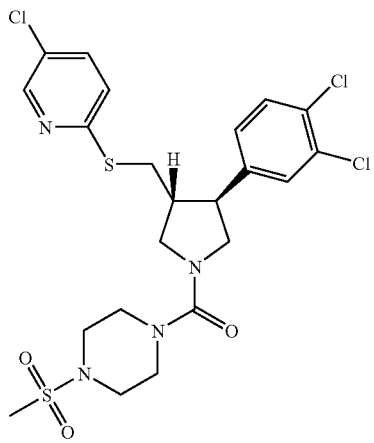

Nucleophilic substitution according to General Procedure III:

Tosylate: toluene-4-sulfonic acid (3SR,4RS)-4-(3,4-dichloro-phenyl)-1-(4-methanesulfonyl-piperazine-1-carbonyl)-pyrrolidin-3-ylmethyl ester 5-Chlorpyridin-2-thiol ES-MS m/e: 563.0 (M+H$^+$).

Scheme 2:
Preparation of derivatives of formula XIII wherein A is NH-cyano approach I

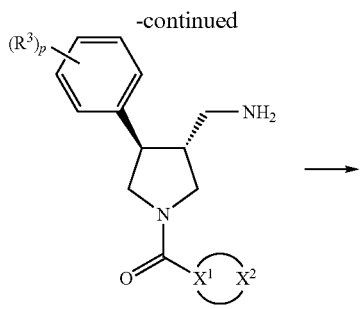

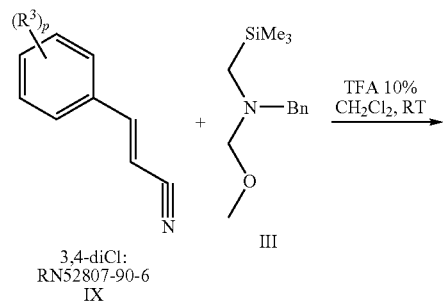

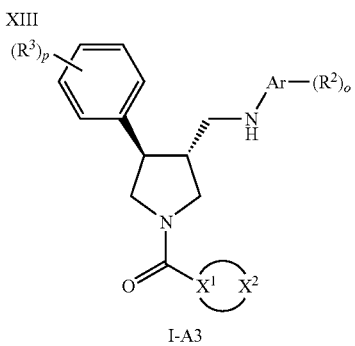

wherein (R$^3$)$_p$ is 3,4-di-Cl and the other substituents are as described above.

Pyrrolidine Intermediates of Formula XIII

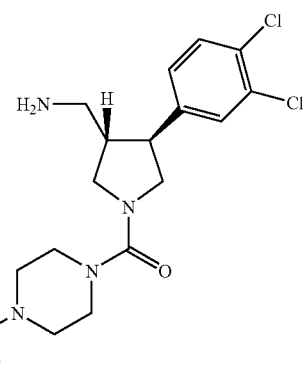

a) (3SR,4RS)-1-Benzyl-4-(3,4-dichloro-phenyl)-pyrrolidine-3-carbonitrile

A solution of N-(methoxymethyl)-N-(phenylmethyl)-N-(trimethylsilyl)methylamine (10.25 g, 43 mmol) in CH$_2$Cl$_2$ (55 mL) was added dropwise, over a 30 minutes period, to a stirred solution of (E)-3-(3,4-dichloro-phenyl)-acrylnitrile (5.70 g, 29 mmol) and trifluoroacetic acid (0.22 mL, 3 mmol) in CH$_2$Cl$_2$ (10 mL) at 0° C. The ice bath was removed, and the solution was stirred at 25° C. for an additional 48 h. It was then concentrated and purification by flash chromatography (SiO$_2$, CH$_2$Cl$_2$) afforded the title compound (7.0 g, 73%) as a colorless oil. ES-MS m/e: 332.3 (M+H$^+$).

b) (3SR,4RS)-4-(3,4-Dichloro-phenyl)-pyrrolidine-3-carbonitrile

To a solution of (3SR,4RS)-1-benzyl-4-(3,4-dichloro-phenyl)-pyrrolidine-3-carbonitrile (2.0 g, 6.6 mmol) dissolved in CH$_3$CN (30 mL) was added 2,2,2-trichloroethyl chloroformate (1.22 mL, 9.91 mmol) and stirring was continued for 4 hours at RT. Volatiles were removed under vacuo, and the

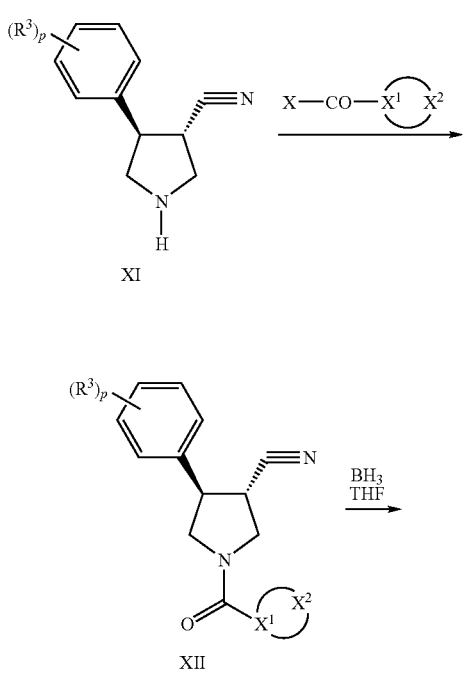

residue was dissolved in AcOH (25 mL) before a total of 1.20 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and the crude reaction product obtained used in the next reaction step, yielding 0.6 g (55%) of the title compound as a light yellow oil. ES-MS m/e: 242.1 (M+H$^+$).

c) (3SR,4RS)-4-(3,4-Dichloro-phenyl)-1-(4-methanesulfonyl-piperazine-1-carbonyl)-pyrrolidine-3-carbonitrile Using the general procedure II, the coupling between (3SR,4RS)-4-(3,4-dichloro-phenyl)-pyrrolidine-3-carbonitrile (0.60 g, 2.0 mmol) and 4-methanesulfonyl-piperazine-1-carbonyl chloride (0.63 g, 2.7 mmol) (CAS-RN 65463-96-9) yielded the title product (0.68 g, 63%) as a light yellow foam after purification by flash chromatography (SiO$_2$, EtOAc/heptane 1:1). ES-MS m/e: 432.1 (M+H$^+$).

d) [(3RS,4SR)-[3-Aminomethyl-4-(3,4-dichloro-phenyl)-pyrrolidin-1-yl]-(4-methanesulfonyl-piperazin-1-yl)-methanone To a stirred solution of (3SR,4RS)-4-(3,4-Dichloro-phenyl)-1-(4-methanesulfonyl-piperazine-1-carbonyl)-pyrrolidine-3-carbonitrile (0.1 g, 0.23 mmol) in tetrahydrofuran (1.0 mL) at 0° C. was added BH$_3$ in tetrahydrofuran (0.55 mL, 0.55 mmol). After 2 hours of stirring at ambient temperature the reaction mixture was quenched with MeOH and the volatiles were removed under vacuo. The residue was taken up in H$_2$O, extracted with EtOAc and the combined organic phases were dried over Na$_2$SO$_4$. Flash chromatography (SiO$_2$, EtOAc, then CH$_2$Cl$_2$/MeOH 19:1) yielded the title product (0.57 g, 56%) as a colorless oil. ES-MS m/e: 436.1 (M+H$^+$).

EXAMPLE 7

(3SR,4RS)-[3-(3,4-Dichloro-phenyl)-4-[(5-nitro-pyridin-2-ylamino)-methyl]-pyrrolidin-1-yl]-(4-methanesulfonyl-piperazin-1-yl)-methanone

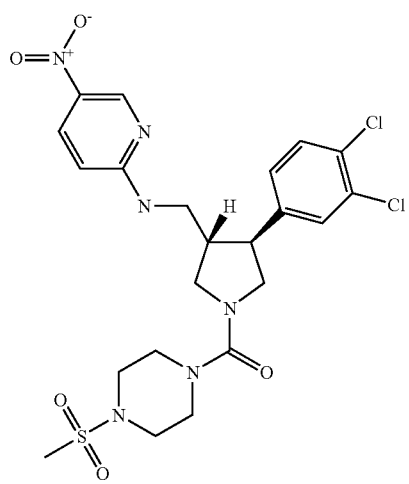

Nucleophilic aromatic substitution according to General Procedure IV:
Amine: [(3RS,4SR)-[3-Aminomethyl-4-(3,4-dichloro-phenyl)-pyrrolidin-1-yl]-(4-methanesulfonyl-piperazin-1-yl)-methanone
Heteroaromatic chloride: 2-Chloro-4-nitropyridine
ES-MS m/e: 557.2 (M+H$^+$).

EXAMPLE 8

(3SR,4RS)-[3-(3,4-Dichloro-phenyl)-4-[(5-nitro-pyridin-2-ylamino)-methyl]-pyrrolidin-1-yl]-(4-methanesulfonyl-piperazin-1-yl)-methanone

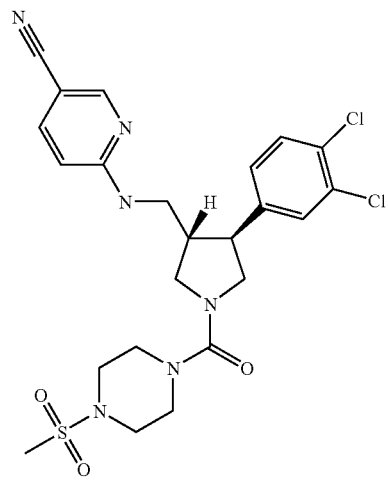

Nucleophilic aromatic substitution according to General Procedure IV:
Amine: [(3RS,4SR)-[3-Aminomethyl-4-(3,4-dichloro-phenyl)-pyrrolidin-1-yl]-(4-methanesulfonyl-piperazin-1-yl)-methanone
Heteroaromatic chloride: 2-Chloro-4-cyanopyridine
ES-MS m/e: 536.9 (M+H$^+$).

Scheme 3:
Preparartion of drivatives of formula XIV wherein a is NH-cyano approach II

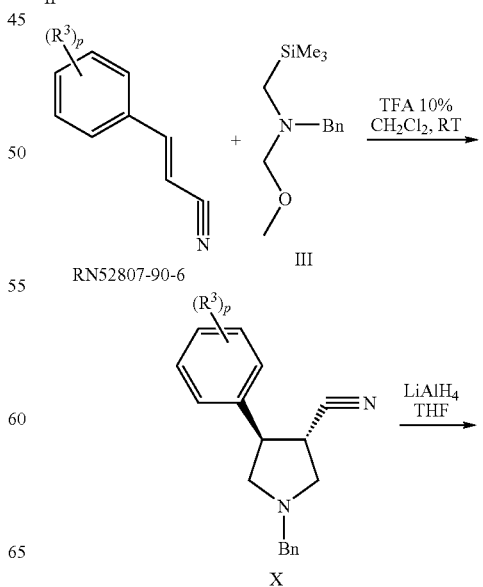

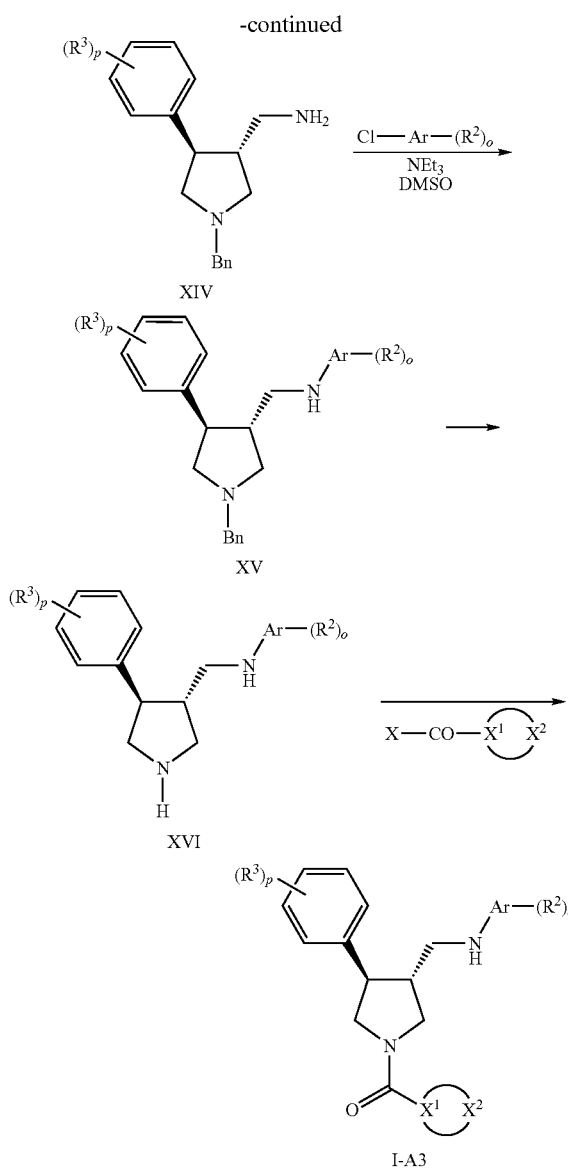

wherein (R³)ₚ is 3,4-di-Cl and the other substituents are as described above.

Pyrrolidine Intermediates of Formula XIV

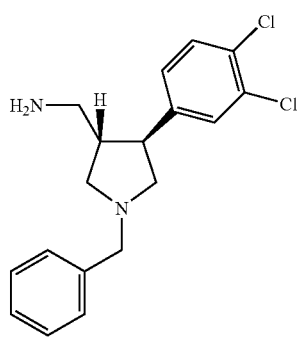

[(3RS,4SR)-[1-Benzyl-4-(3,4-dichloro-phenyl)-pyrrolidin-3-yl]-methylamine

To a stirred solution of (3SR,4RS)-1-benzyl-4-(3,4-dichloro-phenyl)-pyrrolidine-3-carbonitrile (13 g, 0.39 mol) in tetrahydrofuran (250 mL) at 0° C. was added portion-wise LiAlH₄ (1.56 g, 0.41 mol). After 2 hours of stirring at 0° C. the reaction mixture was quenched with water (50 mL) and 5N aqueous NaOH (12 mL) and stirred 30 min. The residue was extracted with EtOAc and the combined organic phases were dried over Na₂SO₄, filtered and the volatiles removed under vacuo to yield the crude title product (12.5 g, 95%) as a yellow oil which was used directly in the next reaction steps. ES-MS m/e: 336.4 (M+H⁺).

EXAMPLE 9

(3SR,4RS)-[1-(4-{3-(3,4-Dichloro-phenyl)-4-[(5-fluoro-pyrimidin-2-ylamino)-methyl]-pyrrolidine-1-carbonyl}-piperidin-1-yl)-ethanone

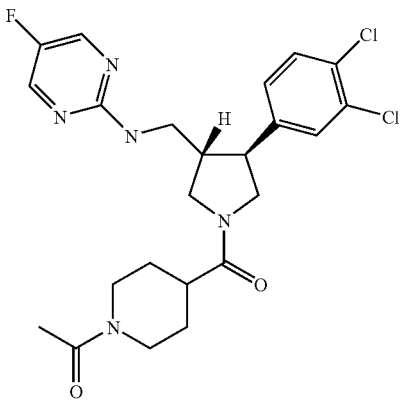

(3SR,4RS)-[1-Benzyl-4-(3,4-dichloro-phenyl)-pyrrolidin-3-ylmethyl]-(5-fluoro-pyrimidin-2-yl)-amine Nucleophilic aromatic substitution according to General Procedure IV:
Amine: [(3RS,4SR)-[1-Benzyl-4-(3,4-dichloro-phenyl)-pyrrolidin-3-yl]-methylamine
Heteroaromatic chloride: 2-Chloro-4-fluoropyrimidine
ES-MS m/e: 432.5 (M+H⁺).

b) (3SR,4RS)-[4-(3,4-Dichloro-phenyl)-pyrrolidin-3-ylmethyl]-(5-fluoro-pyrimidin-2-yl)-amine N-Benzyl cleavage according to General Procedure V:
N-Benzyl derivative: (3SR,4RS)-[1-Benzyl-4-(3,4-dichloro-phenyl)-pyrrolidin-3-ylmethyl]-(5-fluoro-pyrimidin-2-yl)-amine
ES-MS m/e: 342.4 (M+H⁺).

c) (3SR,4RS)-[1-(4-{3-(3,4-Dichloro-phenyl)-4-[(5-fluoro-pyrimidin-2-ylamino)-methyl]-pyrrolidine-1-carbonyl}-piperidin-1-yl)-ethanone Coupling between a compound of formula XVI and an acid chloride or carbamoyl chloride according to General procedure II
Amine: (3SR,4RS)-[4-(3,4-Dichloro-phenyl)-pyrrolidin-3-ylmethyl]-(5-fluoro-pyrimidin-2-yl)-amine
Acid chloride: 1-Acetylisonicopecotoylchloride
ES-MS m/e: 494.2 (M+H⁺).

EXAMPLE 10

(3SR,4RS)-5-{3-(3,4-Dichloro-phenyl)-4-[(5-fluoro-pyrimidin-2-ylamino)-methyl]-pyrrolidine-1-carbonyl}-pyridine-2-carbonitrile

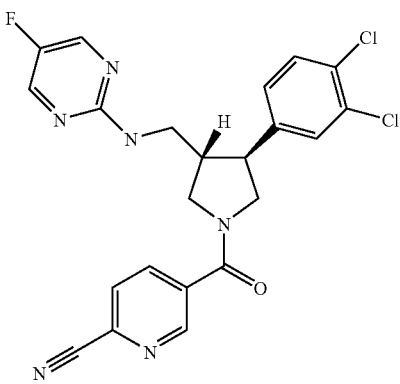

Amid Coupling according to General procedure I
Amine: (3SR,4RS)-[4-(3,4-Dichloro-phenyl)-pyrrolidin-3-ylmethyl]-(5-fluoro-pyrimidin-2-yl)-amine
Acid: 6-Cyanonicotinic acid
ES-MS m/e: 471.2 (M+H$^+$).

EXAMPLE 11

(3SR,4RS)-1-(4-{3-(3,4-Dichloro-phenyl)-4-[(6-trifluoromethyl-pyrimidin-4-ylamino)-methyl]-pyrrolidine-1-carbonyl}-piperidin-1-yl)-ethanone

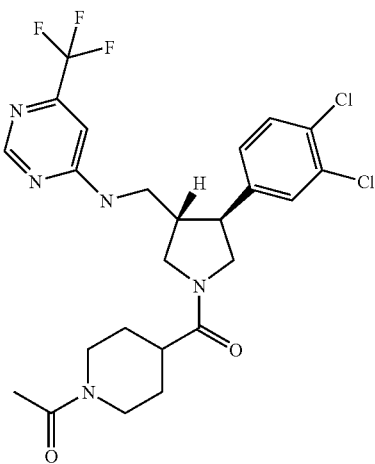

(3SR,4RS)-[1-Benzyl-4-(3,4-dichloro-phenyl)-pyrrolidin-3-ylmethyl]-(6-trifluoromethyl-pyrimidin-4-yl)-amine Nucleophilic aromatic substitution according to General Procedure IV:
Amine: [(3RS,4SR)-[1-Benzyl-4-(3,4-dichloro-phenyl)-pyrrolidin-3-yl]-methylamine
Heteroaromatic chloride: 4-Chloro-6-trifluoromethylpyrimidin (CAS RN: 37552-81-1)
ES-MS m/e: 482.5 (M+H$^+$).

b) (3SR,4RS)-[4-(3,4-Dichloro-phenyl)-pyrrolidin-3-ylmethyl]-(6-trifluoromethyl-pyrimidin-4-yl)-amine N-Benzyl cleavage according to General Procedure V:
N-Benzyl derivative: (3SR,4RS)-[1-Benzyl-4-(3,4-dichloro-phenyl)-pyrrolidin-3-ylmethyl]-(6-trifluoromethyl-pyrimidin-4-yl)-amine
ES-MS m/e: 392.4 (M+H$^+$).

c) (3SR,4RS)-[1-(4-{3-(3,4-Dichloro-phenyl)-4-[(6-trifluoromethyl-pyrimidin-4-ylamino)-methyl]-pyrrolidine-1-carbonyl}-piperidin-1-yl)-ethanone Coupling between a compound of formula XVI and an acid chloride or carbamoyl chloride according to General procedure II
Amine: (3SR,4RS)-[4-(3,4-Dichloro-phenyl)-pyrrolidin-3-ylmethyl]-(6-trifluoromethyl-pyrimidin-4-yl)-amine
Acid chloride: 1-Acetylisonicopecotoylchloride
ES-MS m/e: 544.1 (M+H$^+$).

EXAMPLE 12

(3SR,4RS)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone

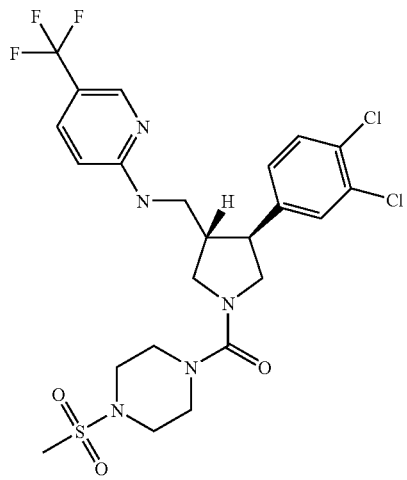

a) (3SR,4RS)-[1-Benzyl-4-(3,4-dichloro-phenyl)-pyrrolidin-3-ylmethyl]-(5-trifluoromethyl-pyridin-2-yl)-amine Nucleophilic aromatic substitution according to General Procedure IV:
Amine: [(3RS,4SR)-[1-Benzyl-4-(3,4-dichloro-phenyl)-pyrrolidin-3-yl]-methylamine
Heteroaromatic chloride: 2-Chloro-5-trifluoromethylpyridine (CAS RN: 52334-81-3)
ES-MS m/e: 481.5 (M-41).

b) (3SR,4RS)-[4-(3,4-Dichloro-phenyl)-pyrrolidin-3-ylmethyl]-(5-trifluoromethyl-pyridin-2-yl)-amine N-Benzyl cleavage according to General Procedure V:
N-Benzyl derivative: (3SR,4RS)-[1-Benzyl-4-(3,4-dichloro-phenyl)-pyrrolidin-3-ylmethyl]-(5-trifluoromethyl-pyridin-2-yl)-amine
ES-MS m/e: 391.4 (M+H$^+$).

c) (3SR,4RS)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone Coupling between a compound of formula XVI and an acid chloride or carbamoyl chloride according to General procedure II
Amine: (3SR,4RS)-[4-(3,4-Dichloro-phenyl)-pyrrolidin-3-ylmethyl]-(5-trifluoromethyl-pyridin-2-yl)-amine
Carbamoyl chloride: 4-Methanesulfonyl-piperazine-1-carbonyl chloride (CAS-RN 65463-96-9)
ES-MS m/e: 579.6 (M+H⁺).

EXAMPLE 13

(3S,4S)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone (3SR,4RS)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone (150 mg) were separated (HPLC, Chiralpak AD column, 30% iPrOH in heptane) to yield the title compound as a colorless foam (1.fraction eluted).
ES-MS m/e: 580.2 (M+⁺)

EXAMPLE 14

(3R,4R)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone (3SR,4RS)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone (150 mg) were separated (HPLC, Chiralpak AD column, 30% iPrOH in heptane) to yield the title compound as a colorless foam (2.fraction eluted).
ES-MS m/e: 580.2 (M+H⁺)

EXAMPLE 15

(3SR,4RS)-3-(3,4-Dichloro-phenyl)-4-{[methyl-(5-trifluoromethyl-pyridin-2-yl)-amino]-methyl}-pyrrolidin-1-yl)-(4-methanesulfonyl-piperazin-1-yl)-methanone

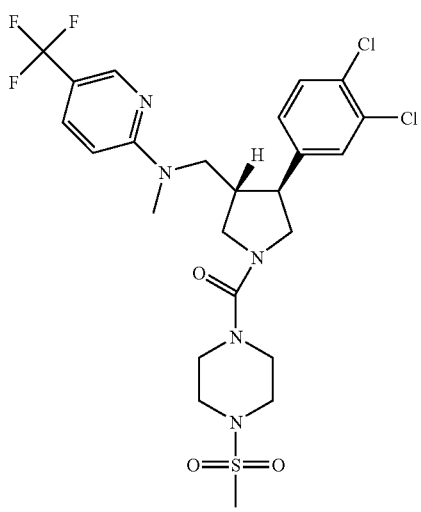

(3SR,4RS)-{3-(3,4-Dichloro-phenyl)-4-[(5-trifluoromethyl-pyridin-2-ylamino)-methyl]-pyrrolidin-1-yl}-(4-methanesulfonyl-piperazin-1-yl)-methanone (75 mg, 0.13 mmol) were dissolved in DMF (2 mL) and treated with NaH (55% dispersion in oil) (6.0 mg, 0.14 mmol) at ambient temperature. After 5 min methyl iodide (0.01 mL, 0.14 mmol) was added and the reaction mixture was stirred over night. After quenching with water and extraction with ethyl acetate (3×10 mL) the combined organic phases were dried on sodium sulfate and filtered. After evaporation of the solvent the crude product was subjected to column chromatography (silica gel, ethyl acetate) to yield the title product (66%) as a light yellow oil. ES-MS m/e: 594.2 (M+H⁺).

EXAMPLE 16

(3SR,4RS)-{3-(3,4-Dichloro-phenyl)-4-[(5-trifluoromethyl-pyridin-2-ylamino)-methyl]-pyrrolidin-1-yl}-(2-methyl-pyrimidin-5-yl)-methanone

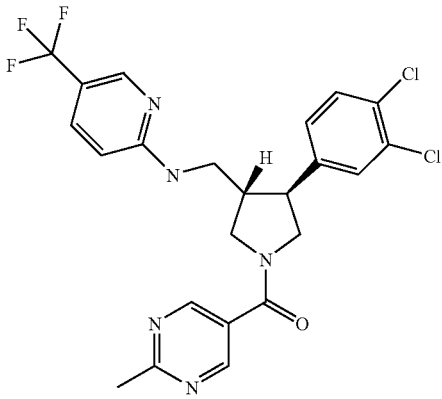

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 2-Methylpyrimidin-5-carboxylic acid
ES-MS m/e: 510.1 (M+H⁺).

EXAMPLE 17

(3SR,4RS)-5-{3-(3,4-Dichloro-phenyl)-4-[(5-trifluoromethyl-pyridin-2-ylamino)-methyl]-pyrrolidine-1-carbonyl}-pyridine-2-carbonitrile

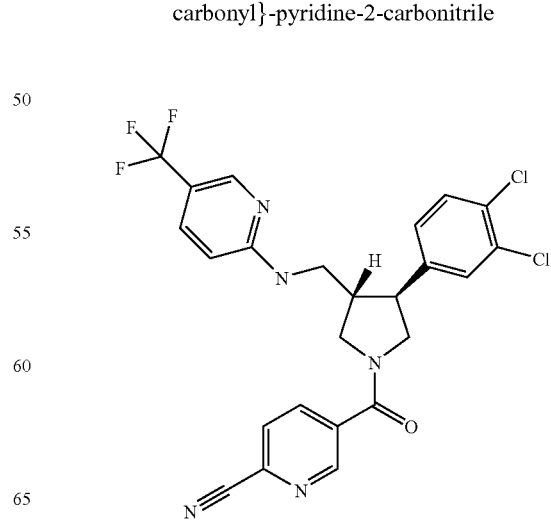

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 6-Cyanopyridin-3-carboxylic acid
ES-MS m/e: 520.2 (M+H⁺).

EXAMPLE 18

(3SR,4RS)-{3-(3,4-Dichloro-phenyl)-4-[(5-trifluoromethyl-pyridin-2-ylamino)-methyl]-pyrrolidin-1-yl}-pyrazin-2-yl-methanone

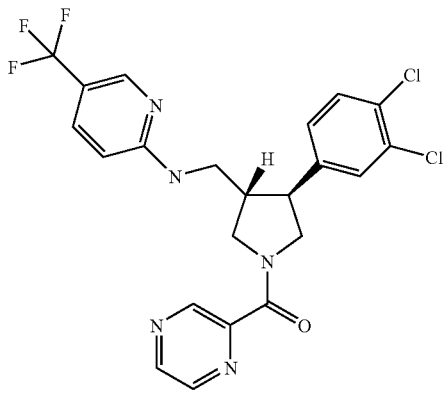

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 2-Pyrazin-carboxylic acid
ES-MS m/e: 496.2 (M+H⁺).

EXAMPLE 19

(3SR,4RS)-1-(4-{-3-(3,4-Dichloro-phenyl)-4-[(5-trifluoromethyl-pyridin-2-ylamino)-methyl]-pyrrolidine-1-carbonyl}-piperidin-1-yl)-ethanone

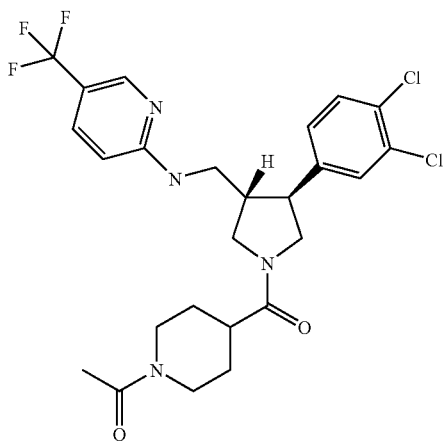

Coupling between a compound of formula XVI and an acid chloride according to General procedure II
Amine: (3SR,4RS)-[4-(3,4-Dichloro-phenyl)-pyrrolidin-3-ylmethyl]-(5-trifluoromethyl-pyridin-2-yl)-amine
Acid chloride: 1-Acetylisonicopecotoylchloride
ES-MS m/e: 543.2 (M+H⁺).

EXAMPLE 20

(3SR,4RS)-{3-(3,4-Dichloro-phenyl)-4-[(5-trifluoromethyl-pyridin-2-ylamino)-methyl]-pyrrolidin-1-yl}-(6-methyl-pyridazin-4-yl)-methanone

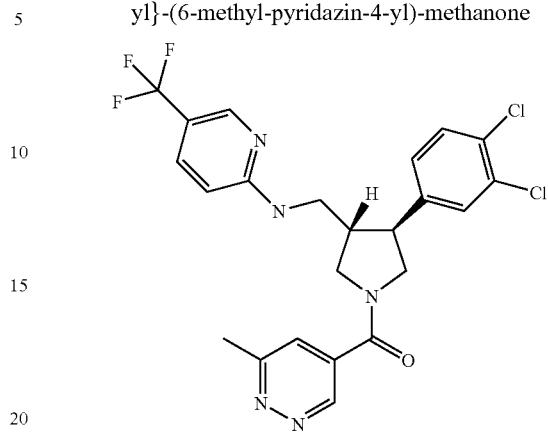

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 6-Methyl-pyridazine-4-carboxylic acid (described herein below)
ES-MS m/e: 510.1 (M+H⁺).

6-Methyl-pyridazine-4-carboxylic acid

To a stirred solution of 3-chloro-6-methyl-pyridazine-4-carboxylic acid (500 mg, 2.89 mmol) in MeOH (50 mL) was added NaOH (395 mg, 9.85 mmol) in pellets, followed by 150 mg of Pd/C (10%). The reaction mixture was put under a H₂ atmosphere for 3 hours (atmospheric pressure). The reaction mixture was filtered on celite, acidified with aq. HCl (pH=6), and concentrated under vacuo. Column chromatography (SiO₂, CH₂Cl₂/MeOH 7/3) yielded 6-methyl-pyridazine-4-carboxylic acid (120 mg, 29%) as a brown solid.

EXAMPLE 21

(3SR,4RS)-(3-(3,4-Dichloro-phenyl)-4-[(5-trifluoromethyl-pyridin-2-ylamino)-methyl]-pyrrolidine-1-carbonyl}-piperidin-1-yl)-(1-methyl-cyclopropyl)-methanone

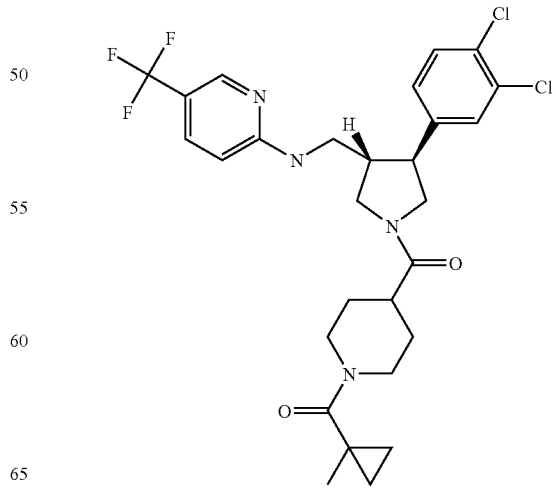

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 1-(1-Methyl-cyclopropanecarbonyl)-piperidine-4-carboxylic acid (described herein below)
ES-MS m/e: 583.1 (M+H⁺).

a) 1-(1-Methyl-cyclopropanecarbonyl)-piperidine-4-carboxylic acid ethyl ester

Amid coupling according to General procedure I
Amine: Ethyl isonipecotate (CAS RN: 1126-09-6)
Carboxylic acid: 1-Methylcyclopropane-carboxylic acid (CAS RN: 6914-76-7)
ES-MS m/e: 240.4 (M+H⁺).

b) 1-(1-Methyl-cyclopropanecarbonyl)-piperidine-4-carboxylic acid 1-(1-Methyl-cyclopropanecarbonyl)-piperidine-4-carboxylic acid ethyl ester (6.34 g, 26.5 mmol) and LiOH (1.67 g, 39.7 mmol) were stirred in a mixture of ethanol (30 mL), THF (30 mL) and water (15 mL) for 90 min at ambient temperature. After evaporation of the volatiles the residue was taken up in dichloro methane and extracted with 1N HCl. The organic phase was dried over sodium sulfate, filtered and evaporated to yield the title product (4.8 g, 86%) as colorless solid.
ES-MS m/e: 210.2 (M−H)⁻.

EXAMPLE 22

(3SR,4RS)-{3-(3,4-Dichloro-phenyl)-4-[(5-trifluoromethyl-pyridin-2-ylamino)-methyl]-pyrrolidin-1-yl}-pyridazin-4-yl-methanone

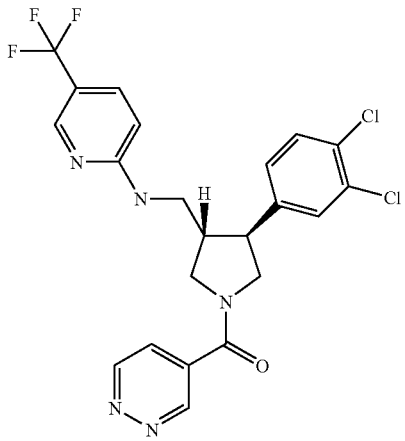

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: Pyridazine-4-carboxylic acid
ES-MS m/e: 496.2 (M+H⁺).

EXAMPLE 23

(3SR,4RS)-{3-(3,4-Dichloro-phenyl)-4-[(5-trifluoromethyl-pyridin-2-ylamino)-methyl]-pyrrolidin-1-yl}-(3,6-dimethyl-pyridazin-4-yl)-methanone

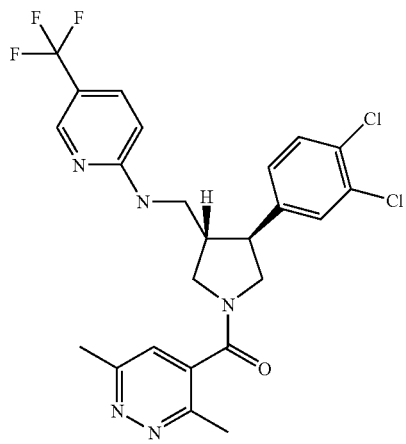

Amid coupling according to General procedure I
Amine: (3SR,4RS)-[4-(3,4-Dichloro-phenyl)-pyrrolidin-3-ylmethyl]-(5-trifluoromethyl-pyridin-2-yl)-amine
Carboxylic acid: 3,6-Dimethylpyridazine-4-carboxylic acid (CAS RN: 1017485-56-1)
ES-MS m/e: 524.3 (M+H⁺).

Scheme 4:
Preparation of derivatives of formula XIX wherein A is NH-tosylate approach

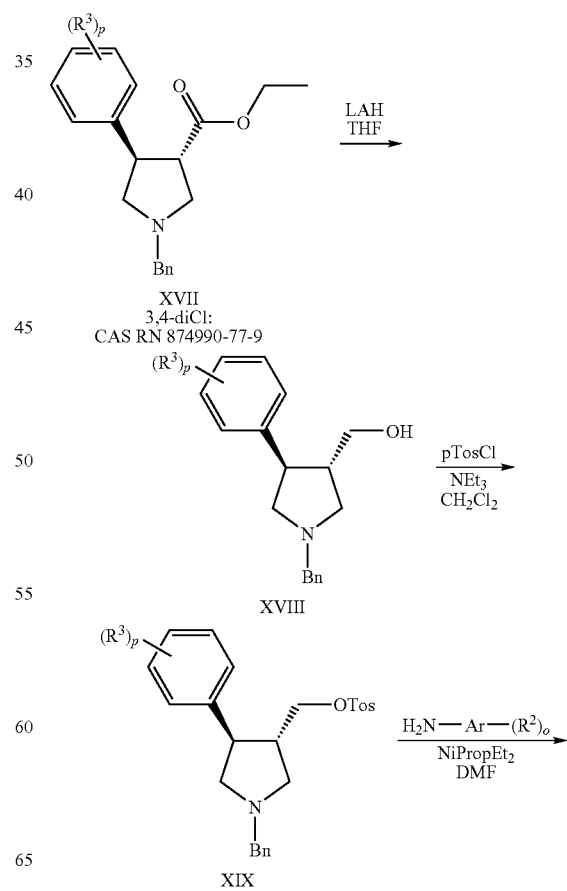

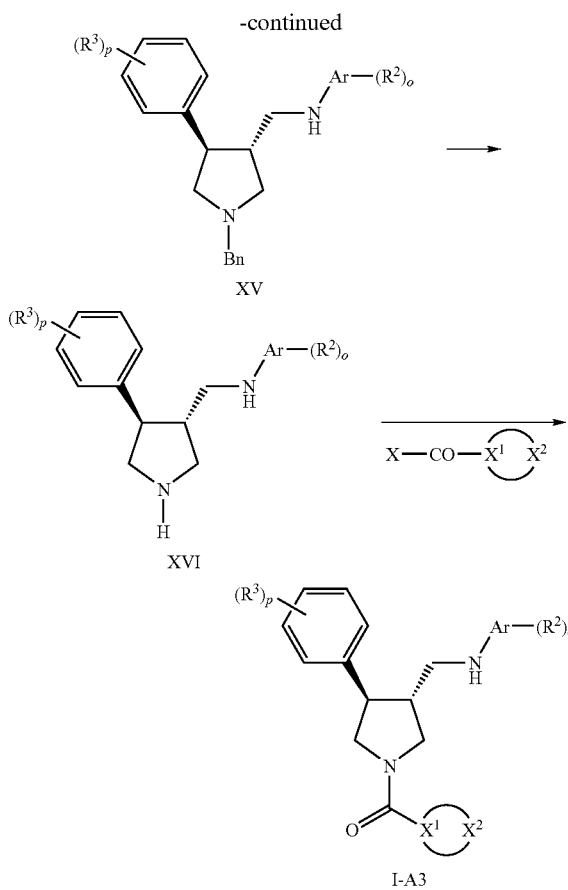

wherein $(R^3)_p$ is 3,4-di-Cl and the other substituents are as described above.

Preparation of (3SR,4RS) Toluene-4-sulfonic acid-1-benzyl-4-(3,4-dichloro-phenyl)-pyrrolidin-3-ylmethyl ester

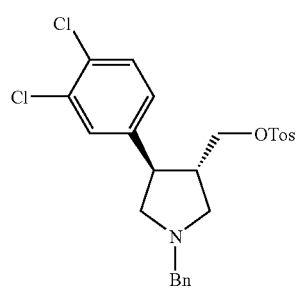

a) (3SR,4RS) [1-Benzyl-4-(3,4-dichloro-phenyl)-pyrrolidin-3-yl]-methanol (3SR,4RS) 1-Benzyl-4-(3,4-dichloro-phenyl)-pyrrolidine-3-carboxylic acid ethyl ester (3.6 g, 0.01 mol) were dissolved in THF (70 mL). At 0° C. LiAlH$_4$ (0.38 g, 0.01 mol) was added portion wise. After stirring at 0° C. for 4 h water (3 mL), then 5N NaOH (3 mL) and additional water (9 mL) was added. After stirring at ambient temperature for 30 min the mixture was extracted with ethyl acetate (3×10 mL), the combined organic phases were dried on sodium sulfate, filtered and evaporated. The crude title product was obtained as a light yellow oil (3.0 g, 94%) and directly used in the next step.

ES-MS m/e: 337.5 (M+H$^+$).

b) (3SR,4RS) Toluene-4-sulfonic acid-1-benzyl-4-(3,4-dichloro-phenyl)-pyrrolidin-3-ylmethyl ester (3SR,4RS) [1-Benzyl-4-(3,4-dichloro-phenyl)-pyrrolidin-3-yl]-methanol (2.9 g, 9 mmol) were dissolved in dichloro methane (60 mL) and cooled to 0° C. Then triethyl amine (1.6 mL, 11 mmol) and p-TosCl (1.81 g, 9.9 mmol) were added. The reaction mixture was allowed to slowly warm up to ambient temperature and stirred over night. Then the volatiles were removed and the residue directly subjected to column chromatography (silica gel, heptane, heptane/ethyl acetate 9:1/4:1/1:1) to yield the title product (2.5 g, 59%) as a colorless oil.

ES-MS m/e: 491.5 (M+H$^+$).

EXAMPLE 24

(3SR,4RS)-{3-[(5-Chloro-pyrimidin-2-ylamino)-methyl]-4-(3,4-dichloro-phenyl)-pyrrolidin-1-yl]-[1-(1-methyl-cyclopropanecarbonyl)-piperidin-4-yl]-methanone

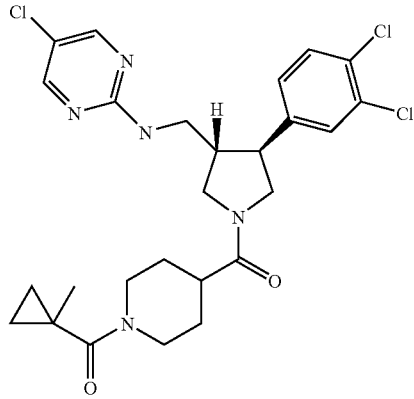

a) (3SR,4RS) [1-Benzyl-4-(3,4-dichloro-phenyl)-pyrrolidin-3-ylmethyl]-(5-chloro-pyrimidin-2-yl)-amine Nucleophilic substitution reaction according to General Procedure VI
Aniline derivative: 2-Amino-5-chloropyrimidine
Tosylate: (3SR,4RS) Toluene-4-sulfonic acid-1-benzyl-4-(3,4-dichloro-phenyl)-pyrrolidin-3-ylmethyl ester
ES-MS m/e: 448.9 (M+H$^+$).

b) (3SR,4RS) (5-Chloro-pyrimidin-2-yl)-[4-(3,4-dichloro-phenyl)-pyrrolidin-3-ylmethyl]-amine Cleavage of the n-benzyl group according to General Procedure V
Amine: (3SR,4RS) [1-Benzyl-4-(3,4-dichloro-phenyl)-pyrrolidin-3-ylmethyl]-(5-chloro-pyrimidin-2-yl)-amine
ES-MS m/e: 358.9 (M+H$^+$).

c) (3SR,4RS)-{3-[(5-Chloro-pyrimidin-2-ylamino)-methyl]-4-(3,4-dichloro-phenyl)-pyrrolidin-1-yl]-[1-(1-methyl-cyclopropanecarbonyl)-piperidin-4-yl]-methanone Amid coupling according to General procedure I
Amine: (3SR,4RS) (5-Chloro-pyrimidin-2-yl)-[4-(3,4-dichloro-phenyl)-pyrrolidin-3-ylmethyl]-amine
Carboxylic acid: 1-(1-Methyl-cyclopropanecarbonyl)-piperidine-4-carboxylic acid
ES-MS m/e: 550.3 (M+H⁺).

EXAMPLE 25

(3SR,4RS)-{1-{4-[3-[(5-Chloro-pyrimidin-2-ylamino)-methyl]-4-(3,4-dichloro-phenyl)-pyrrolidine-1-carbonyl]-piperidin-1-yl}-ethanone

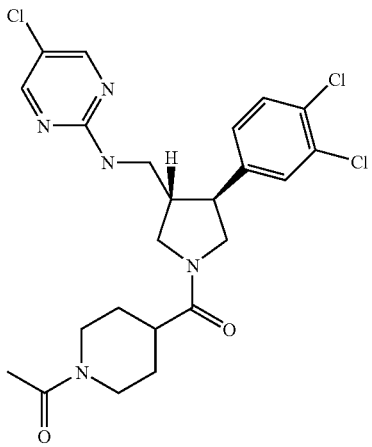

Coupling between a compound of formula XVI and an acid chloride according to General procedure II
Amine: (3SR,4RS) (5-Chloro-pyrimidin-2-yl)-[4-(3,4-dichloro-phenyl)-pyrrolidin-3-ylmethyl]-amine
Acid chloride: 1-Acetylisonicopecotoylchloride
ES-MS m/e: 510.2 (M+H⁺).

EXAMPLE 26

(3SR,4RS)-{5-[3-[(5-Chloro-pyrimidin-2-ylamino)-methyl]-4-(3,4-dichloro-phenyl)-pyrrolidine-1-carbonyl]-pyridine-2-carbonitrile

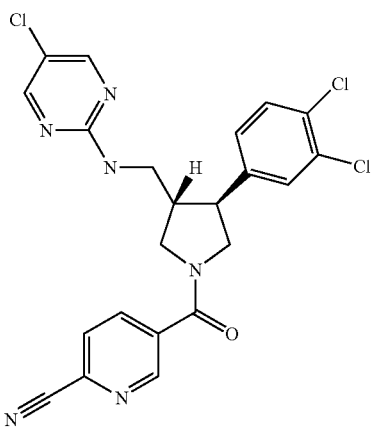

Amid coupling according to General procedure I
Amine: (3SR,4RS) (5-Chloro-pyrimidin-2-yl)-[4-(3,4-dichloro-phenyl)-pyrrolidin-3-ylmethyl]-amine
Carboxylic acid: 6-Cyano-nicotinic acid
ES-MS m/e: 489.1 (M+H⁺).

EXAMPLE 27

(3SR,4RS)-[3-[(5-Chloro-pyrimidin-2-ylamino)-methyl]-4-(3,4-dichloro-phenyl)-pyrrolidin-1-yl]-(6-methyl-pyridazin-4-yl)-methanone

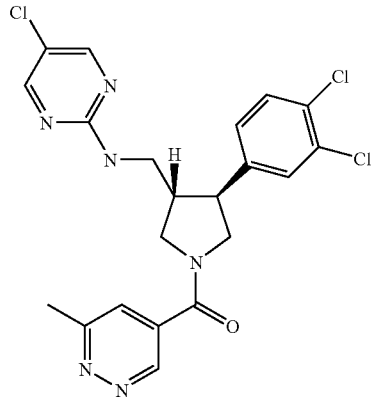

Amid coupling according to General procedure I
Amine: (3SR,4RS) (5-Chloro-pyrimidin-2-yl)-[4-(3,4-dichloro-phenyl)-pyrrolidin-3-ylmethyl]-amine
Carboxylic acid: 6-Methyl-pyridazine-4-carboxylic acid
ES-MS m/e: 477.1 (M+H⁺).

EXAMPLE 28

(3SR,4RS)-{3-(3,4-Dichloro-phenyl)-4-[(4-trifluoromethyl-phenylamino)-methyl]-pyrrolidin-1-yl}-(4-methanesulfonyl-piperazin-1-yl)-methanone

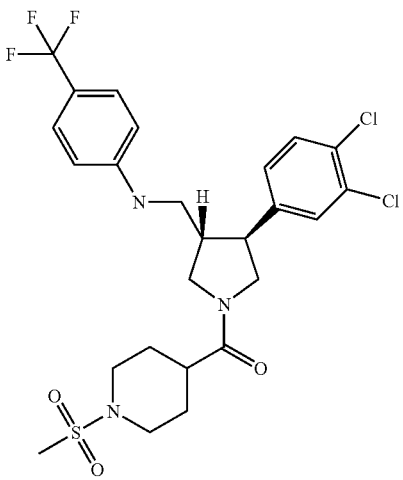

(3SR,4RS) [1-Benzyl-4-(3,4-dichloro-phenyl)-pyrrolidin-3-ylmethyl]-(4-trifluoromethyl-phenyl)-amine Nucleophilic substitution reaction according to General Procedure VI
Aniline derivative: 4-Aminobenzotrifluorid
Tosylate: (3SR,4RS) Toluene-4-sulfonic acid-1-benzyl-4-(3,4-dichloro-phenyl)-pyrrolidin-3-ylmethyl ester
ES-MS m/e: 480.5 (M+H$^+$).

b) (3SR,4RS) [4-(3,4-Dichloro-phenyl)-pyrrolidin-3-ylmethyl]-(4-trifluoromethyl-phenyl)-amine Cleavage of the n-benzyl group according to General Procedure V
Amine: (3SR,4RS) [1-Benzyl-4-(3,4-dichloro-phenyl)-pyrrolidin-3-ylmethyl]-(4-trifluoromethyl-phenyl)-amine
ES-MS m/e: 390.4 (M+H$^+$).

c) (3SR,4RS)-{3-[(5-Chloro-pyrimidin-2-ylamino)-methyl]-4-(3,4-dichloro-phenyl)-pyrrolidin-1-yl]-[1-(1-methyl-cyclopropanecarbonyl)-piperidin-4-yl]-methanone Coupling between a compound of formula XVI and an acid chloride or carbamoyl chloride according to General procedure II
Amine: (3SR,4RS) [4-(3,4-Dichloro-phenyl)-pyrrolidin-3-ylmethyl]-(4-trifluoromethyl-phenyl)-amine
Carbamoyl chloride: 4-Methanesulfonyl-piperazine-1-carbonyl chloride (CAS-RN 65463-96-9)
ES-MS m/e: 579.2 (M+H$^+$).

EXAMPLE 29

(3SR,4RS)-[3-[(4-Chloro-phenylamino)-methyl]-4-(3,4-dichloro-phenyl)-pyrrolidin-1-yl]-(4-methanesulfonyl-piperazin-1-yl)-methanone

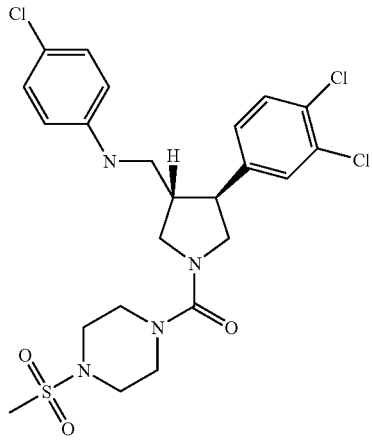

a) (3SR,4RS) [1-Benzyl-4-(3,4-dichloro-phenyl)-pyrrolidin-3-ylmethyl]-(4-chloro-phenyl)-amine Nucleophilic substitution reaction according to General Procedure VI
Aniline derivative: 4-Chloroaniline
Tosylate: (3SR,4RS) Toluene-4-sulfonic acid-1-benzyl-4-(3,4-dichloro-phenyl)-pyrrolidin-3-ylmethyl ester
ES-MS m/e: 446.9 (M+H$^+$).

b) (3SR,4RS) (4-Chloro-phenyl)-[4-(3,4-dichloro-phenyl)-pyrrolidin-3-ylmethyl]-amine Cleavage of the n-benzyl group according to General Procedure V
Amine: (3SR,4RS) [1-Benzyl-4-(3,4-dichloro-phenyl)-pyrrolidin-3-ylmethyl]-(4-chloro-phenyl)-amine
ES-MS m/e: 356.8 (M+H$^+$).

c) (3SR,4RS)-[3-[(4-Chloro-phenylamino)-methyl]-4-(3,4-dichloro-phenyl)-pyrrolidin-1-yl]-(4-methanesulfonyl-piperazin-1-yl)-methanone Coupling between a compound of formula XVI and an acid chloride or carbamoyl chloride according to General procedure II
Amine: (3SR,4RS) 4-Chloro-phenyl)-[4-(3,4-dichloro-phenyl)-pyrrolidin-3-ylmethyl]-amine
Carbamoyl chloride: 4-Methanesulfonyl-piperazine-1-carbonyl chloride (CAS-RN 65463-96-9)
ES-MS m/e: 547.1 (M+H$^+$).

EXAMPLE 30

(3SR,4RS)-[3-[(5-Chloro-pyridin-2-ylamino)-methyl]-4-(3,4-dichloro-phenyl)-pyrrolidin-1-yl]-(4-methanesulfonyl-piperazin-1-yl)-methanone

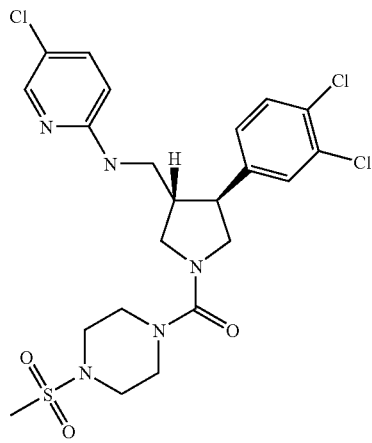

a) (3SR,4RS) [1-Benzyl-4-(3,4-dichloro-phenyl)-pyrrolidin-3-ylmethyl]-(5-chloro-pyridin-2-yl)-amine Nucleophilic substitution reaction according to General Procedure VI
Aniline derivative: 2-Amino-5-chloropyridine
Tosylate: (3SR,4RS) Toluene-4-sulfonic acid-1-benzyl-4-(3,4-dichloro-phenyl)-pyrrolidin-3-ylmethyl ester
ES-MS m/e: 447.9 (M+H$^+$).

b) (3SR,4RS) (5-Chloro-pyridin-2-yl)-[4-(3,4-dichloro-phenyl)-pyrrolidin-3-ylmethyl]-amine Cleavage of the n-benzyl group according to General Procedure V
Amine: (3SR,4RS) [1-Benzyl-4-(3,4-dichloro-phenyl)-pyrrolidin-3-ylmethyl]-(5-chloro-pyridin-2-yl)-amine
ES-MS m/e: 357.8 (M+H$^+$).

c) (3SR,4RS)-[3-[(5-Chloro-pyridin-2-ylamino)-methyl]-4-(3,4-dichloro-phenyl)-pyrrolidin-1-yl]-(4-methanesulfonyl-piperazin-1-yl)-methanone Coupling between a compound of formula XVI and an acid chloride or carbamoyl chloride according to General procedure II
Amine: (3SR,4RS)(5-Chloro-pyridin-2-yl)-[4-(3,4-dichloro-phenyl)-pyrrolidin-3-ylmethyl]-amine
Carbamoyl chloride: 4-Methanesulfonyl-piperazine-1-carbonyl chloride (CAS-RN 65463-96-9)
ES-MS m/e: 546.1 (M+H$^+$).

EXAMPLE 31

(3SR,4RS)-2-{[4-(3,4-Dichloro-phenyl)-1-(4-methanesulfonyl-piperazine-1-carbonyl)-pyrrolidin-3-ylmethyl]-amino}-pyrimidine-5-carbonitrile

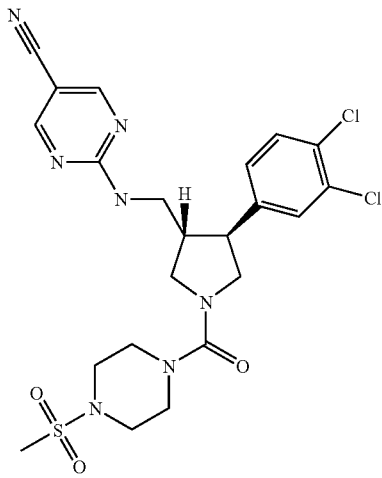

a) (3SR,4RS) 2-{[1-Benzyl-4-(3,4-dichloro-phenyl)-pyrrolidin-3-ylmethyl]-amino}-pyrimidine-5-carbonitrile Nucleophilic substitution reaction according to General Procedure VI
Aniline derivative: 2-Amino-5-cyanopyrimidine
Tosylate: (3SR,4RS) Toluene-4-sulfonic acid-1-benzyl-4-(3,4-dichloro-phenyl)-pyrrolidin-3-ylmethyl ester
ES-MS m/e: 439.5 (M+H$^+$).

b) (3SR,4RS) 2-{[4-(3,4-Dichloro-phenyl)-pyrrolidin-3-ylmethyl]-amino}-pyrimidine-5-carbonitrile Cleavage of the n-benzyl group according to General Procedure V
Amine: (3SR,4RS) 2-{[1-Benzyl-4-(3,4-dichloro-phenyl)-pyrrolidin-3-ylmethyl]-amino}-pyrimidine-5-carbonitrile
ES-MS m/e: 349.4 (M+H$^+$).

c) (3SR,4RS)-2-{[4-(3,4-Dichloro-phenyl)-1-(4-methanesulfonyl-piperazine-1-carbonyl)-pyrrolidin-3-ylmethyl]-amino}-pyrimidine-5-carbonitrile Coupling between a compound of formula XVI and an acid chloride or carbamoyl chloride according to General procedure II
Amine: (3SR,4RS) 2-{[4-(3,4-Dichloro-phenyl)-pyrrolidin-3-ylmethyl]-amino}-pyrimidine-5-carbonitrile
Carbamoyl chloride: 4-Methanesulfonyl-piperazine-1-carbonyl chloride (CAS-RN 65463-96-9)
ES-MS m/e: 538.2 (M+H$^+$).

EXAMPLE 32

(3SR,4RS) 5-{[4-(3,4-Dichloro-phenyl)-1-(4-methanesulfonyl-piperazine-1-carbonyl)-pyrrolidin-3-ylmethyl]-amino}-pyrazine-2-carbonitrile

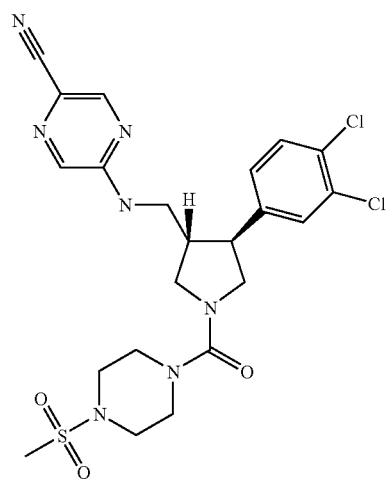

a) (3SR,4RS) 5-{[1-Benzyl-4-(3,4-dichloro-phenyl)-pyrrolidin-3-ylmethyl]-amino}-pyrazine-2-carbonitrile Nucleophilic substitution reaction according to General Procedure VI
Aniline derivative: 2-Amino-5-cyanopyrazine
Tosylate: (3SR,4RS) Toluene-4-sulfonic acid-1-benzyl-4-(3,4-dichloro-phenyl)-pyrrolidin-3-ylmethyl ester
ES-MS m/e: 439.5 (M+H$^+$).

b) (3SR,4RS) 5-{[4-(3,4-Dichloro-phenyl)-pyrrolidin-3-ylmethyl]-amino}-pyrazine-2-carbonitrile Cleavage of the n-benzyl group according to General Procedure V
Amine: (3SR,4RS) 5-{[1-Benzyl-4-(3,4-dichloro-phenyl)-pyrrolidin-3-ylmethyl]-amino}-pyrazine-2-carbonitrile
ES-MS m/e: 349.4 (M+H$^+$).

c) (3SR,4RS) 5-{[4-(3,4-Dichloro-phenyl)-1-(4-methanesulfonyl-piperazine-1-carbonyl)-pyrrolidin-3-ylmethyl]-amino}-pyrazine-2-carbonitrile Coupling between a compound of formula XVI and an acid chloride or carbamoyl chloride according to General procedure II
Amine: (3SR,4RS) 5-{[4-(3,4-Dichloro-phenyl)-pyrrolidin-3-ylmethyl]-amino}-pyrazine-2-carbonitrile
Carbamoyl chloride: 4-Methanesulfonyl-piperazine-1-carbonyl chloride (CAS-RN 65463-96-9)
ES-MS m/e: 538.2 (M+H$^+$).

EXAMPLE 33

(3SR,4RS) 1-(4-{3-(3,4-Dichloro-phenyl)-4-[(5-trifluoromethyl-pyrimidin-2-ylamino)-methyl]-pyrrolidine-1-carbonyl}-piperidin-1-yl)-ethanone

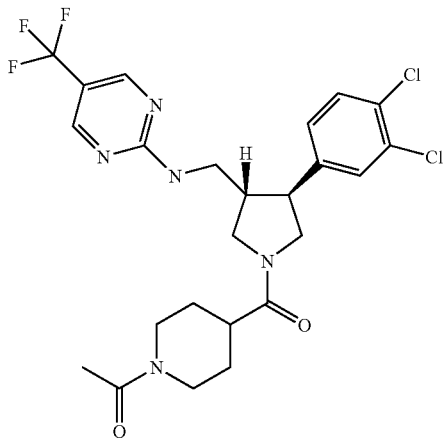

a) (3SR,4RS) [1-Benzyl-4-(3,4-dichloro-phenyl)-pyrrolidin-3-ylmethyl]-(5-trifluoromethyl-pyrimidin-2-yl)-amine Nucleophilic substitution reaction according to General Procedure VI Aniline derivative: 2-Amino-5-trifluoromethylpyrimidin (CAS RN:69034-08-8)
Tosylate: (3SR,4RS) Toluene-4-sulfonic acid-1-benzyl-4-(3,4-dichloro-phenyl)-pyrrolidin-3-ylmethyl ester
ES-MS m/e: 482.5 (M+H⁺).

b) (3SR,4RS) [4-(3,4-Dichloro-phenyl)-pyrrolidin-3-ylmethyl]-(5-trifluoromethyl-pyrimidin-2-yl)-amine Cleavage of the n-benzyl group according to General Procedure V Amine: (3SR,4RS) 5-{[1-Benzyl-4-(3,4-dichloro-phenyl)-pyrrolidin-3-ylmethyl]-(5-trifluoromethyl-pyrimidin-2-yl)-amine
ES-MS m/e: 392.4 (M+H⁺).

c) (3SR,4RS) 1-(4-{3-(3,4-Dichloro-phenyl)-4-[5-trifluoromethyl-pyrimidin-2-ylamino)-methyl]-pyrrolidine-1-carbonyl}-piperidin-1-yl)-ethanone Coupling between a compound of formula XVI and an acid chloride according to General procedure II Amine: (3SR,4RS) [4-(3,4-Dichloro-phenyl)-pyrrolidin-3-ylmethyl]-(5-trifluoromethyl-pyrimidin-2-yl)-amine
Acid chloride: 1-Acetylisonicopecotoylchloride
ES-MS m/e: 544.1 (M+H⁺).

EXAMPLE 34

(3SR,4RS) {3-(3,4-Dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone

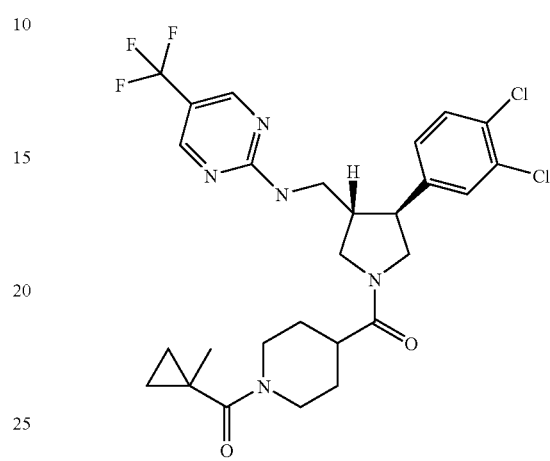

Amid coupling according to General procedure I

Amine: (3SR,4RS) [4-(3,4-Dichloro-phenyl)-pyrrolidin-3-ylmethyl]-(5-trifluoromethyl-pyrimidin-2-yl)-amine
Carboxylic acid: 1-(1-Methyl-cyclopropanecarbonyl)-piperidine-4-carboxylic acid
ES-MS m/e: 584.0 (M+H⁺).

EXAMPLE 35

(3SR,4RS) {3-(3,4-Dichloro-phenyl)-4-[(5-trifluoromethyl-pyrimidin-2-ylamino)-methyl]-pyrrolidin-1-yl}-(6-methyl-pyridazin-4-yl)-methanone

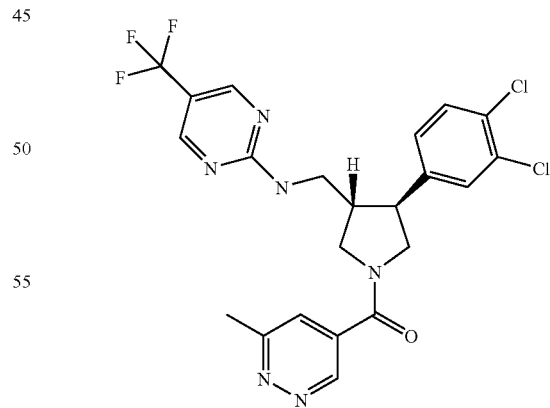

Amid coupling according to General procedure I

Amine: (3SR,4RS) [4-(3,4-Dichloro-phenyl)-pyrrolidin-3-ylmethyl]-(5-trifluoromethyl-pyrimidin-2-yl)-amine
Carboxylic acid: 6-Methyl-pyridazine-4-carboxylic acid
ES-MS m/e: 511.3 (M+H⁺).

Scheme 5:
Preparartion of Pyrrolidine Intermediate XXV

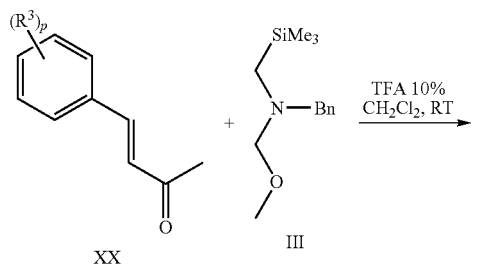

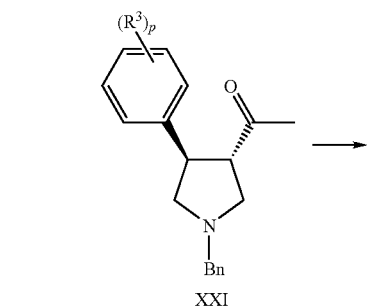

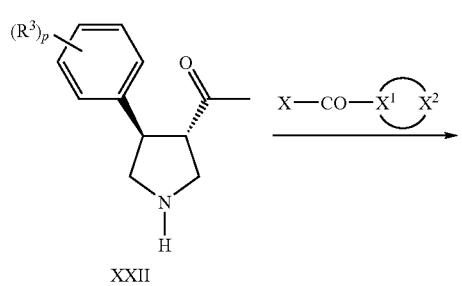

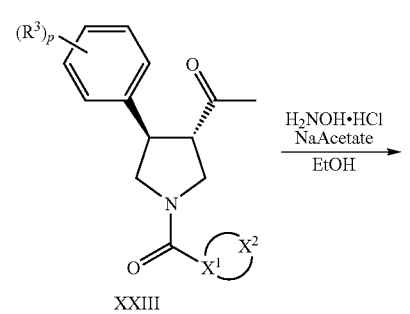

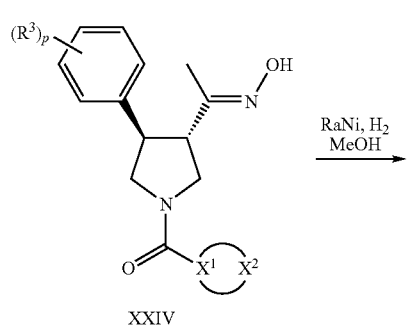

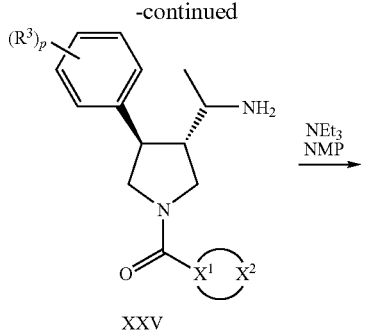

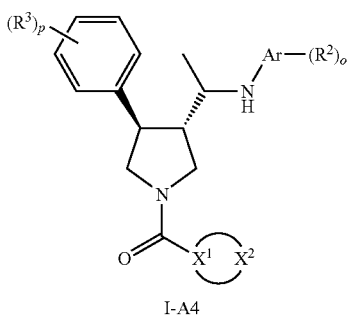

wherein $(R^3)_p$ is 3,4-di-Cl and the other substituents are as described above.

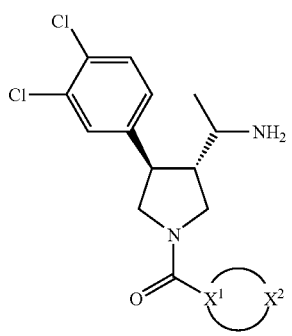

a) 1-[(3SR,4RS)-1-Benzyl-4-(3,4-dichloro-phenyl)-pyrrolidin-3-yl]-ethanone

A solution of N-(methoxymethyl)-N-(phenylmethyl)-N-(trimethylsilyl)methylamine (32.78 g, 0.138 mol) in CH₂Cl₂ (50 mL) was added drop wise, over a 30 minutes period, to a stirred solution of (E)-4-(3,4-dichloro-phenyl)-but-3-en-2-one (CAS RN: 55420-70-7) (19.80 g, 0.092 mol) and trifluoroacetic acid (1.05 mL, 0.009 mol) in CH₂Cl₂ (100 mL) at 0° C. The ice bath was removed, and the solution was stirred at 25° C. for an additional 48 h. It was then concentrated and purification by flash chromatography (SiO₂, CH₂Cl₂/MeOH 98:2) afforded the title compound (28.3 g, 88%) as a yellow oil. ES-MS m/e: 348.2 (M+H⁺).

b) 1-[(3SR,4RS)-4-(3,4-Dichloro-phenyl)-pyrrolidin-3-yl]-ethanone

To a solution of 1-[(3SR,4RS)-1-benzyl-4-(3,4-dichloro-phenyl)-pyrrolidin-3-yl]-ethanone 4.00 g (9.20 mmol) dissolved in $CH_3CN$ (50 mL) was added 2.48 mL (18.40 mmol) of 2,2,2-trichloroethyl chloroformate and stirring was continued for 3 hours at RT. Volatiles were removed under vacuo, and the residue was dissolved in AcOH (30 mL) before a total of 1.5 g of Zn dust was added portion wise. After three hours at RT, the reaction mixture was filtered on celite, the solvent removed under vacuo, followed by extraction with EtOAc/aq. $NaHCO_3$ (basic pH). The organic phases were dried on $Na_2SO_4$ and column chromatography ($SiO_2$, $CH_2Cl_2$/MeOH 9:1 to 8:2) yielded the title compound (1.50 g, 63%) as a colorless oil. ES-MS m/e: 258.0 ($M+H^+$).

c) 1-[(3SR,4RS)-4-(3,4-Dichloro-phenyl)-1-(4-methanesulfonyl-piperazine-1-carbonyl)-pyrrolidin-3-yl]-ethanone Using the general procedure II, the coupling between 1-[(3SR,4RS)-4-(3,4-dichloro-phenyl)-pyrrolidin-3-yl]-ethanone (1.88 g, 7.28 mmol) and 4-methanesulfonyl-piperazine-1-carbonyl chloride (1.98 g, 8.74 mmol) yielded the title product (2.40 g, 74%) as a colorless oil after purification by flash chromatography ($SiO_2$, EtOAc). ES-MS m/e: 449.5 ($M+H^+$).

d) 1-[(3SR,4RS)-4-(3,4-Dichloro-phenyl)-1-(4-methanesulfonyl-piperazine-1-carbonyl)-pyrrolidin-3-yl]-ethanone oxime 1-[(3SR,4RS)-4-(3,4-Dichloro-phenyl)-1-(4-methanesulfonyl-piperazine-1-carbonyl)-pyrrolidin-3-yl]-ethanone (0.87 g, 2 mmol), hydroxylamine hydrochloride (0.28 g, 2.05 mmol) and sodium acetate (0.33 g, 2.06 mmol) were dissolved in ethanol (9.0 mL) and heated to reflux for 2 h. After cooling to ambient temperature water (20 mL) was added. The mixture was extracted with ethyl acetate (3×10 mL) and the combined organic phases were dried over sodium sulfate, filtered and concentrated. The residue was subjected to column chromatography (silica gel, ethyl acetate) to yield the title compound as a colorless foam (0.74 g, 82%). ES-MS m/e: 437.5 ($M+H^+$).

e) [(3SR,4RS)-3-(1-(RS)-Amino-ethyl)-4-(3,4-dichloro-phenyl)-pyrrolidin-1-yl]-(4-methanesulfonyl-piperazin-1-yl)-methanone and [(3SR,4RS)-3-(1-(SR)-Amino-ethyl)-4-(3,4-dichloro-phenyl)-pyrrolidin-1-yl]-(4-methanesulfonyl-piperazin-1-yl)-methanone 1-[(3SR,4RS)-4-(3,4-Dichloro-phenyl)-1-(4-methanesulfonyl-piperazine-1-carbonyl)-pyrrolidin-3-yl]-ethanone oxime (0.14 g, 0.3 mmol) were dissolved in methanol (10 mL) and treated under an atmosphere of $H_2$ (5 bar) at ambient temperature for several hours. The crude product was, after filtration and evaporation of the solvent, subjected to column chromatography (silica gel, dichloro methane, dichloro methane/methanol 2%, 5%) to yield the title product as a mixture of diastereomers as a colorless foam (0.082 g, 60%). ES-MS m/e: 450.5 ($M+H^+$).

EXAMPLE 36

(3SR,4RS) 6-{1-(RS)-[4-(3,4-Dichloro-phenyl)-1-(4-methanesulfonyl-piperazine-1-carbonyl)-pyrrolidin-3-yl]-ethylamino}-nicotinonitrile and (3SR,4RS) 6-{1-(SR)-[4-(3,4-Dichloro-phenyl)-1-(4-methanesulfonyl-piperazine-1-carbonyl)-pyrrolidin-3-yl]-ethylamino}-nicotinonitrile

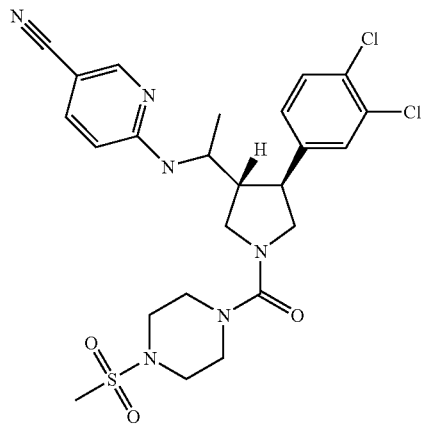

Nucleophilic aromatic substitution reaction: Coupling of XXV with heteroaromatic chlorides and/or methylsulfones according to General procedure IV Amine: [(3SR,4RS)-3-(1-(RS)-Amino-ethyl)-4-(3,4-dichloro-phenyl)-pyrrolidin-1-yl]-(4-methanesulfonyl-piperazin-1-yl)-methanone and [(3SR,4RS)-3-(1-(SR)-Amino-ethyl)-4-(3,4-dichloro-phenyl)-pyrrolidin-1-yl]-(4-methanesulfonyl-piperazin-1-yl)-methanone Heteroaryl chloride: 6-Chloro-3-pyridincarbonitrile
ES-MS m/e: 551.2 ($M+H^+$).

EXAMPLE 37

(3SR,4RS) {3-(3,4-Dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone and (3SR,4RS) {3-(3,4-Dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone

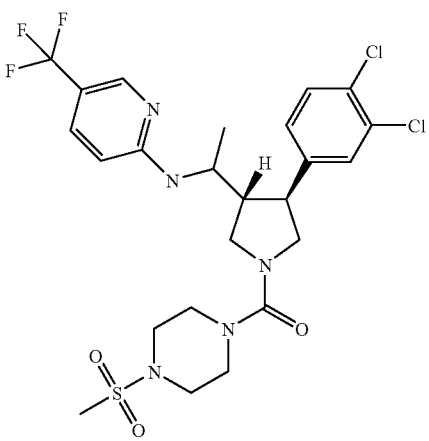

Nucleophilic aromatic substitution reaction: Coupling of XXV with heteroaromatic chlorides and/or methylsulfones according to General procedure IV Amine: [(3SR,4RS)-3-(1-(RS)-Amino-ethyl)-4-(3,4-dichloro-phenyl)-pyrrolidin-1-yl]-(4-methanesulfonyl-piperazin-1-yl)-methanone and [(3SR,4RS)-3-(1-(SR)-Amino-ethyl)-4-(3,4-dichloro-phenyl)-pyrrolidin-1-yl]-(4-methanesulfonyl-piperazin-1-yl)-methanone Heteroaryl chloride: 2-Chloro-5-(trifluoromethyl)-pyridine ES-MS m/e: 594.2 (M+H$^+$).

EXAMPLE 38

(3SR,4RS) {3-(3,4-Dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone

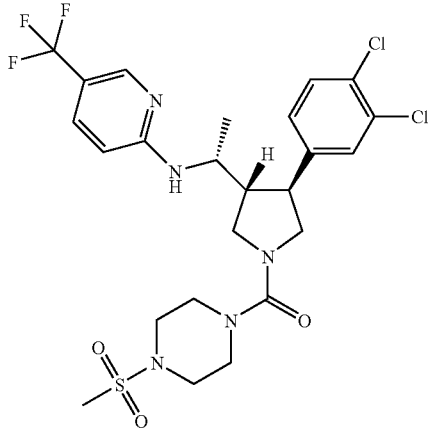

(3SR,4RS) {3-(3,4-Dichloro-phenyl)-4-[1-(RS)-(5-trifluoromethyl-pyridin-2-ylamino)-ethyl]-pyrrolidin-1-yl}-(4-methane sulfonyl-piperazin-1-yl)-methanone and (3SR,4RS) {3-(3,4-dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone (150 mg) were separated (HPLC, YMC Pack SIL column) to yield the title compound as a colorless foam (1.fraction eluted). ES-MS m/e: 594.2 (M+H$^+$).

EXAMPLE 39

(3SR,4RS) {3-(3,4-Dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone

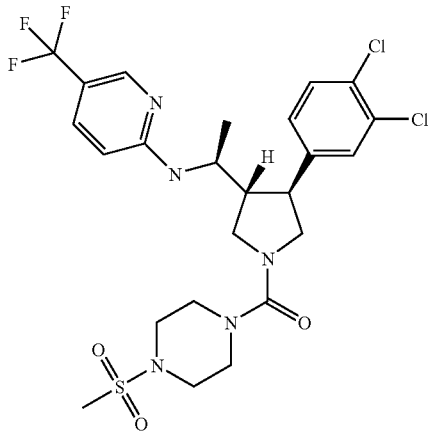

(3SR,4RS) {3-(3,4-Dichloro-phenyl)-4-[1-(RS)-(5-trifluoromethyl-pyridin-2-ylamino)-ethyl]-pyrrolidin-1-yl}-(4-methane sulfonyl-piperazin-1-yl)-methanone and (3SR,4RS) {3-(3,4-dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone (150 mg) were separated (HPLC, YMC Pack SIL column) to yield the title compound as a colorless foam (2.fraction eluted). ES-MS m/e: 594.2 (M+H$^+$).

Scheme 6:
Preparation of Intermediate XXVIII

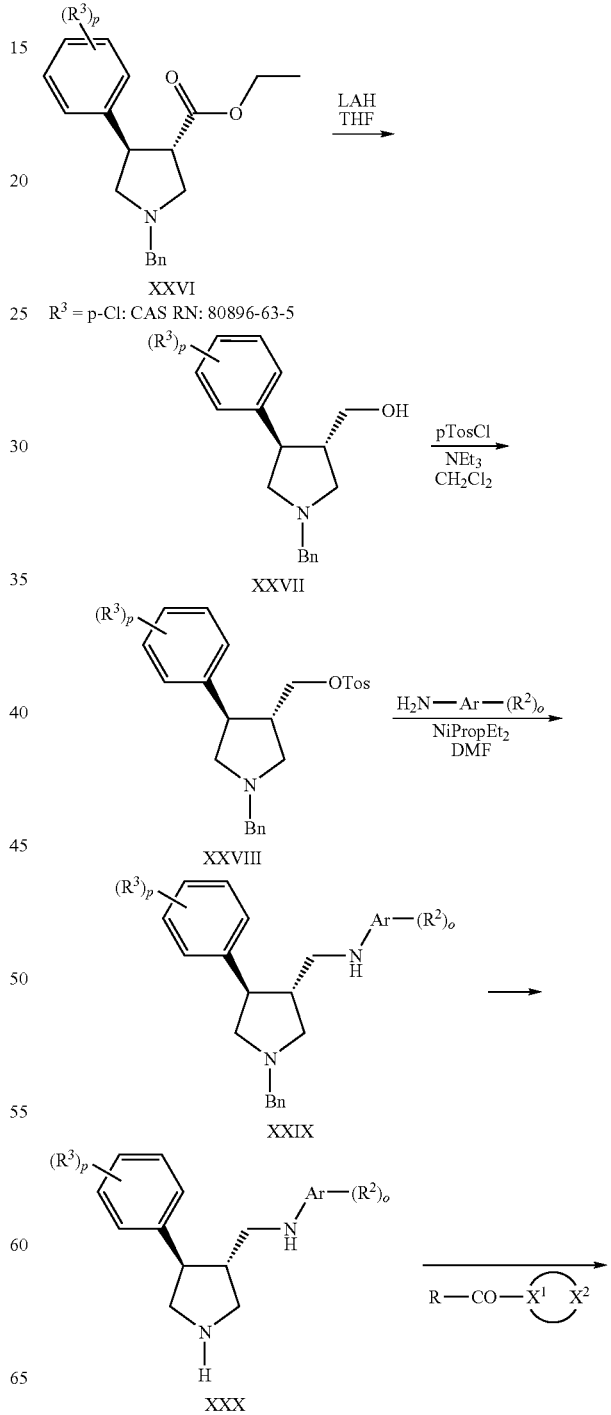

49

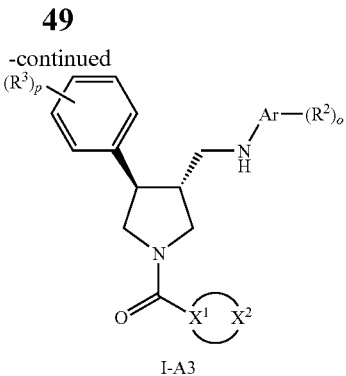

I-A3 wherein $(R^3)_p$ is 4-Cl and the other substituents are as described above.

Preparation of (3SR,4RS) Toluene-4-sulfonic acid-1-benzyl-4-(4-chloro-phenyl)-pyrrolidin-3-ylmethyl ester

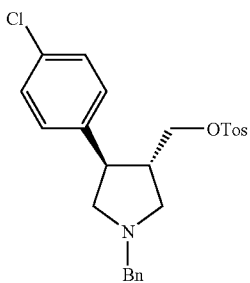

XXVIII a) (3SR,4RS) [1-Benzyl-4-(4-chloro-phenyl)-pyrrolidin-3-yl]-methanol (3SR,4RS) 1-Benzyl-4-(4-chloro-phenyl)-pyrrolidine-3-carboxylic acid ethyl ester (CAS RN: 80896-63-5) (30 g, 0.087 mol) were dissolved in THF (400 mL). At 0° C. LiAlH₄ (3.5 g, 0.092 mol) was added portion wise. After stirring at 0° C. for 4 h water (18 mL), then 5N NaOH (18 mL) and additional water (54 mL) was added. After stirring at ambient temperature for 1 h the mixture was extracted with ethyl acetate (3×100 mL), the combined organic phases were dried on sodium sulfate, filtered and evaporated. The crude title product was obtained as a white solid (24.6 g, 93%) and directly used in the next step.

ES-MS m/e: 302.9 (M+H⁺).

b) (3SR,4RS) Toluene-4-sulfonic acid-1-benzyl-4-(4-chloro-phenyl)-pyrrolidin-3-ylmethyl ester (3SR,4RS) [1-Benzyl-4-(4-chloro-phenyl)-pyrrolidin-3-yl]-methanol (24.5 g, 0.081 mmol) were dissolved in dichloro methane (550 mL) and cooled to 0° C. Then triethyl amine (13.5 mL, 0.097 mol) and p-TosCl (16.25 g, 0.085 mol) were added. The reaction mixture was allowed to slowly warm up to ambient temperature and stirred over night. Then the volatiles were removed and the residue directly subjected to column chromatography (silica gel, heptane, heptane/ethyl acetate 9:1/4:1/1:1) to yield the title product (24.4 g, 66%) as a white solid.

ES-MS m/e: 457.1 (M+H⁺).

50

EXAMPLE 40

(3SR,4RS) {3-(4-Chloro-phenyl)-4-[(5-chloro-pyridin-2-ylamino)-methyl]-pyrrolidin-1-yl}-(6-methyl-pyridazin-4-yl)-methanone

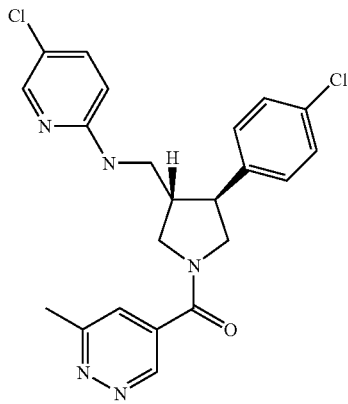

a) (3SR,4RS) [1-Benzyl-4-(4-chloro-phenyl)-pyrrolidin-3-ylmethyl]-(5-chloro-pyridin-2-yl)-amine Nucleophilic substitution reaction according to General Procedure VI Aniline derivative: 2-Amino-5-chloropyridine (CAS RN: 1072-98-6)

Tosylate: (3SR,4RS) Toluene-4-sulfonic acid-1-benzyl-4-(4-chloro-phenyl)-pyrrolidin-3-ylmethyl ester ES-MS m/e: 413.5 (M+H⁺).

b) (3SR,4RS) [4-(4-Chloro-phenyl)-pyrrolidin-3-ylmethyl]-(5-chloro-pyridin-2-yl)-amine Cleavage of the n-benzyl group according to General Procedure V Amine: (3SR,4RS) [1-Benzyl-4-(4-chloro-phenyl)-pyrrolidin-3-ylmethyl]-(5-chloro-pyridin-2-yl)-amine ES-MS m/e: 323.4 (M+H⁺).

c) (3SR,4RS) {3-(4-Chloro-phenyl)-4-[5-chloro-pyridin-2-ylamino)-methyl]-pyrrolidin-1-yl}-(6-methyl-pyridazin-4-yl)-methanone Amid coupling according to General procedure I Amine: (3SR,4RS)[4-(4-Chloro-phenyl)-pyrrolidin-3-ylmethyl]-(5-chloro-pyridin-2-yl)-amine Carboxylic acid: 6-Methyl-pyridazine-4-carboxylic acid ES-MS m/e: 442.2 (M+H⁺).

EXAMPLE 41

(3SR,4RS) {3-(4-Chloro-phenyl)-4-[(5-chloro-pyridin-2-ylamino)-methyl]-pyrrolidin-1-yl}-[1-(1-methyl-cyclopropanecarbonyl)-piperidin-4-yl]-methanone

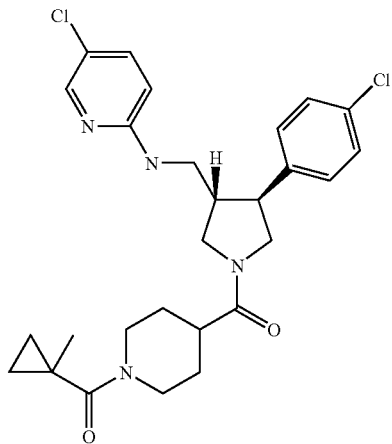

Amid coupling according to General procedure I
Amine: (3SR,4RS)[4-(4-Chloro-phenyl)-pyrrolidin-3-ylmethyl]-(5-chloro-pyridin-2-yl)-amine
Carboxylic acid: 1-(1-Methyl-cyclopropanecarbonyl)-piperidine-4-carboxylic acid
ES-MS m/e: 515.3 (M+H$^+$).

EXAMPLE 42

(3SR,4RS) {3-(4-Chloro-phenyl)-4-[(5-trifluoromethyl-pyridin-2-ylamino)-methyl]-pyrrolidin-1-yl}-(6-methyl-pyridazin-4-yl)-methanone

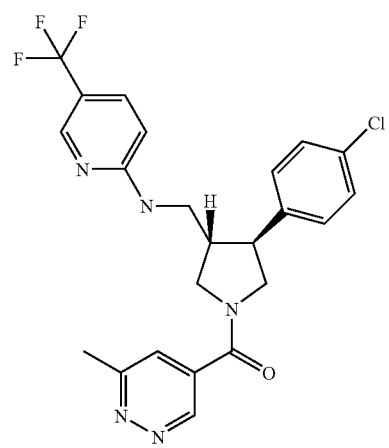

a) (3SR,4RS) [1-Benzyl-4-(4-chloro-phenyl)-pyrrolidin-3-ylmethyl]-(5-trifluoromethyl-pyridin-2-yl)-amine Nucleophilic substitution reaction according to General Procedure VI
Aniline derivative: 2-Amino-5-trifluoromethylpyridine (CAS RN: 74784-70-6)
Tosylate: (3SR,4RS) Toluene-4-sulfonic acid-1-benzyl-4-(4-chloro-phenyl)-pyrrolidin-3-ylmethyl ester
ES-MS m/e: 447.0 (M+H$^+$).

b) (3SR,4RS) [4-(4-Chloro-phenyl)-pyrrolidin-3-ylmethyl]-(5-trifluoromethyl-pyridin-2-yl)-amine Cleavage of the n-benzyl group according to General Procedure V
Amine: (3SR,4RS) [1-Benzyl-4-(4-chloro-phenyl)-pyrrolidin-3-ylmethyl]-(5-trifluoromethyl-pyridin-2-yl)-amine
ES-MS m/e: 356.9 (M+H$^+$).

c) (3SR,4RS) {3-(4-Chloro-phenyl)-4-[(5-trifluoromethyl-pyridin-2-ylamino)-methyl]-pyrrolidin-1-yl}-(6-methyl-pyridazin-4-yl)-methanone Amid coupling according to General procedure I
Amine: (3SR,4RS)[4-(4-Chloro-phenyl)-pyrrolidin-3-ylmethyl]-(5-trifluoromethyl-pyridin-2-yl)-amine
Carboxylic acid: 6-Methyl-pyridazine-4-carboxylic acid
ES-MS m/e: 476.2 (M+H$^+$).

EXAMPLE 43

(3SR,4RS) {3-(4-Chloro-phenyl)-4-[(5-trifluoromethyl-pyridin-2-ylamino)-methyl]-pyrrolidin-1-yl}-[1-(1-methyl-cyclopropanecarbonyl)-piperidin-4-yl]-methanone

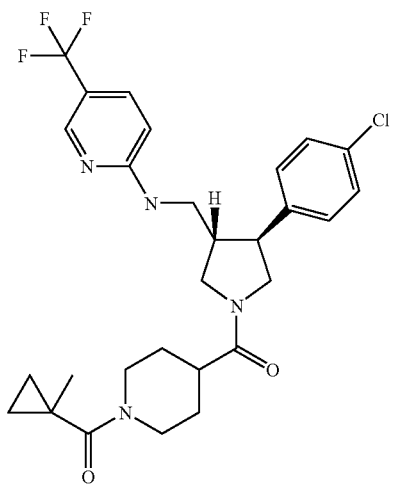

Amid coupling according to General procedure I
Amine: (3SR,4RS)[4-(4-Chloro-phenyl)-pyrrolidin-3-ylmethyl]-(5-trifluoromethyl-pyridin-2-yl)-amine
Carboxylic acid: 1-(1-Methyl-cyclopropanecarbonyl)-piperidine-4-carboxylic acid
ES-MS m/e: 549.3 (M+H$^+$).

EXAMPLE 44

(3SR,4RS) 6-{[4-(4-Chloro-phenyl)-1-(6-methyl-pyridazine-4-carbonyl)-pyrrolidin-3-ylmethyl]-amino}-nicotinonitrile

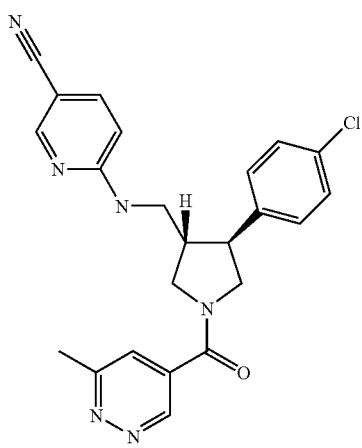

a) (3SR,4RS) 6-{[1-Benzyl-4-(4-chloro-phenyl)-pyrrolidin-3-ylmethyl]-amino}-nicotinonitrile Nucleophilic substitution reaction according to General Procedure VI
Aniline derivative: 2-Amino-5-cyanopyridine (CAS RN: 4214-73-7)
Tosylate: (3SR,4RS) Toluene-4-sulfonic acid-1-benzyl-4-(4-chloro-phenyl)-pyrrolidin-3-ylmethyl ester
ES-MS m/e: 404.1 (M+H$^+$).

b) (3SR,4RS) 6-{[4-(4-Chloro-phenyl)-pyrrolidin-3-ylmethyl]-amino}-nicotinonitrile Cleavage of the n-benzyl group according to General Procedure V
Amine: (3SR,4RS) 6-{[1-Benzyl-4-(4-chloro-phenyl)-pyrrolidin-3-ylmethyl]-amino}-nicotinonitrile
ES-MS m/e: 313.9 (M+H$^+$).

c) (3SR,4RS) 6-{[4-(4-Chloro-phenyl)-1-(6-methyl-pyridazine-4-carbonyl)-pyrrolidin-3-ylmethyl]-amino}-nicotinonitrile Amid coupling according to General procedure I
Amine: (3SR,4RS) 6-{[4-(4-Chloro-phenyl)-pyrrolidin-3-ylmethyl]-amino}-nicotinonitrile
Carboxylic acid: 6-Methyl-pyridazine-4-carboxylic acid
ES-MS m/e: 433.3 (M+H$^+$).

EXAMPLE 45

(3SR,4RS) 6-({4-(4-Chloro-phenyl)-1-[1-(1-methyl-cyclopropanecarbonyl)-piperidine-4-carbonyl]pyrrolidin-3-ylmethyl}-amino)-nicotinonitrile

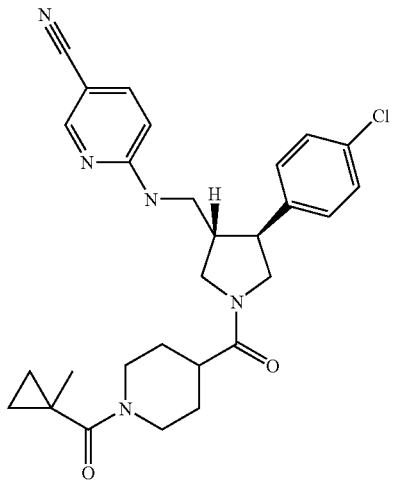

Amid coupling (pyrrolidine V, X or XV and carboxylic acid) according to General procedure I
Amine: (3SR,4RS) 6-{[4-(4-Chloro-phenyl)-pyrrolidin-3-ylmethyl]-amino}-nicotinonitrile
Carboxylic acid: 1-(1-Methyl-cyclopropanecarbonyl)-piperidine-4-carboxylic acid
ES-MS m/e: 506.3 (M+H$^+$).

Scheme 7:
Preparation of Intermediates XXXIII and XXXIV

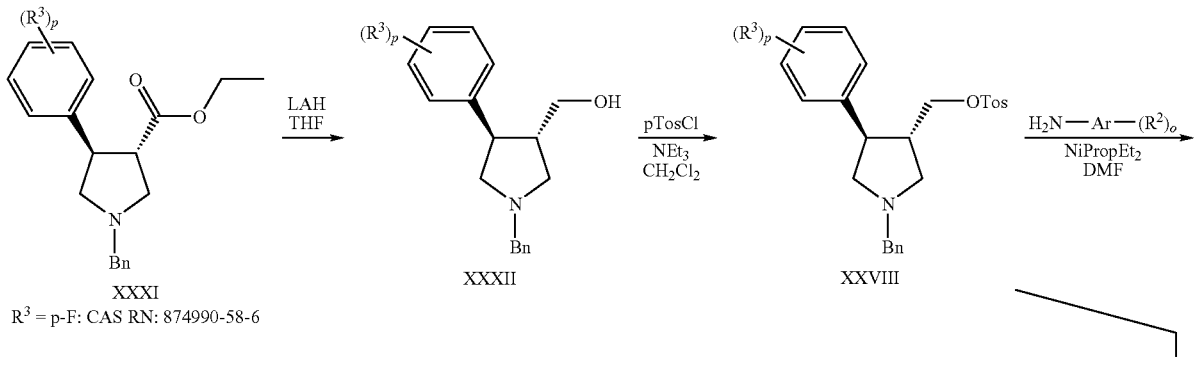

R$^3$ = p-F: CAS RN: 874990-58-6

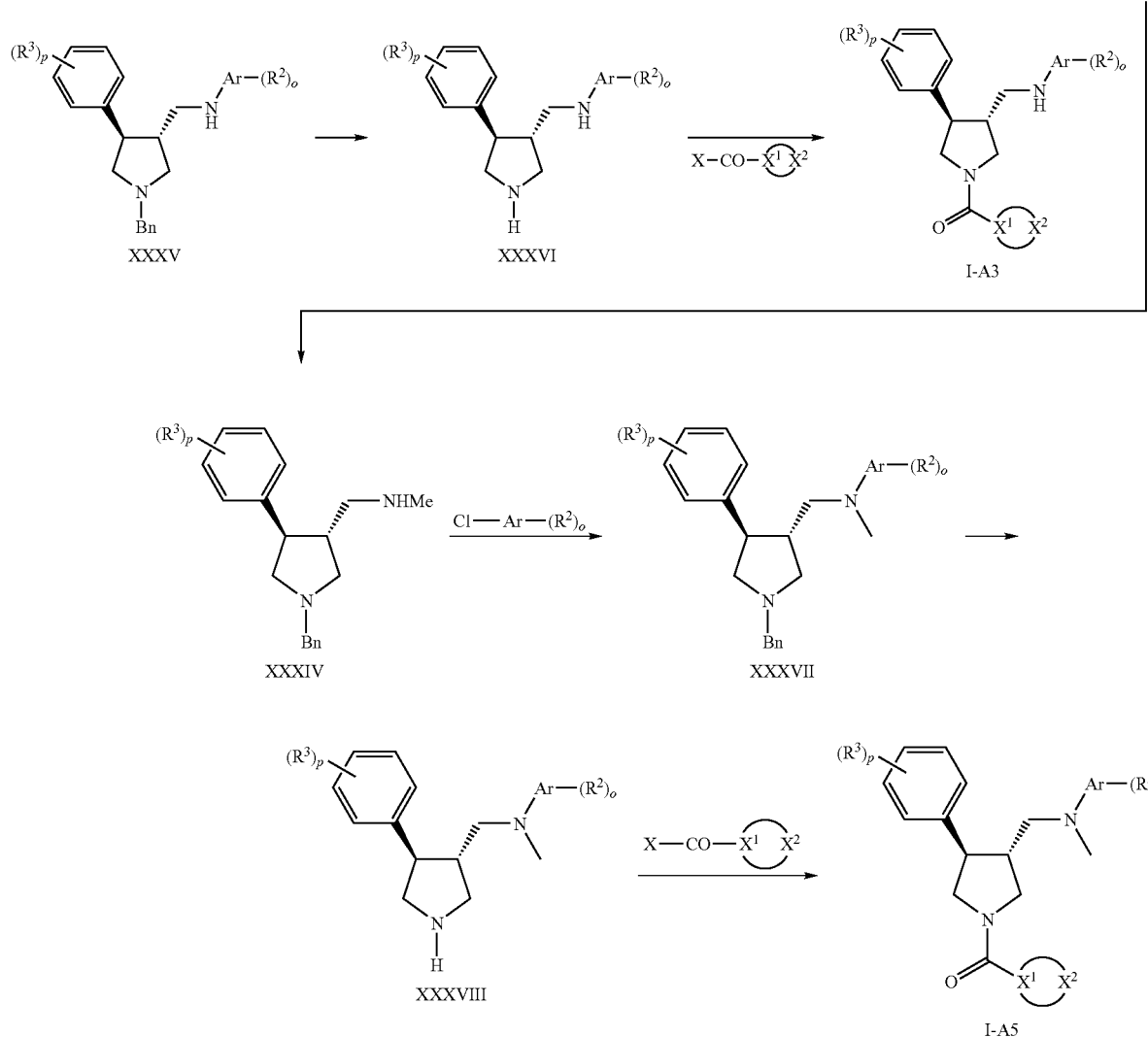

wherein $(R^3)_p$ is 4-F and the other substituents are as described above.

Preparation of (3SR,4RS) Toluene-4-sulfonic acid-1-benzyl-4-(4-fluoro-phenyl)-pyrrolidin-3-ylmethyl ester and (3SR,4RS)[1-Benzyl-4-(4-fluoro-phenyl)-pyrrolidin-3-ylmethyl]-methyl-amine

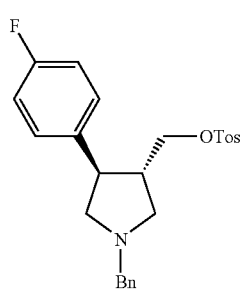

XXXIII a) (3SR,4RS) [1-Benzyl-4-(4-fluoro-phenyl)-pyrrolidin-3-yl]-methanol (3SR,4RS) 1-Benzyl-4-(4-fluoro-phenyl)-pyrrolidine-3-carboxylic acid ethyl ester (CAS RN: 874990-58-6) (20 g, 0.061 mol) were dissolved in THF (600 mL). At 0° C. LiAlH₄ (2.8 g, 0.073 mol) was added portion wise. After stirring at 0° C. for 4 h water (15 mL), then 5N NaOH (15 mL) and additional water (25 mL) was added. After stirring at ambient temperature for 1 h the mixture was extracted with ethyl acetate (3×50 mL), the combined organic phases were dried on sodium sulfate, filtered and evaporated. The crude title product was obtained as a light yellow oil (14.95 g, 86%) and directly used in the next step.

ES-MS m/e: 286.2 (M+H$^+$).

b) (3SR,4RS) Toluene-4-sulfonic acid-1-benzyl-4-(4-fluoro-phenyl)-pyrrolidin-3-ylmethyl ester (3SR,4RS) [1-Benzyl-4-(4-fluoro-phenyl)-pyrrolidin-3-yl]-methanol (14.95 g, 0.052 mmol) were dissolved in dichloro methane (200 mL) and cooled to 0° C. Then triethyl amine (10.15 mL, 0.073 mol) and p-TosCl (12.98 g, 0.068 mol) were added. The reaction mixture was allowed to slowly warm to ambient temperature and stirred over night. Then the volatiles were removed and the residue directly subjected to column chromatography (silica gel, heptane, heptane/ethyl acetate 9:1/4:1/1:1) to yield the title product (10.8 g, 47%) as a light yellow oil.

ES-MS m/e: 440.3 (M+H$^+$).

c) (3SR,4RS)[1-Benzyl-4-(4-fluoro-phenyl)-pyrrolidin-3-ylmethyl]-methyl-amine (3SR,4RS) Toluene-4-sulfonic acid-1-benzyl-4-(4-fluoro-phenyl)-pyrrolidin-3-ylmethyl ester (5.0 g, 0.011 mmol) were dissolved in 2.0 M solution of MeNH$_2$ in THF (36 mL) in an autoclave and heated to 80° C. over night. The volatiles were removed and the crude product subjected to column chromatography (silica gel, dichloro methane, dichloro methane/methanol →4:1) to yield the title compound (2.6 g, 76%) as a light yellow oil.

ES-MS m/e: 299.3 (M+H$^+$).

EXAMPLE 46

(3SR,4RS) {3-(4-Fluoro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone

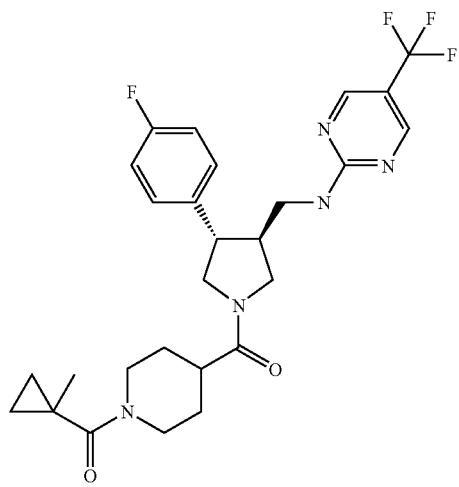

a) (3SR,4RS) [1-Benzyl-4-(4-fluoro-phenyl)-pyrrolidin-3-ylmethyl]-(5-trifluoromethyl-pyrimidin-2-yl)-amine Nucleophilic substitution reaction according to General Procedure VI
Aniline derivative: 2-Amino-5-trifluoromethylpyrimidine (CAS RN:69034-08-8)
Tosylate: (3SR,4RS) Toluene-4-sulfonic acid-1-benzyl-4-(4-fluoro-phenyl)-pyrrolidin-3-ylmethyl ester
ES-MS m/e: 431.5 (M+H$^+$).

b) (3SR,4RS) [4-(4-Fluoro-phenyl)-pyrrolidin-3-ylmethyl]-(5-trifluoromethyl-pyrimidin-2-yl)-amine Cleavage of the n-benzyl group according to General Procedure V
Amine: (3SR,4RS) [1-Benzyl-4-(4-fluoro-phenyl)-pyrrolidin-3-ylmethyl]-(5-trifluoromethyl-pyrimidin-2-yl)-amine
ES-MS m/e: 341.3 (M+H$^+$).

c) (3SR,4RS) {3-(4-Fluoro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone Amid coupling according to General procedure I
Amine: (3SR,4RS) [4-(4-Fluoro-phenyl)-pyrrolidin-3-ylmethyl]-(5-trifluoromethyl-pyrimidin-2-yl)-amine
Carboxylic acid: 1-(1-Methyl-cyclopropanecarbonyl)-piperidine-4-carboxylic acid
ES-MS m/e: 534.2 (M+H$^+$).

EXAMPLE 47

(3SR,4RS) [4-(3-(4-Fluoro-phenyl)-4-{[methyl-(5-trifluoromethyl-pyrimidin-2-yl)-amino]-methyl}-pyrrolidine-1-carbonyl)-piperidin-1-yl]-(1-methyl-cyclopropyl)-methanone

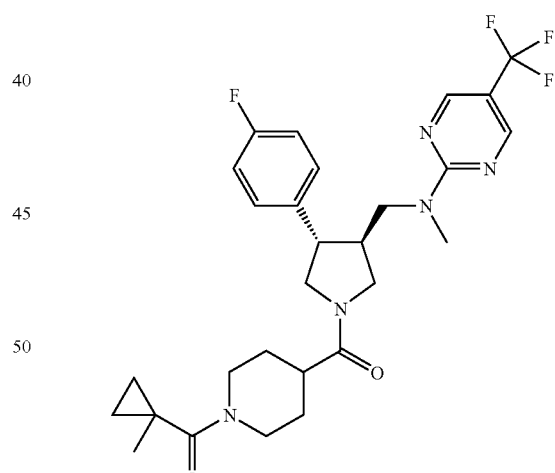

a) [(3SR,4RS)-1-Benzyl-4-(4-fluoro-phenyl)-pyrrolidin-3-ylmethyl]-methyl-(5-trifluoromethyl-pyrimidin-2-yl)-amine Nucleophilic aromatic substitution according to General Procedure IV:
Amine: (3SR,4RS)[1-Benzyl-4-(4-fluoro-phenyl)-pyrrolidin-3-ylmethyl]-methyl-amine
Heteroaromatic methylsulfone: 2-Methanesulfonyl-5-trifluoromethyl-pyrimidine (CAS RN: 361389-88-0)
ES-MS m/e: 445.2 (M+H$^+$).

b) [(3SR,4RS)-4-(4-Fluoro-phenyl)-pyrrolidin-3-ylmethyl]-methyl-(5-trifluoromethyl-pyrimidin-2-yl)-amine Cleavage of the n-benzyl group according to General Procedure V
Amine: (3SR,4RS) [1-Benzyl-4-(4-fluoro-phenyl)-pyrrolidin-3-ylmethyl]-methyl-(5-trifluoromethyl-pyrimidin-2-yl)-amine
ES-MS m/e: 355.2 (M+H⁺).

c) (3SR,4RS) [4-(3-(4-Fluoro-phenyl)-4-{[methyl-(5-trifluoromethyl-pyrimidin-2-yl)-amino]-methyl}-pyrrolidine-1-carbonyl)-piperidin-1-yl]-(1-methyl-cyclopropyl)-methanone Amid coupling according to General procedure I
Amine: (3SR,4RS) [4-(4-Fluoro-phenyl)-pyrrolidin-3-ylmethyl]-methyl-(5-trifluoromethyl-pyrimidin-2-yl)-amine
Carboxylic acid: 1-(1-Methyl-cyclopropanecarbonyl)-piperidine-4-carboxylic acid
ES-MS m/e: 548.3 (M+H⁺).

EXAMPLE 48

(3SR,4RS) (3-(4-Fluoro-phenyl)-4-{[methyl-(5-trifluoromethyl-pyridin-2-yl)-amino]-methyl}-pyrrolidin-1-yl)-[1-(1-methyl-cyclopropanecarbonyl)-piperidin-4-yl]-methanone

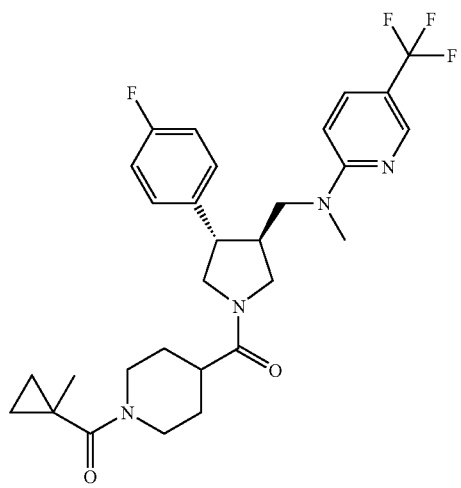

a) [(3SR,4RS)-1-Benzyl-4-(4-fluoro-phenyl)-pyrrolidin-3-ylmethyl]-methyl-(5-trifluoromethyl-pyridin-2-yl)-amine Nucleophilic aromatic substitution according to General Procedure IV:
Amine: (3SR,4RS)[1-Benzyl-4-(4-fluoro-phenyl)-pyrrolidin-3-ylmethyl]-methyl-amine
Heteroaromatic methylsulfone: 2-Methanesulfonyl-5-trifluoromethyl-pyrimidine
ES-MS m/e: 444.5 (M+H⁺).

b) [(3SR,4RS)-4-(4-Fluoro-phenyl)-pyrrolidin-3-ylmethyl]-methyl-(5-trifluoromethyl-pyridin-2-yl)-amine Cleavage of the n-benzyl group according to General Procedure V
Amine: (3SR,4RS) [1-Benzyl-4-(4-fluoro-phenyl)-pyrrolidin-3-ylmethyl]-methyl-(5-trifluoromethyl-pyridin-2-yl)-amine
ES-MS m/e: 354.2 (M+H⁺).

c) (3SR,4RS) (3-(4-Fluoro-phenyl)-4-{[methyl-(5-trifluoromethyl-pyridin-2-yl)-amino]-methyl}-pyrrolidin-1-yl)-[1-(1-methyl-cyclopropanecarbonyl)-piperidin-4-yl]-methanone Amid coupling according to General procedure I
Amine: (3SR,4RS) [4-(4-Fluoro-phenyl)-pyrrolidin-3-ylmethyl]-methyl-(5-trifluoromethyl-pyridin-2-yl)-amine
Carboxylic acid: 1-(1-Methyl-cyclopropanecarbonyl)-piperidine-4-carboxylic acid
ES-MS m/e: 547.3 (M+H⁺).

Scheme 8:
Preparation of Intermediate XLV

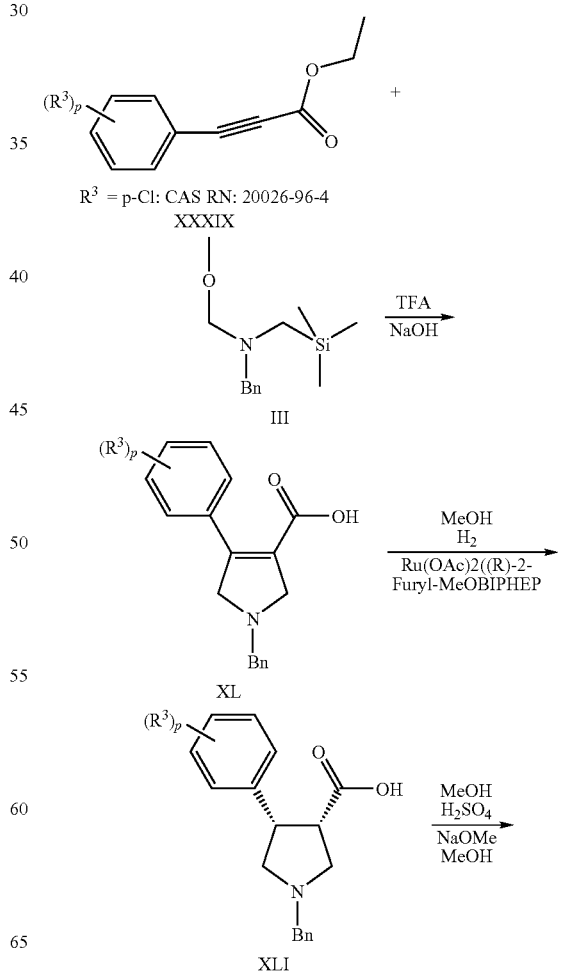

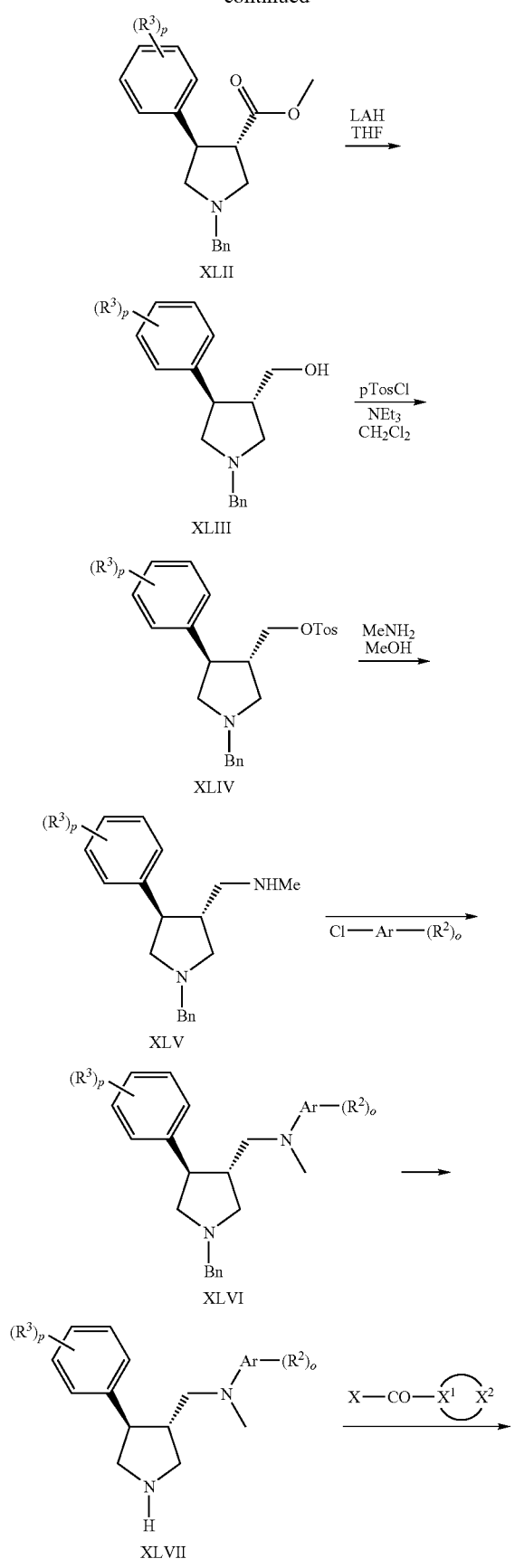

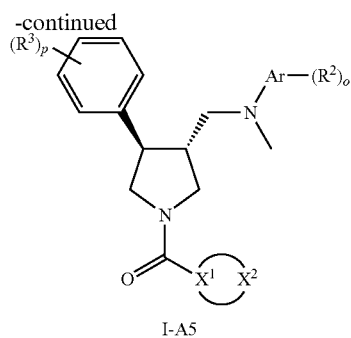

wherein $(R^3)_p$ is 4-Cl and the other substituents are as described above.

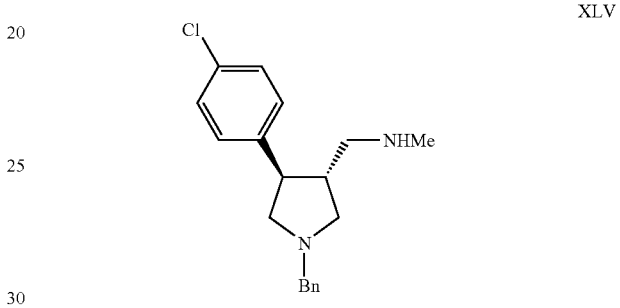

a) 1-Benzyl-4-(4-chloro-phenyl)-2,5-dihydro-1H-pyrrole-3-carboxylic acid

A solution of N-(methoxymethyl)-N-(phenylmethyl)-N-(trimethylsilyl)methylamine (201.6 g, 849 mmol) in $CH_2Cl_2$ (600 mL) was added dropwise over a 30 minutes period to a stirred solution of 3-(4-chlorophenyl)-2-propionic acid ethyl ester (125.9 g, 566 mmol) and trifluoroacetic acid (4.3 mL, 114 mmol) in $CH_2Cl_2$ (400 mL) at 0° C. The ice bath was removed, and the solution was stirred at 25° C. for an additional 4 h. It was then concentrated and the reaction mixture was taken up in dioxane (1.2 L). Then 1N NaOH (146 mL) were added and the mixture was stirred at ambient temperature for 72 h. The volatiles were removed and the residue was extracted with TBDME and water. The organic phases were extracted with water and the combined aqueous phases were acidified with aqueous HCl (10%). Upon stirring at ambient temperature over night a precipitation formed which was isolated, washed with water and ethanol and dried under high vacuum to yield the title product (148 g, 76%) as a colorless solid. ES-MS m/e: 314.8 (M+H$^+$).

b) (3S,4S)-1-Benzyl-4-(4-chloro-phenyl)-pyrrolidine-3-carboxylic acid

A 185-ml stainless steel autoclave was charged under argon in a glove box ($O_2$ content<2 ppm) with 1-benzyl-4-(4-chloro-phenyl)-2,5-dihydro-1H-pyrrole-3-carboxylic acid (5.00 g, 15.1 mmol), [Ru(OAc)$_2$((R)-2-Furyl-MeOBIPHEP] (3.8 mg, 5.0 µmol) (S/C 5'000) and methanol (150 mL). The asymmetric hydrogenation was run under 40 bar of hydrogen for 20 h at 30° C. and additional 2 h at 60° C. to complete the conversion (>99.6% conversion and 99.9% ee). After the pressure was released, the white suspension was stirred at 0-5° C. for 2 h, filtered off and the filter cake was washed with cold (0-5° C.) methanol (20 mL) and dried under vacuum at room temperature to yield the title product (4.75 g, 99%) with 99% purity and 99.9% ee. ES-MS m/e: 316.1 (M+H⁺).

c) (3S,4S)-1-Benzyl-4-(4-chloro-phenyl)-pyrrolidine-3-carboxylic acid methyl ester (3S,4S)-1-Benzyl-4-(4-chloro-phenyl)-pyrrolidine-3-carboxylic acid (7.0 g, 22.0 mmol) were dissolved in methanol (75 mL) and at ambient temperature treated with sulfuric acid 97% (2.4 mL). The reaction mixture was stirred at 60° C. for 18 h. At 0° C. dichloro methane (150 mL) was added followed by aqueous sodium carbonate 10% (150 mL) (final pH 11) under vigorous stirring. The phases were separated. The aqueous phase was washed with dichloro methane, the combined organic phases with water and brine and then dried on sodium sulfate. After filtration and evaporation of the solvent the title product was obtained as a light brown oil (7.0 g, 96%) which was directly used in the next step. ES-MS m/e: 330.8 (M+H⁺).

d) (3R,4S)-1-Benzyl-4-(4-chloro-phenyl)-pyrrolidine-3-carboxylic acid methyl ester (3S,4S)-1-Benzyl-4-(4-chloro-phenyl)-pyrrolidine-3-carboxylic acid methyl ester (7.0 g, 21.0 mmol) were dissolved in methanol (60 mL) and treated with NaOMe (30% in methanol, 0.9 mL, 4.50 mmol) for 24 h at ambient temperature. The volatiles were removed and the residue was subjected to column chromatography (silica gel, heptane/ethyl acetate 9:1) to yield the title compound (5.9 g, 84%) as a colorless oil. ES-MS m/e: 330.8 (M+H⁺).

e) [(3R,4S)-1-Benzyl-4-(4-chloro-phenyl)-pyrrolidin-3-yl]-methanol (3R,4S)-1-Benzyl-4-(4-chloro-phenyl)-pyrrolidine-3-carboxylic acid methyl ester (5.8 g, 0.018 mol) were dissolved in THF (180 mL). At 0° C. LiAlH₄ (0.70 g, 0.0185 mol) was added portion wise. After stirring at 0° C. for 4 h water (5 mL), then 5N NaOH (5 mL) and additional water (15 mL) was added. After stirring at ambient temperature for 30 min the mixture was extracted with ethyl acetate (3×10 mL), the combined organic phases were dried on sodium sulfate, filtered and evaporated. The crude title product was obtained as a light yellow oil (5.2 g, 98%) and directly used in the next step. ES-MS m/e: 302.8 (M+H⁺).

f) Toluene-4-sulfonic acid (3R,4S)-1-benzyl-4-(4-chloro-phenyl)-pyrrolidin-3-ylmethyl ester

[(3R,4S)-1-Benzyl-4-(4-chloro-phenyl)-pyrrolidin-3-yl]-methanol (5.2 g, 17.0 mmol) were dissolved in dichloro methane (80 mL) and cooled to 0° C. Then triethyl amine (3.34 mL, 24.0 mmol) and p-TosCl (4.27 g, 22.0 mmol) were added. The reaction mixture was allowed to slowly warm to ambient temperature and stirred over night. Then the volatiles were removed and the residue directly subjected to column chromatography (silica gel, heptane, heptane/ethyl acetate 9:1/4:1) to yield the title product (5.2 g, 66%) as a colorless oil.
ES-MS m/e: 457.1 (M+H⁺).

g) [3S,4S)-1-Benzyl-4-(4-chloro-phenyl)-pyrrolidin-3-ylmethyl]-methyl-amine Toluene-4-sulfonic acid (3R,4S)-1-benzyl-4-(4-chloro-phenyl)-pyrrolidin-3-ylmethyl ester (4.0 g, 0.009 mmol) were dissolved in a 2.0 M solution of MeNH₂ in THF (31 mL) in an autoclave and heated to 80° C. over night. The volatiles were removed and the crude product subjected to column chromatography (silica gel, heptane/ethyl acetate 1:1) to yield the title compound (2.25 g, 81%) as a colorless oil.
ES-MS m/e: 315.9 (M+H⁺).

EXAMPLE 49

((3S,4S)-3-(4-Chloro-phenyl)-4-{[(5-chloro-pyridin-2-yl)-methyl-amino]-methyl}-pyrrolidin-1-yl)-[1-(1-methyl-cyclopropanecarbonyl)-piperidin-4-yl]-methanone

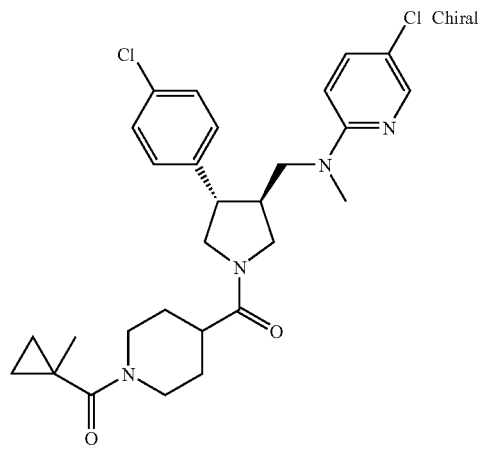

a) [(3R,4S)-1-Benzyl-4-(4-chloro-phenyl)-pyrrolidin-3-ylmethyl]-(5-chloro-pyridin-2-yl)-methyl-amine Nucleophilic aromatic substitution according to General Procedure IV:
Amine: [(3S,4S)-1-Benzyl-4-(4-chloro-phenyl)-pyrrolidin-3-ylmethyl]-methyl-amine
Heteroaromatic methylsulfone: 2,5-Dichloro-pyridine
ES-MS m/e: 427.5 (M+H⁺).

b) [(3R,4S)-4-(4-Chloro-phenyl)-pyrrolidin-3-ylmethyl]-(5-chloro-pyridin-2-yl)-methyl-amine Cleavage of the n-benzyl group according to General Procedure V
Amine: [(3R,4S)-1-Benzyl-4-(4-chloro-phenyl)-pyrrolidin-3-ylmethyl]-(5-chloro-pyridin-2-yl)-methyl-amine
ES-MS m/e: 355.2 (M+H⁺).

c) ((3S,4S)-3-(4-Chloro-phenyl)-4-{[(5-chloro-pyridin-2-yl)-methyl-amino]-methyl}-pyrrolidin-1-yl)-[1-(1-methyl-cyclopropanecarbonyl)-piperidin-4-yl]-methanone Amid coupling according to General procedure I
Amine: [(3R,4S)-4-(4-Chloro-phenyl)-pyrrolidin-3-ylmethyl]-(5-chloro-pyridin-2-yl)-methyl-amine
Carboxylic acid: 1-(1-Methyl-cyclopropanecarbonyl)-piperidine-4-carboxylic acid
ES-MS m/e: 529.2 (M+H⁺).

EXAMPLE 50

((3S,4S)-3-(4-Chloro-phenyl)-4-{[(5-chloro-pyridin-2-yl)-methyl-amino]-methyl}-pyrrolidin-1-yl)-(6-methyl-pyridazin-4-yl)-methanone

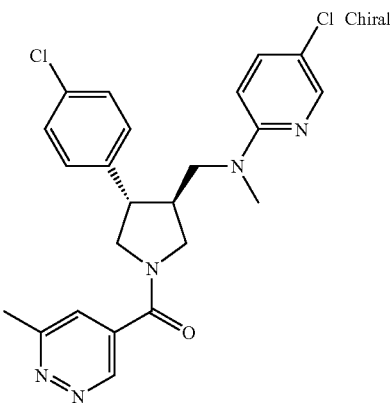

Amid coupling according to General procedure I
Amine: [(3R,4S)-4-(4-Chloro-phenyl)-pyrrolidin-3-ylmethyl]-(5-chloro-pyridin-2-yl)-methyl-amine
Carboxylic acid: 6-Methyl-pyridazine-4-carboxylic acid
ES-MS m/e: 456.3 (M+H$^+$).

EXAMPLE 51

6-({(3S,4S)-4-(4-Chloro-phenyl)-1-[1-(1-methyl-cyclopropanecarbonyl)-piperidine-4-carbonyl]-pyrrolidin-3-ylmethyl}-methyl-amino)-nicotinonitrile

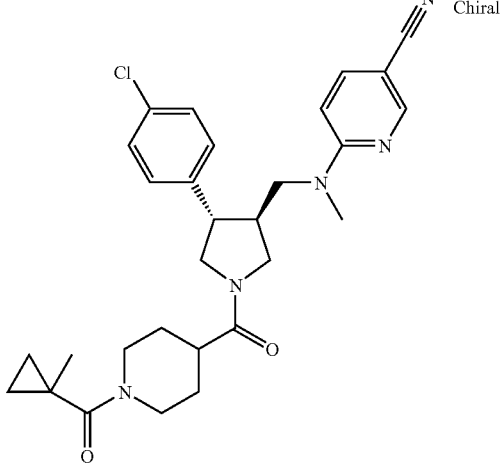

a) 6-{[(3R,4S)-1-Benzyl-4-(4-chloro-phenyl)-pyrrolidin-3-ylmethyl]-methyl-amino}-nicotinonitrile Nucleophilic aromatic substitution according to General Procedure IV:
Amine: [(3S,4S)-1-Benzyl-4-(4-chloro-phenyl)-pyrrolidin-3-ylmethyl]-methyl-amine
Heteroaromatic chloride: 6-Chloro-3-pyridine carbonitrile (CAS RN: 33252-28-7)
ES-MS m/e: 427.5 (M+H$^+$).

b) 6-{[(3R,4S)-4-(4-Chloro-phenyl)-pyrrolidin-3-ylmethyl]-methyl-amino}-nicotinonitrile Cleavage of the n-benzyl group according to General Procedure V
Amine: 6-{[(3R,4 S)-1-Benzyl-4-(4-chloro-phenyl)-pyrrolidin-3-ylmethyl]-methyl-amino}-nicotinonitrile
ES-MS m/e: 327.92 (M+H$^+$).

c) 6-({(3S,4S)-4-(4-Chloro-phenyl)-1-[1-(1-methyl-cyclopropanecarbonyl)-piperidine-4-carbonyl]-pyrrolidin-3-ylmethyl}-methyl-amino)-nicotinonitrile Amid coupling according to General procedure I
Amine: 6-{[(3R,4S)-4-(4-Chloro-phenyl)-pyrrolidin-3-ylmethyl]-methyl-amino}-nicotinonitrile
Carboxylic acid: 1-(1-Methyl-cyclopropanecarbonyl)-piperidine-4-carboxylic acid
ES-MS m/e: 520.3 (M+H$^+$).

EXAMPLE 52

6-{[3S,4S)-4-(4-Chloro-phenyl)-1-(6-methyl-pyridazine-4-carbonyl)-pyrrolidin-3-ylmethyl]-methyl-amino}-nicotinonitrile

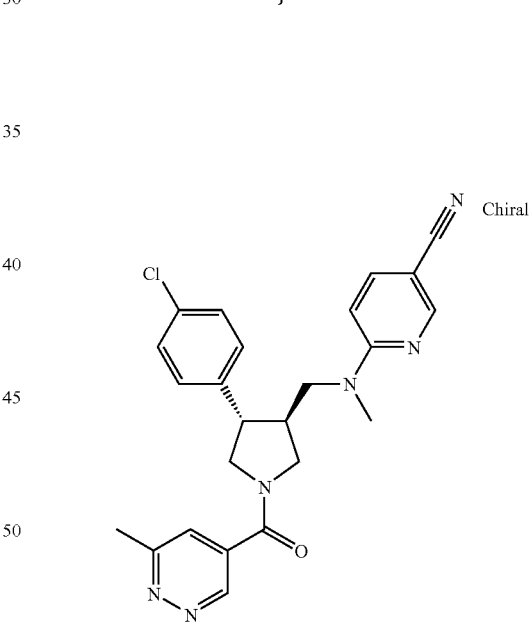

Amid coupling according to General procedure I
Amine: 6-{[(3R,4S)-4-(4-Chloro-phenyl)-pyrrolidin-3-ylmethyl]-methyl-amino}-nicotinonitrile
Carboxylic acid: 6-Methyl-pyridazine-4-carboxylic acid
ES-MS m/e: 447.2 (M+H$^+$).

EXAMPLE 53

[4-((3S,4S)-3-(4-Chloro-phenyl)-4-{[methyl-(5-trif-luoromethyl-pyridin-2-yl)-amino]-methyl}-pyrrolidine-1-carbonyl)-piperidin-1-yl]-(1-methyl-cyclopropyl)-methanone

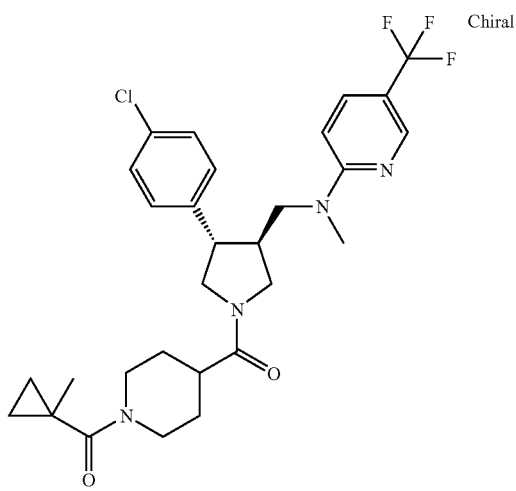

a) [(3R,4S)-1-Benzyl-4-(4-chloro-phenyl)-pyrrolidin-3-ylmethyl]-methyl-(5-trifluoromethyl-pyridin-2-yl)-amine Nucleophilic aromatic substitution according to General Procedure IV:
Amine: [(3S,4S)-1-Benzyl-4-(4-chloro-phenyl)-pyrrolidin-3-ylmethyl]-methyl-amine
Hetero aromatic chloride: 2-Chloro-5-trifluoromethylpyridine (CAS RN: 52334-81-3)
ES-MS m/e: 461.0 (M+H⁺).

b) [(3R,4S)-4-(4-Chloro-phenyl)-pyrrolidin-3-ylmethyl]-methyl-(5-trifluoromethyl-pyridin-2-yl)-amine Cleavage of the n-benzyl group according to General Procedure V
Amine: [(3R,4S)-1-Benzyl-4-(4-chloro-phenyl)-pyrrolidin-3-ylmethyl]-methyl-(5-trifluoromethyl-pyridin-2-yl)-amine
ES-MS m/e: 370.9 (M+H⁺).

c) [4-((3S,4S)-3-(4-Chloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone Amid coupling according to General procedure I
Amine: [(3R,4S)-4-(4-Chloro-phenyl)-pyrrolidin-3-ylmethyl]-methyl-(5-trifluoromethyl-pyridin-2-yl)-amine
Carboxylic acid: 1-(1-Methyl-cyclopropanecarbonyl)-piperidine-4-carboxylic acid
ES-MS m/e: 563.3 (M+H⁺).

EXAMPLE 54

((3S,4S)-3-(4-Chloro-phenyl)-4-{[methyl-(5-trifluoromethyl-pyridin-2-yl)-amino]-methyl}-pyrrolidin-1-yl)-(6-methyl-pyridazin-4-yl)-methanone

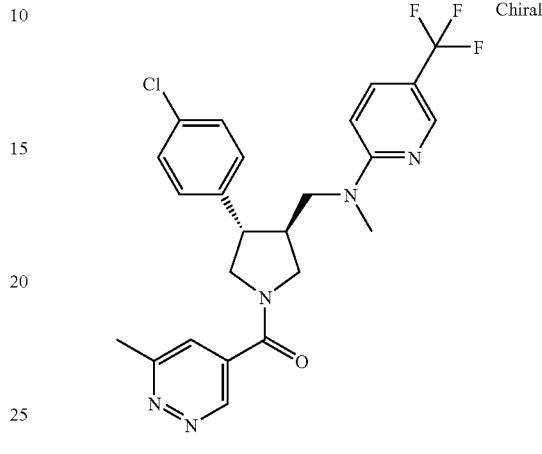

Amid coupling according to General procedure I
Amine: [(3R,4S)-4-(4-Chloro-phenyl)-pyrrolidin-3-ylmethyl]-methyl-(5-trifluoromethyl-pyridin-2-yl)-amine
Carboxylic acid: 6-Methyl-pyridazine-4-carboxylic acid
ES-MS m/e: 490.1 (M+H⁺).

EXAMPLE 55

((3S,4S)-3-(4-Chloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone

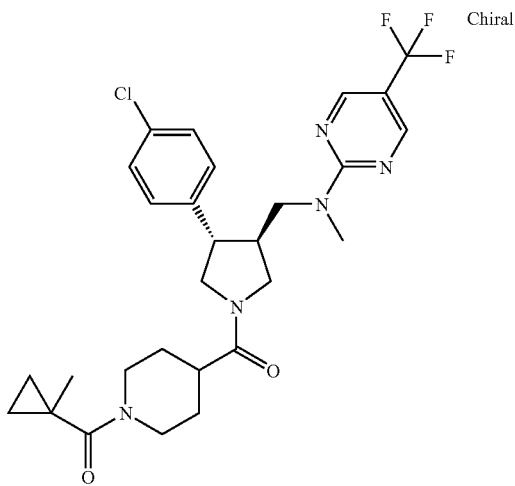

a) [(3R,4S)-1-Benzyl-4-(4-chloro-phenyl)-pyrrolidin-3-ylmethyl]-methyl-(5-trifluoromethyl-pyrimidin-2-yl)-amine Nucleophilic aromatic substitution according to General Procedure IV:
Amine: [(3S,4S)-1-Benzyl-4-(4-chloro-phenyl)-pyrrolidin-3-ylmethyl]-methyl-amine
Heteroaromatic methylsulfone: 2-Methanesulfonyl-5-trifluoromethyl-pyrimidine (CAS RN: 361389-88-0)
ES-MS m/e: 462.0 (M+H$^+$).

b) [(3R,4S)-4-(4-Chloro-phenyl)-pyrrolidin-3-ylmethyl]-methyl-(5-trifluoromethyl-pyrimidin-2-yl)-amine Cleavage of the n-benzyl group according to General Procedure V
Amine: [(3R,4S)-1-Benzyl-4-(4-chloro-phenyl)-pyrrolidin-3-ylmethyl]-methyl-(5-trifluoromethyl-pyrimidin-2-yl)-amine
ES-MS m/e: 371.9 (M+H$^+$).

c) ((3S,4S)-3-(4-Chloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone Amid coupling according to General procedure I
Amine: [(3R,4S)-4-(4-Chloro-phenyl)-pyrrolidin-3-ylmethyl]-methyl-(5-trifluoromethyl-pyrimidin-2-yl)-amine
Carboxylic acid: 1-(1-Methyl-cyclopropanecarbonyl)-piperidine-4-carboxylic acid
ES-MS m/e: 564.3 (M+H$^+$).

EXAMPLE 56

((3S,4S)-3-(4-Chloro-phenyl)-4-{[methyl-(5-trifluoromethyl-pyrimidin-2-yl)-amino]-methyl}-pyrrolidin-1-yl)-(6-methyl-pyridazin-4-yl)-methanone

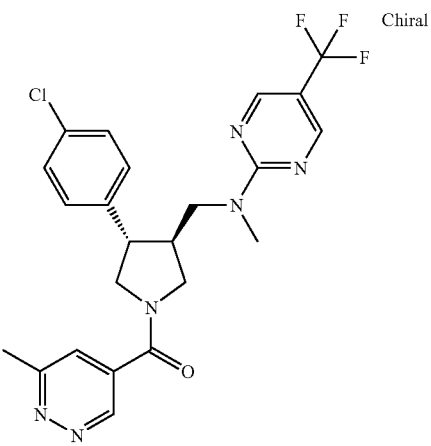

Amid coupling according to General procedure I
Amine: [(3R,4S)-4-(4-Chloro-phenyl)-pyrrolidin-3-ylmethyl]-methyl-(5-trifluoromethyl-pyrimidin-2-yl)-amine
Carboxylic acid: 6-Methyl-pyridazine-4-carboxylic acid
ES-MS m/e: 491.3 (M+H$^+$).

Scheme 9:
Preparation of Intermediates LIV +LVII

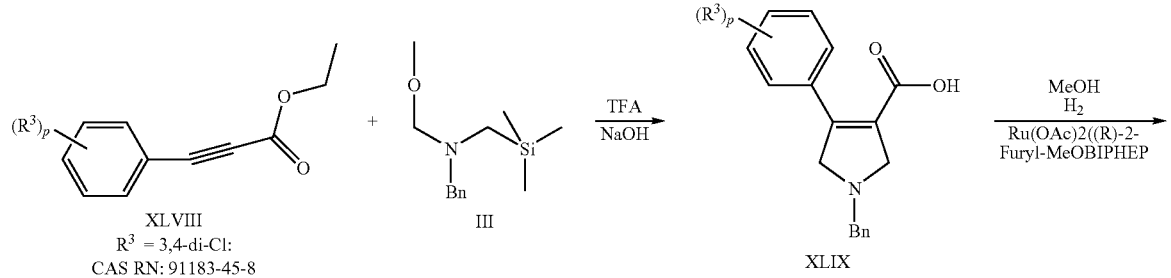

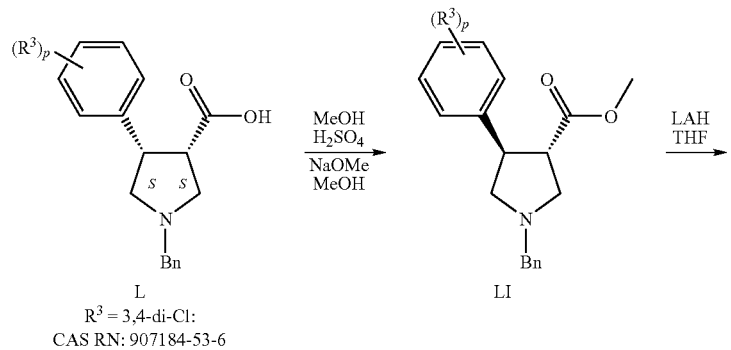

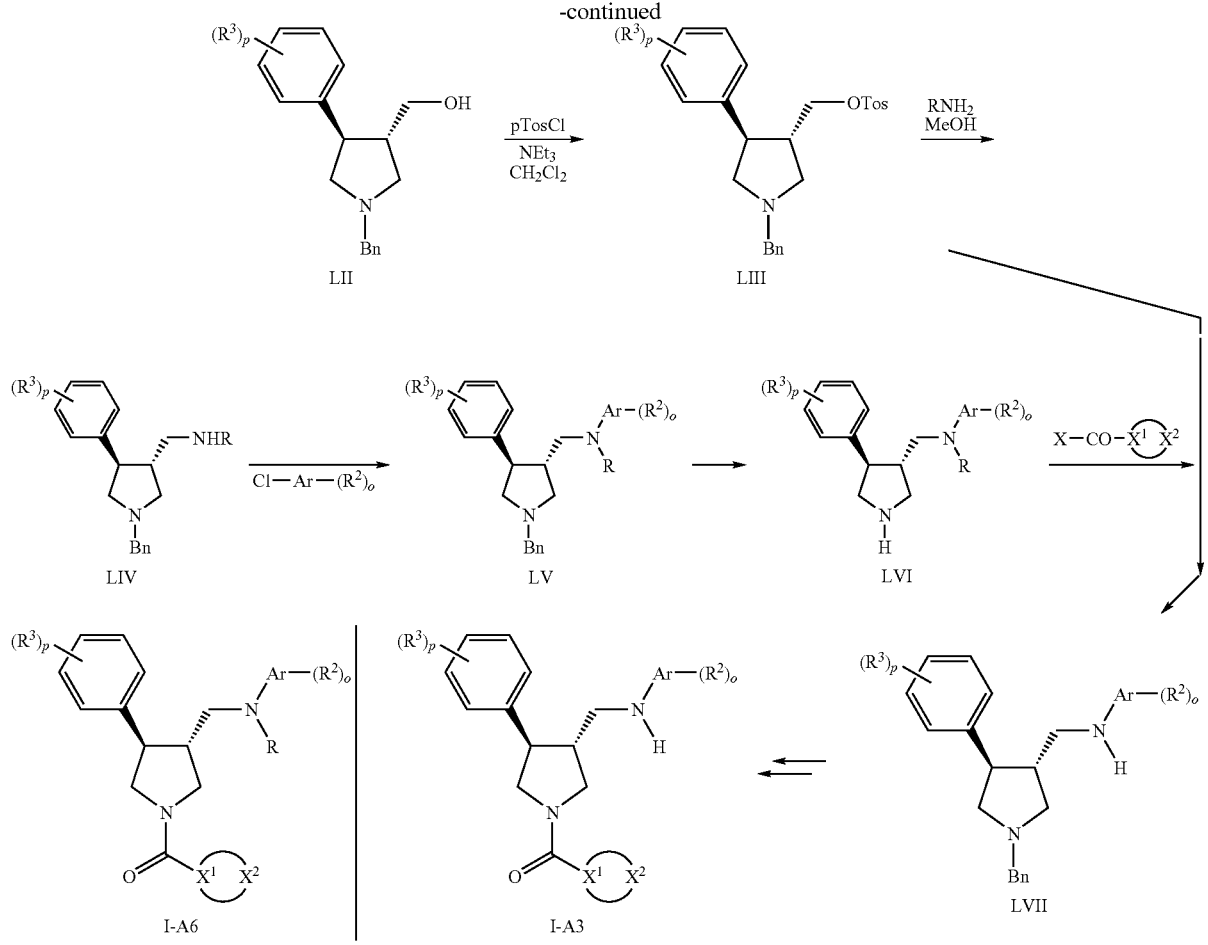

wherein $(R^3)_p$ is 3,4-di-Cl and the other substituents are as described above.

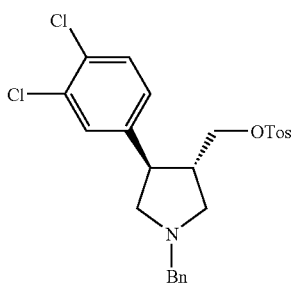

LIII

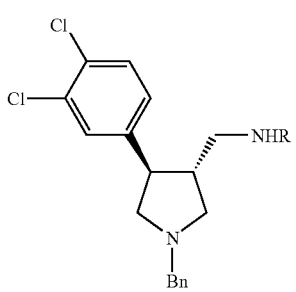

LIV a) (3S,4S)-1-Benzyl-4-(3,4-dichloro-phenyl)-pyrrolidine-3-carboxylic acid methyl ester (3S,4S)-1-Benzyl-4-(3,4-dichloro-phenyl)-pyrrolidine-3-carboxylic acid (CAS RN: 907184-53-6) (35.7 g, 0.102 mol) were dissolved in methanol (350 mL) and at ambient temperature treated with sulfuric acid 97% (10.9 mL). The reaction mixture was stirred at 60° C. for 18 h. At 0° C. dichloro methane (500 mL) was added followed by aqueous sodium carbonate 10% (500 mL) (final pH 11) under vigorous stirring. The phases were separated. The aqueous phase was washed with dichloro methane, the combined organic phases with water and brine and then dried on sodium sulfate. After filtration and evaporation of the solvent the title product was obtained as a yellow oil (36.3 g, 98%) which was directly used in the next step. ES-MS m/e: 365.3 (M+H$^+$).

b) (3R,4S)-1-Benzyl-4-(3,4-dichloro-phenyl)-pyrrolidine-3-carboxylic acid methyl ester (3S,4S)-1-Benzyl-4-(3,4-dichloro-phenyl)-pyrrolidine-3-carboxylic acid methyl ester (37.5 g, 0.107 mol) were dissolved in methanol (300 mL) and treated with NaOMe (30% in methanol, 2.97 mL, 0.016 mol) for 24 h at ambient temperature. The volatiles were removed and the residue was subjected to column chromatography (silica gel, heptane/ethyl acetate 9:1) to yield the title compound (32.0 g, 82%) as a colorless oil. ES-MS m/e: 365.3 (M+H$^+$).

c) [(3R,4S)-1-Benzyl-4-(3,4-dichloro-phenyl)-pyrrolidin-3-yl]-methanol (3R,4S)-1-Benzyl-4-(3,4-dichloro-phenyl)-pyrrolidine-3-carboxylic acid methyl ester (28.5 g, 0.078 mol) were dissolved in THF (800 mL). At 0° C. LiAlH$_4$ (3.12 g, 0.082 mol) was added portion wise. After stirring at 0° C. for 4 h water (20 mL), then 5N NaOH (20 mL) and additional water (30 mL) was added. After stirring at ambient temperature for 30 min the mixture was extracted with ethyl acetate (3×10 mL), the combined organic phases were dried on sodium sulfate, filtered and evaporated. The crude title product was obtained as a white solid (25.0 g, 95%) and directly used in the next step. ES-MS m/e: 337.8 (M+H$^+$).

d) Toluene-4-sulfonic acid (3R,4S)-1-benzyl-4-(3,4-dichloro-phenyl)-pyrrolidin-3-ylmethyl ester

[(3R,4S)-1-Benzyl-4-(3,4-dichloro-phenyl)-pyrrolidin-3-yl]-methanol (55.0 g, 0.164 mmol) were dissolved in dichloro methane (800 mL) and cooled to 0° C. Then triethyl amine (31.74 mL, 0.24 mol) and p-TosCl (40.54 g, 0.213 mol) were added. The reaction mixture was allowed to slowly warm to ambient temperature and stirred over night. Then the volatiles were removed and the residue directly subjected to column chromatography (silica gel, heptane, heptane/ethyl acetate 9:1/4:1) to yield the title product (62 g, 77%) as a white solid. ES-MS m/e: 491.1 (M+H$^+$).

e) [(3S,4S)-1-Benzyl-4-(3,4-dichloro-phenyl)-pyrrolidin-3-ylmethyl]-methyl-amine Toluene-4-sulfonic acid (3R,4S)-1-benzyl-4-(3,4-dichloro-phenyl)-pyrrolidin-3-ylmethyl ester (5.0 g, 0.0102 mmol) were dissolved in 2.0 M solution of MeNH$_2$ in THF (35 mL) in an autoclave and heated to 80° C. over night. The volatiles were removed and the crude product subjected to column chromatography (silica gel, dichloro methane/methanol 0->20%) to yield the title compound (3.25 g, 91%) as a light yellow oil.

ES-MS m/e: 349.2 (M+H$^+$).

f) [(3S,4S)-1-Benzyl-4-(3,4-dichloro-phenyl)-pyrrolidin-3-ylmethyl]-ethyl-amine Toluene-4-sulfonic acid (3R,4S)-1-benzyl-4-(3,4-dichloro-phenyl)-pyrrolidin-3-ylmethyl ester (2.0 g, 0.004 mmol) were dissolved in 2.0 M solution of EtNH$_2$ in THF (14 mL) in an autoclave and heated to 80° C. over night. The volatiles were removed and the crude product subjected to column chromatography (silica gel, heptane/ethyl acetate 1:1) to yield the title compound (1.2 g, 81%) as a yellow oil.

ES-MS m/e: 364.2 (M+H$^+$).

EXAMPLE 57

{(3S,4S)-3-(3,4-Dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone

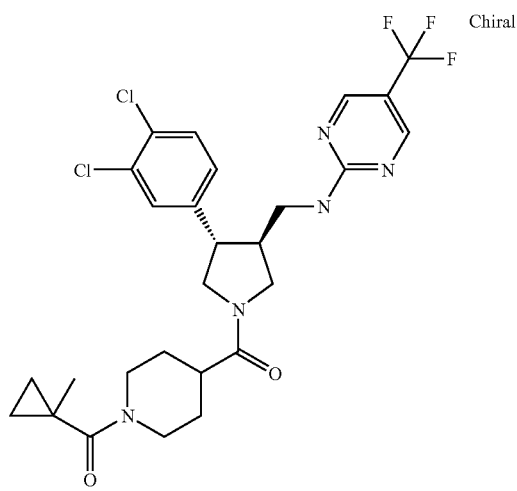

a) [(3S,4S)-1-Benzyl-4-(3,4-dichloro-phenyl)-pyrrolidin-3-ylmethyl]-(5-trifluoromethyl-pyrimidin-2-yl)-amine Nucleophilic substitution reaction according to General Procedure VI Aniline derivative: 2-Amino-5-trifluoromethylpyrimidine (CAS RN:69034-08-8)

Tosylate: Toluene-4-sulfonic acid (3R,4S)-1-benzyl-4-(3,4-dichloro-phenyl)-pyrrolidin-3-ylmethyl ester ES-MS m/e: 482.5 (M+H$^+$).

b) [(3R,4S)-4-(3,4-Dichloro-phenyl)-pyrrolidin-3-ylmethyl]-(5-trifluoromethyl-pyrimidin-2-yl)-amine Cleavage of the n-benzyl group according to General Procedure V Amine: [(3S,4S)-1-Benzyl-4-(3,4-dichloro-phenyl)-pyrrolidin-3-ylmethyl]-(5-trifluoromethyl-pyrimidin-2-yl)-amine ES-MS m/e: 392.3 (M+H$^+$).

c) {(3S,4S)-3-(3,4-Dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone Amid coupling according to General procedure I Amine: [(3R,4S)-4-(3,4-Dichloro-phenyl)-pyrrolidin-3-ylmethyl]-(5-trifluoromethyl-pyrimidin-2-yl)-amine Carboxylic acid: 1-(1-Methyl-cyclopropanecarbonyl)-piperidine-4-carboxylic acid ES-MS m/e: 584.2 (M+H$^+$).

EXAMPLE 58

{(3S,4S)-3-(3,4-Dichloro-phenyl)-4-[(5-trifluoromethyl-pyrimidin-2-ylamino)-methyl]-pyrrolidin-1-yl}-(6-methyl-pyridazin-4-yl)-methanone

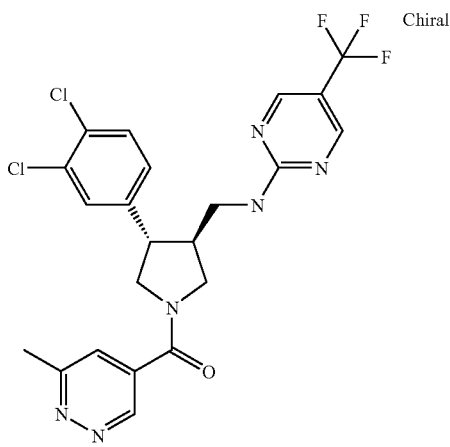

Amid coupling according to General procedure I

Amine: [(3R,4S)-4-(3,4-Dichloro-phenyl)-pyrrolidin-3-ylmethyl]-(5-trifluoromethyl-pyrimidin-2-yl)-amine Carboxylic acid: 6-Methyl-pyridazine-4-carboxylic acid ES-MS m/e: 511.2 (M+H$^+$).

EXAMPLE 59

((3S,4S)-3-(3,4-Dichloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone

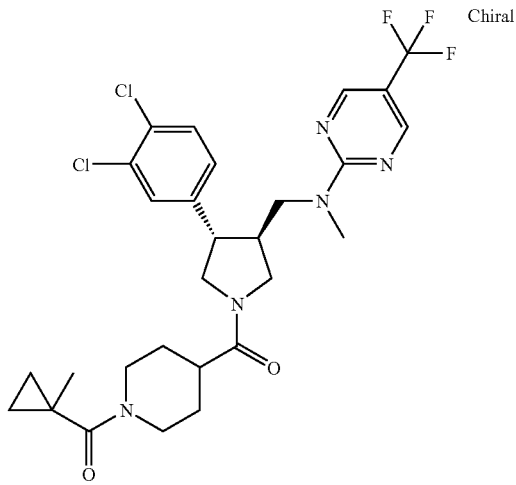

{(3S,4S)-3-(3,4-Dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone (30.0 mg, 0.051 mmol) were dissolved in DMF (1 mL) and treated with NaH (55% dispersion in oil) (2.5 mg, 0.056 mmol) at ambient temperature. After 5 min methyl iodide (3.5 µL, 0.056 mmol) were added and the reaction mixture was stirred over night. After quenching with water and extraction with ethyl acetate (3×10 mL) the combined organic phases were dried on sodium sulfate and filtered. After evaporation of the solvent the crude product was subjected to column chromatography (silica gel, ethyl acetate) to yield the title product (19 mg, 62%) as a colorless foam. ES-MS m/e: 598.3 (M+H$^+$).

EXAMPLE 60

((3S,4S)-3-(3,4-Dichloro-phenyl)-4-{[methyl-(5-trifluoromethyl-pyrimidin-2-yl)-amino]-methyl}-pyrrolidin-1-yl)-(6-methyl-pyridazin-4-yl)-methanone

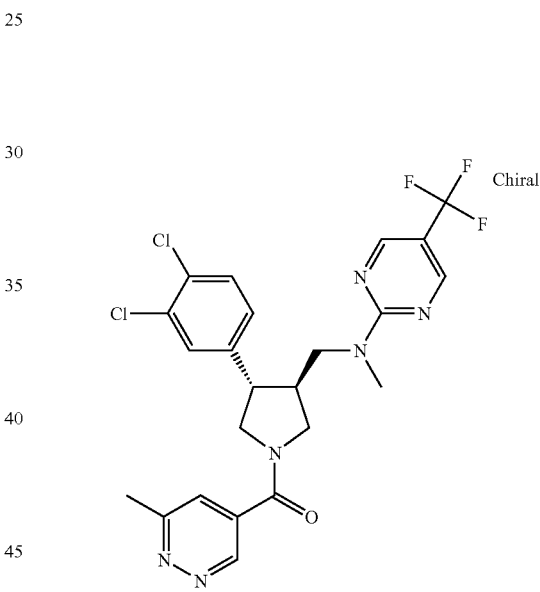

{(3S,4S)-3-(3,4-Dichloro-phenyl)-4-[(5-trifluoromethyl-pyrimidin-2-ylamino)-methyl]-pyrrolidin-1-yl)-(6-methyl-pyridazin-4-yl)-methanone (50.0 mg, 0.1 mmol) were dissolved in DMF (1 mL) and treated with NaH (55% dispersion in oil) (5 mg, 0.11 mmol) at ambient temperature. After 5 min methyl iodide (7.3 µL, 0.12 mmol) were added and the reaction mixture was stirred over night. After quenching with water and extraction with ethyl acetate (3×10 mL) the combined organic phases were dried on sodium sulfate and filtered. After evaporation of the solvent the crude product was subjected to column chromatography (silica gel, dichloro methane, dichloro methane/methanol 4:1) to yield the title product (30 mg, 58%) as a brown foam. ES-MS m/e: 525.2 (M+H$^+$).

EXAMPLE 61

((3S,4S)-3-(3,4-Dichloro-phenyl)-4-{[ethyl-(5-trifluoromethyl-pyrimidin-2-yl)-amino]-methyl}-pyrrolidin-1-yl)-[1-(1-methyl-cyclopropanecarbonyl)-piperidin-4-yl]-methanone

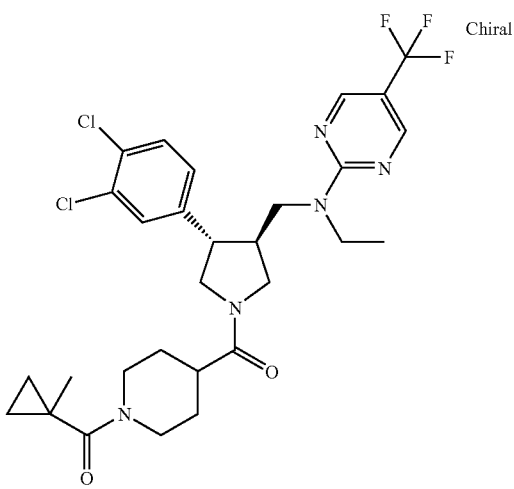

a) [(3R,4S)-1-Benzyl-4-(3,4-dichloro-phenyl)-pyrrolidin-3-ylmethyl]-ethyl-(5-trifluoromethyl-pyrimidin-2-yl)-amine Nucleophilic aromatic substitution according to General Procedure IV:
Amine: [(3S,4S)-1-Benzyl-4-(3,4-dichloro-phenyl)-pyrrolidin-3-ylmethyl]-ethyl-amine
Heteroaromatic methylsulfone: 2-Methanesulfonyl-5-trifluoromethyl-pyrimidine
ES-MS m/e: 510.4 (M+H$^+$).

b) [(3R,4S)-4-(3,4-dichloro-phenyl)-pyrrolidin-3-ylmethyl]-ethyl-(5-trifluoromethyl-pyrimidin-2-yl)-amine Cleavage of the n-benzyl group according to General Procedure V
Amine: [(3R,4S)-1-Benzyl-4-(3,4-dichloro-phenyl)-pyrrolidin-3-ylmethyl]-ethyl-(5-trifluoromethyl-pyrimidin-2-yl)-amine
ES-MS m/e: 420.3 (M+H$^+$).

c) ((3S,4S)-3-(3,4-Dichloro-phenyl)-4-{[ethyl-(5-trifluoromethyl-pyrimidin-2-yl)-amino]-methyl}-pyrrolidin-1-yl)-[1-(1-methyl-cyclopropanecarbonyl)-piperidin-4-yl]-methanone Amid coupling according to General procedure I
Amine: [(3R,4S)-4-(3,4-Dichloro-phenyl)-pyrrolidin-3-ylmethyl]-ethyl-(5-trifluoromethyl-pyrimidin-2-yl)-amine
Carboxylic acid: 1-(1-Methyl-cyclopropanecarbonyl)-piperidine-4-carboxylic acid
ES-MS m/e: 612.2 (M+H$^+$).

EXAMPLE 62

[4-((3S,4S)-3-(3,4-Dichloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone

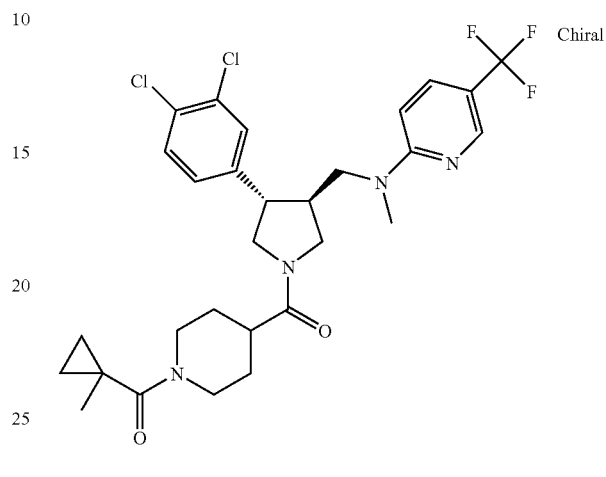

a) [(3R,4S)-1-Benzyl-4-(3,4-dichloro-phenyl)-pyrrolidin-3-ylmethyl]-methyl-(5-trifluoromethyl-pyridin-2-yl)-amine Nucleophilic aromatic substitution according to General Procedure IV:
Amine: [(3S,4S)-1-Benzyl-4-(3,4-dichloro-phenyl)-pyrrolidin-3-ylmethyl]-methyl-amine
Heteroaromatic chloride: 2-Chloro-5-trifluoromethyl-pyridine
ES-MS m/e: 494.2 (M+H$^+$).

b) [(3R,4S)-4-(3,4-Dichloro-phenyl)-pyrrolidin-3-ylmethyl]-methyl-(5-trifluoromethyl-pyridin-2-yl)-amine Cleavage of the n-benzyl group according to General Procedure V
Amine: [(3R,4S)-1-Benzyl-4-(3,4-dichloro-phenyl)-pyrrolidin-3-ylmethyl]-methyl-(5-trifluoromethyl-pyridin-2-yl)-amine
ES-MS m/e: 404.3 (M+H$^+$).

c) [4-((3S,4S)-3-(3,4-Dichloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone Amid coupling according to General procedure I
Amine: [(3R,4S)-4-(3,4-Dichloro-phenyl)-pyrrolidin-3-ylmethyl]-methyl-(5-trifluoromethyl-pyridin-2-yl)-amine
Carboxylic acid: 1-(1-Methyl-cyclopropanecarbonyl)-piperidine-4-carboxylic acid
ES-MS m/e: 597.3 (M+H$^+$).

EXAMPLE 63

((3S,4S)-3-(3,4-Dichloro-phenyl)-4-{[ethyl-(5-trifluoromethyl-pyridin-2-yl)-amino]-methyl}-pyrrolidin-1-yl)-[1-(1-methyl-cyclopropanecarbonyl)-piperidin-4-yl]-methanone

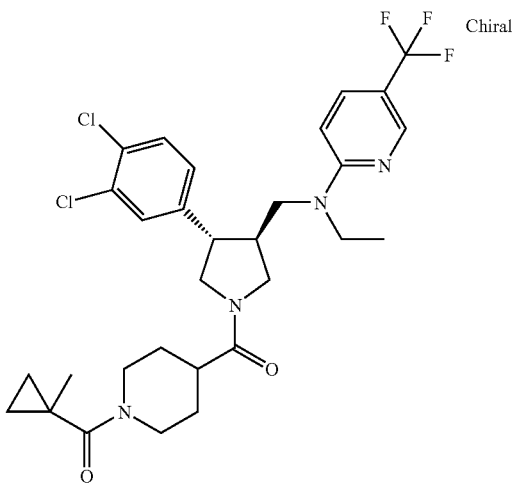

a) [(3R,4S)-1-Benzyl-4-(3,4-dichloro-phenyl)-pyrrolidin-3-ylmethyl]-ethyl-(5-trifluoromethyl-pyridin-2-yl)-amine Nucleophilic aromatic substitution according to General Procedure IV:
Amine: [(3S,4S)-1-Benzyl-4-(3,4-dichloro-phenyl)-pyrrolidin-3-ylmethyl]-ethyl-amine
Heteroaromatic chloride: 2-Chloro-5-trifluoromethyl-pyridine
ES-MS m/e: 509.2 (M+H$^+$).

b) [(3R,4S)-4-(3,4-Dichloro-phenyl)-pyrrolidin-3-ylmethyl]-ethyl-(5-trifluoromethyl-pyridin-2-yl)-amine Cleavage of the n-benzyl group according to General Procedure V
Amine: [(3R,4S)-1-Benzyl-4-(3,4-dichloro-phenyl)-pyrrolidin-3-ylmethyl]-ethyl-(5-trifluoromethyl-pyridin-2-yl)-amine
ES-MS m/e: 420.3 (M+H$^+$).

c) ((3S,4S)-3-(3,4-Dichloro-phenyl)-4-{[ethyl-(5-trifluoromethyl-pyridin-2-yl)-amino]-methyl}-pyrrolidin-1-yl)-[1-(1-methyl-cyclopropanecarbonyl)-piperidin-4-yl]-methanone Amid coupling according to General procedure I
Amine: [(3R,4S)-4-(3,4-Dichloro-phenyl)-pyrrolidin-3-ylmethyl]-ethyl-(5-trifluoromethyl-pyridin-2-yl)-amine
Carboxylic acid: 1-(1-Methyl-cyclopropanecarbonyl)-piperidine-4-carboxylic acid
ES-MS m/e: 611.2 (M+H$^+$).

EXAMPLE 64

6-({(3S,4S)-4-(3,4-Dichloro-phenyl)-1-[1-(1-methyl-cyclopropanecarbonyl)-piperidine-4-carbonyl]-pyrrolidin-3-ylmethyl}-methyl-amino)-nicotinonitrile

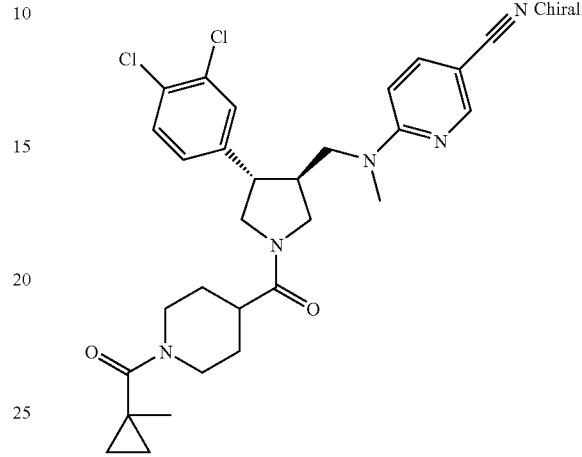

a) 6-{[(3R,4S)-1-Benzyl-4-(3,4-dichloro-phenyl)-pyrrolidin-3-ylmethyl]-methyl-amino}-nicotinonitrile Nucleophilic aromatic substitution according to General Procedure IV:
Amine: [(3S,4S)-1-Benzyl-4-(3,4-dichloro-phenyl)-pyrrolidin-3-ylmethyl]-methyl-amine
Heteroaromatic chloride: 6-Chloro-3-pyridine-carbonitrile
ES-MS m/e: 451.2 (M+H$^+$).

b) 6-{[(3R,4S)-4-(3,4-Dichloro-phenyl)-pyrrolidin-3-ylmethyl]-methyl-amino}-nicotinonitrile Cleavage of the n-benzyl group according to General Procedure V
Amine: 6-{[(3R,4S)-1-Benzyl-4-(3,4-dichloro-phenyl)-pyrrolidin-3-ylmethyl]-methyl-amino}-nicotinonitrile
ES-MS m/e: 361.2 (M+H$^+$).

c) 6-({(3S,4S)-4-(3,4-Dichloro-phenyl)-1-[1-(1-methyl-cyclopropanecarbonyl)-piperidine-4-carbonyl]-pyrrolidin-3-ylmethyl}-methyl-amino)-nicotinonitrile Amid coupling according to General procedure I
Amine: 6-{[(3R,4S)-4-(3,4-Dichloro-phenyl)-pyrrolidin-3-ylmethyl]-methyl-amino}-nicotinonitrile
Carboxylic acid: 1-(1-Methyl-cyclopropanecarbonyl)-piperidine-4-carboxylic acid
ES-MS m/e: 554.3 (M+H$^+$).

EXAMPLE 65

6-{[(3S,4S)-4-(3,4-Dichloro-phenyl)-1-(6-methyl-pyridazine-4-carbonyl)-pyrrolidin-3-ylmethyl]-methyl-amino}-nicotinonitrile

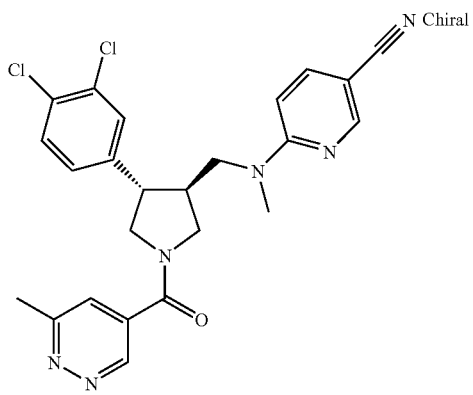

Amid coupling (pyrrolidine V, X or XV and carboxylic acid) according to General procedure I
Amine: 6-{[(3R,4S)-4-(3,4-Dichloro-phenyl)-pyrrolidin-3-ylmethyl]-methyl-amino}-nicotinonitrile
Carboxylic acid: 6-Methyl-pyridazine-4-carboxylic acid
ES-MS m/e: 481.2 (M+H$^+$).

EXAMPLE 66

{4-[(3S,4S)-3-{[(5-Chloro-pyridin-2-yl)-methyl-amino]-methyl}-4-(3,4-dichloro-phenyl)-pyrrolidine-1-carbonyl]-piperidin-1-yl}-(1-methyl-cyclopropyl)-methanone

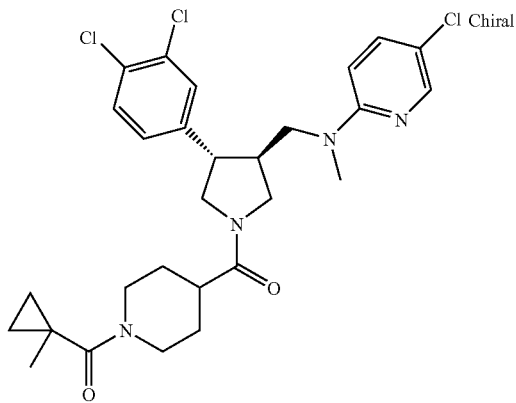

a) [(3R,4S)-1-Benzyl-4-(3,4-dichloro-phenyl)-pyrrolidin-3-ylmethyl]-(5-chloro-pyridin-2-yl)-methyl-amine Nucleophilic aromatic substitution according to General Procedure IV:
Amine: [(3S,4S)-1-Benzyl-4-(3,4-dichloro-phenyl)-pyrrolidin-3-ylmethyl]-methyl-amine
Heteroaromatic chloride: 2,5-Dichloro-pyridine (CAS RN: 16110-09-1)
ES-MS m/e: 462.2 (M+H$^+$).

b) (5-Chloro-pyridin-2-yl)-[(3R,4S)-4-(3,4-dichloro-phenyl)-pyrrolidin-3-ylmethyl]-methyl-amine Cleavage of the n-benzyl group according to General Procedure V
Amine: [(3R,4S)-1-Benzyl-4-(3,4-dichloro-phenyl)-pyrrolidin-3-ylmethyl]-(5-chloro-pyridin-2-yl)-methyl-amine
ES-MS m/e: 372.0 (M+H$^+$).

c) {4-[(3S,4S)-3-{[5-Chloro-pyridin-2-yl)-methyl-amino]-methyl}-4-(3,4-dichloro-phenyl)-pyrrolidine-1-carbonyl]-piperidin-1-yl}-(1-methyl-cyclopropyl)-methanone Amid coupling according to General procedure I
Amine: (5-Chloro-pyridin-2-yl)-[(3R,4S)-4-(3,4-dichloro-phenyl)-pyrrolidin-3-ylmethyl]-methyl-amine
Carboxylic acid: 1-(1-Methyl-cyclopropanecarbonyl)-piperidine-4-carboxylic acid
ES-MS m/e: 563.2 (M+H$^+$).

As mentioned earlier, the compounds of formula I and their pharmaceutically usable addition salts possess valuable pharmacological properties Compounds of the present invention are antagonists of neurokinin 3 (NK-3) receptors. The compounds were investigated in accordance with the tests given hereinafter.

Experimental Procedure

The compounds were investigated in accordance with the tests given hereinafter

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µA) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

Results of some compounds with a hNK-3 receptor affinity <0.10 µM are shown in the following table 1.

TABLE 1

| Example | Data $K_i$ [µM] |
|---|---|
| 1 | 0.0496 |
| 2 | 0.0459 |
| 4 | 0.0617 |
| 5 | 0.0024 |
| 6 | 0.0022 |
| 8 | 0.0711 |
| 12 | 0.02 |
| 13 | 0.0066 |
| 14 | 0.0924 |
| 15 | 0.0788 |
| 17 | 0.0096 |
| 19 | 0.0103 |
| 20 | 0.011 |
| 21 | 0.0089 |
| 22 | 0.0986 |
| 23 | 0.0109 |
| 24 | 0.0165 |
| 25 | 0.0195 |
| 26 | 0.0463 |
| 27 | 0.0247 |
| 28 | 0.0585 |
| 30 | 0.0361 |
| 31 | 0.08 |
| 33 | 0.0075 |
| 34 | 0.0062 |
| 35 | 0.009 |
| 36 | 0.0682 |
| 37 | 0.0549 |
| 38 | 0.0223 |
| 41 | 0.0863 |
| 46 | 0.0228 |
| 47 | 0.0716 |
| 51 | 0.0699 |
| 53 | 0.0856 |
| 55 | 0.0429 |
| 57 | 0.0018 |
| 58 | 0.0012 |
| 59 | 0.0023 |
| 60 | 0.0158 |
| 62 | 0.0084 |
| 64 | 0.0318 |
| 66 | 0.047 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. gelatingelatinLactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:

1. A compound of formula I

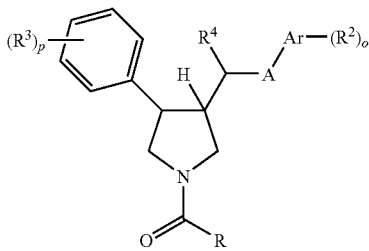

wherein

A is —NR'—, —S—, —S(O)— or —S(O)$_2$—;

R' is hydrogen or lower alkyl;

Ar is a six membered heteroaryl group containing one or two N-atoms;

R is a six membered heterocyclic group

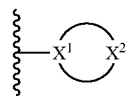

wherein

X$^1$ is N or CH; and

X$^2$ is —N(R$^1$)—, —CH$_2$—, —O—, —S—, —S(O)—, or —S(O)$_2$—,

R$^1$ is hydrogen, lower alkyl, S(O)$_2$-lower alkyl, C(O)-lower alkyl, C(O)-cycloalkyl optionally substituted by lower alkyl;

with the proviso that at least one of X$^1$ or X$^2$ contains a heteroatom, or is a five or six membered heteroaryl group containing one or two N-atoms, which groups are unsubstituted or are substituted by one or two R$^{1'}$;

wherein

R$^{1'}$ is lower alkyl or cyano;

R$^2$ is lower alkyl substituted by halogen, cyano or nitro;

R$^3$ is halogen;

R$^4$ is hydrogen or lower alkyl;

o is 1 or 2; wherein when o is 2, each R$^2$ is the same or different; and p is 1 or 2; wherein when p is 2, each R$^3$ is the same or different;

or a pharmaceutically active salt, a racemic mixture, an enantiomer, an optical isomer or a tautomeric form thereof.

2. The compound of claim 1 having formula I-A

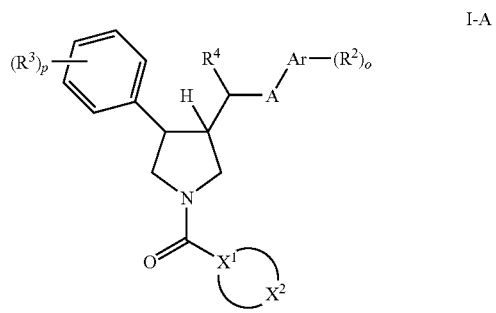

wherein

A is —NR'—, —S—, —S(O)— or —S(O)$_2$—;

R' is hydrogen or lower alkyl;

Ar is a six membered heteroaryl group containing one or two N-atoms;

X$^1$ is N or CH; and

X$^2$ is —N(R$^1$)—, —CH$_2$—, —O—, —S—, —S(O)—, or —S(O)$_2$—,

R$^1$ is hydrogen, lower alkyl, S(O)$_2$-lower alkyl, C(O)-lower alkyl, C(O) -cycloalkyl optionally substituted by lower alkyl;

with the proviso that at least one of X$^1$ or X$^2$ contains a heteroatom,

R$^2$ is lower alkyl substituted by halogen, cyano or nitro;

R$^3$ is halogen;

R$^4$ is hydrogen or lower alkyl;

o is 1 or 2; wherein when o is 2, each R$^2$ is the same or different; and p is 1 or 2; wherein when p is 2, each R$^3$ is the same or different;

or a pharmaceutically active salt, a racemic mixture, an enantiomer, an optical isomer or a tautomeric form thereof.

3. The compound of claim 2 wherein

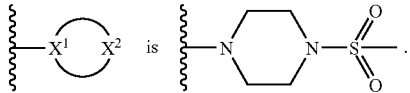

4. The compound of claim 3, selected from the group consisting of (3SR,4RS)-[3-(3,4-dichloro-phenyl)-4-(5-trifluoromethyl-pyridin-2-ylsulfanylmethyl)-pyrrolidin-1-yl]-(4-methanesulfonyl-piperazin-1-yl)-methanone;

(3SR,4RS)-[3-(5-chloro-pyridin-2-ylsulfanylmethyl)-4-(3,4-dichloro-phenyl)-pyrrolidin-1-yl]-(4-methanesulfonyl-piperazin-1-yl)-methanone;

(3SR,4RS)-[3-(3,4-dichloro-phenyl)-4-[(5-nitro-pyridin-2-ylamino)-methyl]-pyrrolidin-1-yl]-(4-methanesulfonyl-piperazin-1-yl)-methanone;

(3SR,4RS)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone;

(3S,4S)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone; and (3R,4R)-{3-(3,4-dichloro-phenyl)-4-[(5-trifluoromethyl-pyridin-2-ylamino)-methyl]-pyrrolidin-1-yl}-(4-methanesulfonyl-piperazin-1-yl)-methanone.

5. The compound of claim 3, selected from the group consisting of (3SR,4RS)-3-(3,4-dichloro-phenyl)-4-{[methyl-(5-trifluoromethyl-pyridin-2-yl)-amino]-methyl}-pyrrolidin-1-yl)-(4-methanesulfonyl-piperazin-1-yl)-methanone;

(3SR,4RS)-[3-[(5-chloro-pyridin-2-ylamino)-methyl]-4-(3,4-dichloro-phenyl)-pyrrolidin-1-yl]-(4-methanesulfonyl-piperazin-1-yl)-methanone;

(3SR,4RS)-2-{[4-(3,4-dichloro-phenyl)-1-(4-methanesulfonyl-piperazine-1-carbonyl)-pyrrolidin-3-ylmethyl]-amino}-pyrimidine-5-carbonitrile;

(3SR,4RS) 6-{1-(RS)-[4-(3,4-dichloro-phenyl)-1-(4-methanesulfonyl-piperazine-1-carbonyl)-pyrrolidin-3-yl]-ethylamino}-nicotinonitrile;

(3SR,4RS) 6-{1-(SR)-[4-(3,4-Dichloro-phenyl)-1-(4-methanesulfonyl-piperazine-1-carbonyl)-pyrrolidin-3-yl]-ethylamino}-nicotinonitrile;

(3SR,4RS) {3-(3,4-dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone;

(3SR,4RS) {3-(3,4-dichloro-phenyl)-4-[1-(SR)-(5-trifluoromethyl-pyridin-2-ylamino)-ethyl]-pyrrolidin-1-yl}-(4-methanesulfonyl-piperazin-1-yl)-methanone; and (3SR,4RS) {3-(3,4-dichloro-phenyl)-4-[1-(RS)-(5-trifluoromethyl-pyridin-2-ylamino)-ethyl]-pyrrolidin-1-yl}-(4-methanesulfonyl-piperazin-1-yl)-methanone.

6. The compound of claim 2 wherein

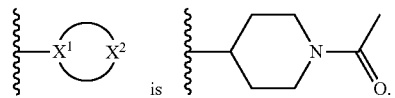

7. The compound of claim 6, selected from the group consisting of (3SR,4RS)-1-(4-{-3-(3,4-dichloro-phenyl)-4-[(5-trifluoromethyl-pyridin-2-ylamino)-methyl]-pyrrolidine-1-carbonyl}-piperidin-1-yl)-ethanone;

(3SR,4RS)-{1-{4-[3-[(5-chloro-pyrimidin-2-ylamino)-methyl]-4-(3,4-dichloro-phenyl)-pyrrolidine-1-carbonyl]-piperidin-1-yl}-ethanone; and (3SR,4RS) 1-(4-{3-(3,4-dichloro-phenyl)-4-[(5-trifluoromethyl-pyridin-2-ylamino)-methyl]-pyrrolidine-1-carbonyl}-piperidin-1-yl)-ethanone.

8. The compound of claim 2 wherein

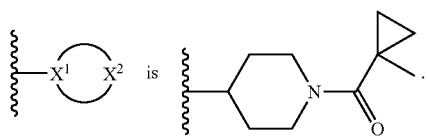

9. The compound of claim 8, selected from the group consisting of (3SR,4RS)-(3-(3,4-dichloro-phenyl)-4-[(5-trifluoromethyl-pyridin-2-ylamino)-methyl]-pyrrolidine-1-carbonyl}-piperidin-1-yl)-(1-methyl-cyclopropyl)-methanone;

(3SR,4RS)-{3-[(5-chloro-pyrimidin-2-ylamino)-methyl]-4-(3,4-dichloro-phenyl)-pyrrolidin-1-yl]-[1-(1-methyl-cyclopropanecarbonyl)-piperidin-4-yl]-methanone;

(3SR,4RS) {3-(3,4-dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;

(3SR,4RS) {3-(4-chloro-phenyl)-4-[(5-chloro-pyridin-2-ylamino)-methyl]-pyrrolidin-1-yl]-[1-(1-methyl-cyclopropanecarbonyl)-piperidin-4-yl]-methanone;

(3SR,4RS) {3-(4-fluoro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;

(3SR,4RS) [4-(3-(4-fluoro-phenyl)-4-{[methyl-(5-trifluoromethyl-pyrimidin-2-yl)-amino]-methyl}-pyrrolidine-1-carbonyl)-piperidin-1-yl]-(1-methyl-cyclopropyl)-methanone;

6-({(3S,4S)-4-(4-chloro-phenyl)-1-[1-(1-methyl-cyclopropanecarbonyl)-piperidine-4-carbonyl]-pyrrolidin-3-ylmethyl}-methyl-amino)-nicotinonitrile;

[4-((3S,4S)-3-(4-chloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone;

((3S,4S)-3-(4-chloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone;

{(3S,4S)-3-(3,4-dichloro-phenyl)-4-[(5-trifluoromethyl-pyrimidin-2-ylamino)-methyl]-pyrrolidin-1-yl}-[1-(1-methyl-cyclopropanecarbonyl)-piperidin-4-yl]-methanone;

((3S,4S)-3-(3,4-dichloro-phenyl)-4-{[methyl-(5-trifluoromethyl-pyrimidin-2-yl)-amino]-methyl}-pyrrolidin-1-yl)-[1-(1-methyl-cyclopropanecarbonyl)-piperidin-4-yl]-methanone;

[4-((3S,4S)-3-(3,4-dichloro-phenyl)-4-{[methyl-(5-trifluoromethyl-pyridin-2-yl)-amino]-methyl}-pyrrolidine-1-carbonyl)-piperidin-1-yl]-(1-methyl-cyclopropyl)-methanone;

6-({(3S,4S)-4-(3,4-dichloro-phenyl)-1-[1-(1-methyl-cyclopropanecarbonyl)-piperidine-4-carbonyl]-pyrrolidin-3-ylmethyl}-methyl-amino)-nicotinonitrile; and {4-[(3S,4S)-3-{[(5-chloro-pyridin-2-yl)-methyl-amino]-methyl}-4-(3,4-dichloro-phenyl)-pyrrolidine-1-carbonyl]-piperidin-1-yl}-(1-methyl-cyclopropyl)-methanone.

10. A pharmaceutical composition comprising a therapeutically effective amount of a compound of formula I

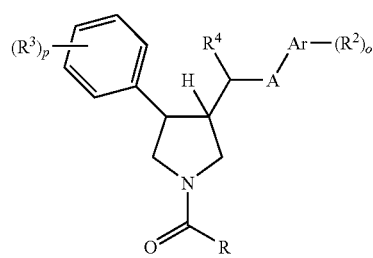

wherein
A is $-NR'-$, $-S-$, $-S(O)-$ or $-S(O)_2-$;
R' is hydrogen or lower alkyl;
Ar is a six membered heteroaryl group containing one or two N-atoms;

R is a six membered heterocyclic group

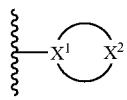

wherein
X$^1$ is N or CH; and
X$^2$ is —N(R$^1$)—, —CH$_2$—, —O—, —S—, —S(O)—, or —S(O)$_2$—,
R$^1$ is hydrogen, lower alkyl, S(O)$_2$-lower alkyl, C(O)-lower alkyl, C(O)-cycloalkyl optionally substituted by lower alkyl;
with the proviso that at least one of X$^1$ or X$^2$ contains a heteroatom,
or is a five or six membered heteroaryl group containing one or two N-atoms, which groups are unsubstituted or are substituted by one or two R$^{1'}$;
wherein
R$^{1'}$ is lower alkyl or cyano;
R$^2$ is lower alkyl substituted by halogen, cyano or nitro;
R$^3$ is halogen;
R$^4$ is hydrogen or lower alkyl;
o is 1 or 2; wherein when o is 2, each R$^2$ is the same or different; and
p is 1 or 2; wherein when p is 2, each R$^3$ is the same or different;
or a pharmaceutically active salt, a racemic mixture, an enantiomer, an optical isomer or a tautomeric form thereof and a pharmaceutically acceptable carrier.

* * * * *